(12) United States Patent
Killebrew et al.

(10) Patent No.: US 12,221,404 B2
(45) Date of Patent: Feb. 11, 2025

(54) COMPOSITION COMPRISING BRANCHED ALDEHYDES

(71) Applicant: SCION Holdings LLC, Houston, TX (US)

(72) Inventors: Kyle Killebrew, Houston, TX (US); Samuel Livingston Lane, Seabrook, TX (US)

(73) Assignee: SCION Holdings LLC, Houston, TX (US)

( * ) Notice: Subject to any disclaimer, the term of this patent is extended or adjusted under 35 U.S.C. 154(b) by 0 days.

(21) Appl. No.: 17/338,641

(22) Filed: Jun. 3, 2021

(65) Prior Publication Data

US 2021/0387933 A1    Dec. 16, 2021

Related U.S. Application Data

(63) Continuation-in-part of application No. 17/246,580, filed on Apr. 30, 2021, now Pat. No. 11,680,032, and a continuation-in-part of application No. PCT/US2021/030341, filed on Apr. 30, 2021, and a continuation-in-part of application No. 17/331,371, filed on May 26, 2021, which is a continuation-in-part of application No. 17/246,580, filed on Apr. 30, 2021, now Pat. No. 11,680,032, and a continuation-in-part of application No. PCT/US2021/030341, filed on Apr. 30, 2021, application No. 17/338,641 is a continuation-in-part of application No. PCT/US2021/034189, filed on May 26, 2021, which is a continuation-in-part of application No. 17/246,580, filed on Apr. 30, 2021, now Pat. No. 11,680,032, and a continuation-in-part of application No. PCT/US2021/030341, filed on Apr. 30, 2021, application No. 17/338,641 is a continuation-in-part of application No. 17/336,099, filed on Jun. 1, 2021, now Pat. No. 12,054,455, which is a continuation-in-part of application No. 17/246,580, filed on Apr. 30, 2021, now Pat. No. 11,680,032, and a continuation-in-part of application No. PCT/US2021/030341, filed on Apr. 30, 2021, and a continuation-in-part of application No. 17/331,371, filed on May 26, 2021, which is a continuation-in-part of application No. 17/246,580, filed on Apr. 30, 2021, now Pat. No. 11,680,032, and a continuation-in-part of application No. PCT/US2021/030341, filed on Apr. 30, 2021, said application No. 17/336,099 is a continuation-in-part of application No. PCT/US2021/034189, filed on May 26, 2021, which is a continuation-in-part of application No. 17/246,580, filed on Apr. 30, 2021, now Pat. No. 11,680,032, said application No. PCT/US2021/034189 is a continuation-in-part of application No. PCT/US2021/030341, filed on Apr. 30, 2021, application No. 17/338,641 is a continuation-in-part of application No. PCT/US2021/035169, filed on Jun. 1, 2021, which is a continuation-in-part of application No. 17/246,580, filed on Apr. 30, 2021, now Pat. No. 11,680,032, and a continuation-in-part of application No. PCT/US2021/030341, filed on Apr. 30, 2021, and a continuation-in-part of application No. 17/331,371, filed on May 26, 2021, which is a continuation-in-part of application No. 17/246,580, filed on Apr. 30, 2021, now Pat. No. 11,680,032, and a continuation-in-part (Continued)

(51) Int. Cl.
*C07C 47/02* (2006.01)
*B01J 31/18* (2006.01)
*C07C 29/141* (2006.01)
*C07C 45/50* (2006.01)

(52) U.S. Cl.
CPC ........... *C07C 29/141* (2013.01); *B01J 31/185* (2013.01); *C07C 45/505* (2013.01); *C07C 47/02* (2013.01); *B01J 2231/321* (2013.01); *B01J 2531/822* (2013.01)

(58) Field of Classification Search
None
See application file for complete search history.

(56) References Cited

U.S. PATENT DOCUMENTS 3,480,556 A    11/1969   De Witt et al.
4,336,032 A    6/1982    Kupka et al.
(Continued)

FOREIGN PATENT DOCUMENTS

CN    101768060 B    7/2013
CN    106496541 A    3/2017
(Continued)

OTHER PUBLICATIONS

Mathivet, T. et al. "Perfluorooctyl substituted triphenylphosphites as ligands for hydroformylation of higher olefins in fluorocarbon/hydrocarbon biphasic medium" C. R. Chimie 5 (2002) 417-424 (Year: 2002).*

(Continued)

*Primary Examiner* — Medhanit W Bahta
(74) *Attorney, Agent, or Firm* — Wright IP & International Law; Eric G. Wright

(57) ABSTRACT

A process for producing isomerized olefins, branched aldehydes, branched alcohols, branched surfactants and other branched derivatives through isomerization, hydroformylation, hydrogenation, surfactant forming reactions and other derivative forming reactions.

12 Claims, 18 Drawing Sheets

Related U.S. Application Data of application No. PCT/US2021/030341, filed on Apr. 30, 2021, said application No. PCT/US2021/035169 is a continuation-in-part of application No. PCT/US2021/034189, filed on May 26, 2021, which is a continuation-in-part of application No. 17/246,580, filed on Apr. 30, 2021, now Pat. No. 11,680,032, and a continuation-in-part of application No. PCT/US2021/030341, filed on Apr. 30, 2021.

(60) Provisional application No. 63/035,479, filed on Jun. 5, 2020, provisional application No. 63/035,073, filed on Jun. 5, 2020, provisional application No. 63/035,280, filed on Jun. 5, 2020, provisional application No. 63/126,780, filed on Dec. 17, 2020.

(56) References Cited

U.S. PATENT DOCUMENTS

| | | |
|---|---|---|
| 4,443,638 A | 4/1984 | Yates |
| 4,528,245 A | 7/1985 | Jobbins |
| 4,528,404 A | 7/1985 | Oswald et al. |
| 4,642,388 A | 2/1987 | Young |
| 4,670,606 A | 6/1987 | Romano et al. |
| 4,922,028 A | 5/1990 | Oswald et al. |
| 4,940,574 A | 7/1990 | Kaplan |
| 5,030,774 A * | 7/1991 | Oswald .......... C07C 45/50 568/454 |
| 5,364,552 A | 11/1994 | Merz et al. |
| 5,481,044 A | 1/1996 | Weber et al. |
| 5,574,084 A | 11/1996 | Peacock |
| 5,789,367 A | 8/1998 | Blokzijl et al. |
| 5,833,719 A | 11/1998 | Francois et al. |
| 5,849,960 A | 12/1998 | Singleton et al. |
| 5,919,987 A | 7/1999 | Kneuper et al. |
| 6,225,507 B1 | 5/2001 | Giessler et al. |
| 6,448,213 B1 | 9/2002 | Willman |
| 6,500,991 B2 | 12/2002 | Wiese et al. |
| 6,514,926 B1 | 2/2003 | Kott et al. |
| 6,653,514 B1 | 11/2003 | Murray et al. |
| 6,765,106 B2 | 7/2004 | Fenouil et al. |
| 6,770,722 B2 | 8/2004 | Weitzel et al. |
| 6,849,589 B2 | 2/2005 | Liu |
| 7,022,889 B2 | 4/2006 | Gillespie et al. |
| 7,074,395 B2 | 7/2006 | Milbradt et al. |
| 7,183,446 B2 | 2/2007 | Zeller et al. |
| 7,223,898 B2 | 5/2007 | Rice |
| 7,232,931 B2 | 6/2007 | Toetsch et al. |
| 7,250,468 B2 | 7/2007 | Harzschel et al. |
| 7,300,966 B2 | 11/2007 | Breitscheidel et al. |
| 7,335,802 B2 | 2/2008 | Ayoub et al. |
| 7,365,234 B2 | 4/2008 | Subramaniam et al. |
| 7,541,414 B2 | 6/2009 | Lion |
| 7,615,645 B2 | 11/2009 | Volland et al. |
| 7,863,487 B2 | 1/2011 | Eisenschmid et al. |
| 7,906,688 B2 | 3/2011 | Brammer et al. |
| 7,956,113 B2 | 6/2011 | Killat et al. |
| 8,178,729 B2 | 5/2012 | Karvinen et al. |
| 8,334,323 B2 | 12/2012 | Varineau et al. |
| 8,586,686 B2 | 11/2013 | Zecha et al. |
| 8,692,027 B2 | 4/2014 | Norman et al. |
| 8,901,058 B2 | 12/2014 | Evers et al. |
| 9,493,725 B2 | 11/2016 | Vinson et al. |
| 9,493,726 B2 | 11/2016 | Vinson et al. |
| 9,828,565 B2 | 11/2017 | Sharko |
| 9,828,573 B2 | 11/2017 | Sharko |
| 9,890,105 B2 | 2/2018 | Krill et al. |
| 9,944,773 B2 | 4/2018 | Alidedeoglu et al. |
| 10,196,336 B2 | 2/2019 | Elowe et al. |
| 10,233,467 B2 | 3/2019 | Huo et al. |
| 10,501,392 B2 | 12/2019 | Fridag et al. |
| 10,562,833 B2 | 2/2020 | Fridag et al. |
| 10,577,297 B2 | 3/2020 | Fridag et al. |
| 10,676,762 B2 | 6/2020 | Huo et al. |
| 10,766,833 B2 | 9/2020 | Zhang |
| 11,680,032 B2 | 6/2023 | Killebrew et al. |
| 2002/0183567 A1 | 12/2002 | Fenouil et al. |
| 2004/0030200 A1 | 2/2004 | Zeller et al. |
| 2005/0107637 A1 | 5/2005 | Gerlach et al. |
| 2007/0260021 A1 | 11/2007 | Lumpp |
| 2010/0069680 A1 | 3/2010 | Eisenschmid et al. |
| 2010/0261628 A1 | 10/2010 | Scherer et al. |
| 2011/0206630 A1 | 8/2011 | Rude |
| 2012/0010423 A1 | 1/2012 | Scheibel et al. |
| 2012/0149629 A1 | 6/2012 | Dahms et al. |
| 2012/0220507 A1 | 8/2012 | Grass et al. |
| 2012/0302477 A1 | 11/2012 | Langston et al. |
| 2013/0237726 A1 | 9/2013 | Krokoszinski et al. |
| 2013/0324767 A1 | 12/2013 | Norman et al. |
| 2014/0142013 A1 | 5/2014 | Elomari |
| 2016/0068784 A1 | 3/2016 | Vinson et al. |
| 2017/0051195 A1 | 2/2017 | Vanzin et al. |
| 2017/0355656 A1 | 12/2017 | Brammer et al. |
| 2019/0337866 A1 | 11/2019 | Zhang |
| 2021/0078925 A1 | 3/2021 | Zuend et al. |
| 2021/0380510 A1 | 12/2021 | Killebrew et al. |
| 2021/0380516 A1 | 12/2021 | Killebrew et al. |
| 2021/0380902 A1 | 12/2021 | Vinson et al. |
| 2021/0387933 A1 | 12/2021 | Killebrew et al. |
| 2021/0395643 A1 | 12/2021 | Biiliauw et al. |
| 2022/0024837 A1 | 1/2022 | Killebrew et al. |
| 2022/0064569 A1 | 3/2022 | Vinson et al. |
| 2022/0176361 A1 | 6/2022 | Killebrew et al. |
| 2022/0194886 A1 | 6/2022 | Killebrew et al. |
| 2022/0194887 A1 | 6/2022 | Killebrew et al. |
| 2022/0289650 A1 | 9/2022 | Killebrew et al. |
| 2022/0315515 A2 | 10/2022 | Killebrew et al. |
| 2023/0021297 A9 | 1/2023 | Killebrew et al. |
| 2023/0159422 A1 | 5/2023 | Killebrew et al. |
| 2023/0219871 A1 | 7/2023 | Killebrew et al. |
| 2023/0219873 A1 | 7/2023 | Killebrew et al. |
| 2023/0271906 A1 | 8/2023 | Killebrew et al. |
| 2023/0303488 A1 | 9/2023 | Killebrew et al. |
| 2023/0357116 A1 | 11/2023 | Killebrew et al. |
| 2024/0034712 A1 | 2/2024 | Killebrew et al. |

FOREIGN PATENT DOCUMENTS

| | | |
|---|---|---|
| EP | 1008580 A1 | 6/2000 |
| EP | 1680387 B1 | 9/2007 |
| EP | 1678109 B1 | 1/2011 |
| WO | 8403697 | 9/1984 |
| WO | 9314057 | 7/1993 |
| WO | 199739091 | 10/1997 |
| WO | 9823566 A1 | 6/1998 |
| WO | 2005009934 A2 | 2/2005 |
| WO | 2005037753 A1 | 4/2005 |
| WO | 2008115740 A1 | 9/2008 |
| WO | 2017223271 A1 | 12/2017 |
| WO | 2020057878 A1 | 3/2020 |
| WO | 2021247177 A1 | 12/2021 |
| WO | 2021247314 A1 | 12/2021 |
| WO | 2021247516 A1 | 12/2021 |
| WO | 2021247801 A1 | 12/2021 |
| WO | 2021247917 A1 | 12/2021 |
| WO | 2022133157 A1 | 6/2022 |
| WO | 2022256272 A1 | 12/2022 |
| WO | 2023235268 A1 | 12/2023 |

OTHER PUBLICATIONS

Sakakura, T. et al. "Remarkable Effect of the Wavelength in the Photoassisted Carbonylation of the C—H Bond of Decane in the Presence of RhCl(CO)(PR3)2 as the Catalyst" Chem. Lett. 1988, pp. 155-158 (Year: 1988).*

PCT International Search Report, Application No. PCT/US2021/035772, ISA (Oct. 26, 2021).

PCT International Search Report, Application No. PCT/US2021/034189, ISA (Sep. 24, 2021).

PCT International Search Report, Application No. PCT/US2021/035169, ISA (Aug. 31, 2021).

(56) References Cited

OTHER PUBLICATIONS

PCT International Search Report, Application No. PCT/US2021/030341, ISA (Aug. 3, 2021).
Hanson, Brian E. Hydroformylation of 1-Hexene Utilizing Homogeneous Rhodium Catalysts. Journal of Chemical Education, vol. 64 (11), 928-930 (Year: 1987).
Baoxin Zhang et al., "Hydroformylation", ChemTexts 8:2 (2022), Springer Nature (Dec. 2, 2021), https://doi.org/10.1007/s40828-021-00154-x.
Richard Tudor et al., "Industrial Low Pressure Hydroformylation: Forty-Five Years of Progress For the LP Oxo(SM) Process", Johnson Matthey Technol. Rev., 61(3), 246-256 (2017), https://doi.org/10.1595/205651317X695875.
Robert Franke et al., "Applied Hydroformylation", Chem. Rev., 112, 5675-5732 (2012), ACS Publications (Aug. 31, 2012), https://dx.doi.org/10.1021/cr3001803.
Jeffrey J. Scheibel, "The Evolution of Anionic Surfactant Technology to Meet the Requirements of the Laundry Detergent Industry", AOCS Press, Journal of Surfactants and Detergents, 7(4), 319 (Oct. 2004).
"Catalysis By Metal Complexes: Rhodium Catalyzed Hydroformylation", Kluwer Academic Publishers (Piet W.N.M. van Leeuwen & Carmen Claver eds.), vol. 22 (2000), https://doi.org/10.1007/0-306-46947-2.
International Preliminary Report On Patentability, Application No. PCT/US2021/035169, IPEA/US (Apr. 11, 2022).
International Preliminary Report On Patentability, Application No. PCT/US2021/030341, IPEA/US (Apr. 7, 2022).
Wu et al., "Branched Alkyl Alcohol Propoxylated Sulfate Surfactants For Improved Oil Recovery", Tenside Surf. Det. 47 (2010) 3.
Examination Report, Application No. 202227065719, IPI (Jan. 17, 2023).
PCT International Preliminary Report On Patentability, Application No. PCT/US2021/035772, IPEA (Dec. 9, 2022).
PCT International Search Report, Application No. PCT/US2022/031481, ISA (Aug. 24, 2022).
PCT International Preliminary Report On Patentability, Application No. PCT/US2021/063934, IPEA (Jul. 22, 2022).
PCT International Search Report, Application No. PCT/US2021/063934, ISA (May 11, 2022).
PCT International Preliminary Report On Patentability, Application No. PCT/US2021/034189, IPEA (May 9, 2022).
PCT International Search Report, Application No. PCT/US2023/023775, ISA (Aug. 30, 2023).
Communication Pursuant to Rules 161(2) and 162 EPC, Application No. 21816908.4-1111, EPO (Jan. 13, 2023).
PCT International Preliminary Report On Patentability, Application No. PCT/US2022/031481, IPEA (May 11, 2023).
Hearing Notice in Reference of Application No. 202227065719, IPI (Feb. 26, 2024).
Extended European Search Report, Application No. 21818743.3, EPO (Feb. 13, 2024).
Substantive Examination Report, Application No. 522441364, SAIP (Dec. 29, 2022).
"LIAL ALCHEM ISALCHEM C9-C17 alcohols", Sasol Performance Chemicals, Brochure (May 2016).

* cited by examiner

SALES SPECIFICATION 1

For more information and technical assistance contact:

Chevron Phillips Chemical Company LP
P.O. Box 4910
The Woodlands, TX 77387-4910
800.231.3260

NORMAL ALPHA OLEFINS

AlphaPlus® 1-Dodecene
Sales Specifications

| Characteristics | Method | Units | Target | Minimum | Maximum | Note |
|---|---|---|---|---|---|---|
| Less than $C_{10}$ | GLC | Wt % | --- | --- | 0.05 | --- |
| $C_{10}$ | GLC | Wt % | --- | --- | 1.00 | --- |
| $C_{12}$ | GLC | Wt % | --- | 98.0 | --- | --- |
| $C_{14}$ | GLC | Wt % | --- | --- | 2.00 | --- |
| Greater than $C_{14}$ | GLC | Wt % | --- | --- | 0.05 | --- |
| n-Alpha Olefin | GLC | Wt % | --- | 94.6 | --- | --- |
| Vinylidene | GLC | Wt % | --- | --- | 4.2 | --- |
| cis- and trans-2-Dodecene | GLC | Wt % | --- | --- | 0.34 | --- |
| Paraffin | GLC | Wt % | --- | --- | 0.34 | --- |
| Water | ASTM E1064 | PPM by Wt | --- | --- | 100 | --- |
| Color | ASTM D6045 | Saybolt | --- | --- | 30 | --- |
| Appearance | ASTM D4176 | --- | --- | Clear and Bright | --- | --- |
| API Gravity @ 60°F | ASTM D4052 | --- | --- | --- | --- | note 1 |
| Specific Gravity @ 60°F/60°F | ASTM D4052 | --- | --- | --- | --- | note 1 |

1. Run and record

MSDS # 100000068203                     Revision Date July 2010

Another quality product from

*Chevron Phillips*
Chemical Company LP
The Woodlands, Texas

Before using this product, the user is advised and cautioned to make its own determination and assessment of the safety and suitability of the product for the specific use in question and is further advised against relying on the information contained herein as it may relate to any specific use or application. It is the ultimate responsibility of the user to ensure that the product is suited and the information is applicable to the user's specific application. Chevron Phillips Chemical Company LP does not make, and expressly disclaims, all warranties, including warranties of merchantablity or fitness for a particular purpose, regardless of whether oral or written, express or implied, or allegedly arising from any usage of any trade or from any course of dealing in connection with the use of the information contained herein or the product itself. The user expressly assumes all risk and liability, whether based in contract, tort or otherwise, in connection with the use of the information contained herein or the product itself. Further, information contained herein is given without reference to any intellectual property issues, as well as federal, state or local laws which may be encountered in the use thereof. Such questions should be investigated by the user.

Page 1 of 1

FIG. 7

SALES SPECIFICATION 2

For more information and technical assistance contact:

Chevron Phillips Chemical Company LP
P.O. Box 4910
The Woodlands, TX 77387-4910
800.231.3260

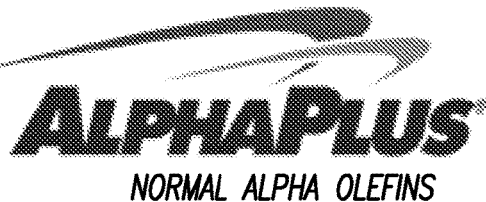

NORMAL ALPHA OLEFINS

AlphaPlus® 1-Tetradecene
Sales Specifications

| Characteristics | Method | Units | Target | Minimum | Maximum | Note |
|---|---|---|---|---|---|---|
| Less than $C_{12}$ | GLC | Wt % | --- | --- | 0.05 | --- |
| $C_{12}$ | GLC | Wt % | --- | --- | 1.00 | --- |
| $C_{14}$ | GLC | Wt % | --- | 98.0 | --- | --- |
| $C_{16}$ | GLC | Wt % | --- | --- | 2.00 | --- |
| Greater than $C_{16}$ | GLC | Wt % | --- | --- | 0.05 | --- |
| n-Alpha Olefin | GLC | Wt % | --- | 93.4 | --- | --- |
| Vinylidene | GLC | Wt % | --- | --- | 5.4 | --- |
| cis-and trans-2-Tetradecene | GLC | Wt % | --- | --- | 0.34 | --- |
| Paraffin | GLC | Wt % | --- | --- | 0.34 | --- |
| Water | ASTM E1064 | PPM by Wt | --- | --- | 100 | --- |
| Color | ASTM D6045 | Saybolt | --- | 30 | --- | --- |
| Appearance | ASTM D4176 | --- | --- | Clear and Bright | --- | --- |
| API Gravity @ 60°F | ASTM D4052 | --- | --- | --- | --- | note 1 |
| Specific Gravity @ 60°F/60°F | ASTM D4052 | --- | --- | --- | --- | note 1 |

1. Run and record

MSDS # 100000067489

Revision Date July 2010

Another quality product from Chevron Phillips Chemical Company LP The Woodlands, Texas Before using this product, the user is advised and cautioned to make its own determination and assessment of the safety and suitability of the product for the specific use in question and is further advised against relying on the information contained herein as it may relate to any specific use or application. It is the ultimate responsibility of the user to ensure that the product is suited and the information is applicable to the user's specific application. Chevron Phillips Chemical Company LP does not make, and expressly disclaims, all warranties, including warranties of merchantablity or fitness for a particular purpose, regardless of whether oral or written, express or implied, or allegedly arising from any usage of any trade or from any course of dealing in connection with the use of the information contained herein or the product itself. The user expressly assumes all risk and liability, whether based in contract, tort or otherwise, in connection with the use of the information contained herein or the product itself. Further, information contained herein is given without reference to any intellectual property issues, as well as federal, state or local laws which may be encountered in the use thereof. Such questions should be investigated by the user.

Page 1 of 1

FIG. 8

SALES SPECIFICATION 3

Shell Chemicals
Technical Data Sheet

NEODENE® 12

Higher Olefins

Issued: November 2015
SICC Product Code: V1142

Description:

NEODENE® 12 Linear Alpha Olefin is high purity 1-dodecene made by the Shell Higher Olefins Process (SHOP) by the oligomerisation of ethylene.

| | Property | Unit | Value | Method |
|---|---|---|---|---|
| TYPICAL CHEMICAL PROPERTIES[a] | C10 and lower | %m/m | < 1 | SMS2895 |
| | C12 | %m/m | > 97 | SMS2895 |
| | C14 and higher | %m/m | < 2 | SMS2895 |
| | Total n-Alpha Olefins | %m/m | > 94.0 | SMS2895 |
| | Branched + Internal Olefins | %m/m | < 6.0 | SMS2895 |
| | Total Paraffins | %m/m | < 0.2 | SMS2895 |
| | Appearance | | CSFVI[b] | Visual |
| | Color, Pt-Co | Pt-Co | < 5 | ASTM D1209 |
| | Carbonyl as C=O | mg/kg | < 15 | SMS2894 |
| | Peroxides as O | mg/kg | < 3.0 | SMS359 |
| | Water | mg/kg | < 100 | ASTM E1064 | a: An official sales specification is available from your local Shell Chemicals representative.
b: Clear & Substantially free of visual impurities www.shell.com/chemicals Shell Global Solutions, One Shell Plaza, 910 Louisiana, Houston, TX 77002-4916, United States of America

FIG. 9A

Technical Data Sheet

| | Property | Unit | Value |
|---|---|---|---|
| Typical Physical Properties[a] | Density @ 20 °C | kg/l | 0.762 |
| | Boiling Point Range | °C | 200-252 |
| | Flashpoint | °C | 83 |
| | Freezing point | °C | -36 |
| | Kinematic viscosity @ 20 °C | mm2/s | 1.8 | a: An official sales specification is available from your local Shell Chemicals representative.

Storage and Handling

NEODENE® Alpha Olefins can be supplied with or without antioxidant as requested. Advice on the storage and handling of NEODENE® Linear Alpha Olefins can be found in the Safety Data Sheet on our website at www.shell.com/chemicals/msds or by contacting your local Shell Chemicals Representative.

Hazard Identification

Alpha Olefins are potentially hazardous material; everyone concerned with handling it must be conversant with the nature of the hazards and trained in the recommended handling procedures for both normal and emergency situations. Before handling the product refer to the Safety Data Sheet that is available on our website at www.shell.com/chemicals/msds or by contacting your local Shell Chemicals Representative.

Emergency Helpline

For emergency telephone numbers refer to the Safety Data Sheet relevant for your company's country and language.

Shell Warranties

NEODENE® is a Shell trademark.

The expression 'Shell Chemicals' refers to the companies of Royal Dutch/Shell Group which are engaged in chemical businesses. Each of the companies which make up the Royal Dutch/Shell Group of companies is an independent entity and has its own separate identity.

The information contained in this publication is to the best of our knowledge, true and accurate, but any recommendations or suggestions that may be made are without guarantee, since the conditions of use are beyond our control. Furthermore, nothing contained herein shall be construed as a recommendation to use any product in conflict with existing patents covering any material or its use.

NEODENE®12                    www.shell.com/chemicals      Page 2

Shell Chemicals, One Shell Plaza, 910 Louisiana, Houston, TX 77002-4916, United States of America

FIG. 9B

INEOS Oligomers — SALES SPECIFICATION 4

*Alpha Olefin C12 (dodecene-1)*
*Sales Specifications*

| Property | Units | Method | Min | Max | Comments |
|---|---|---|---|---|---|
| Carbon Number C10 & lighter | wt% | AAM 5466 | -- | 2 | |
| Carbon Number C12 | wt% | AAM 5466 | 97 | -- | |
| Carbon Number C14 & heavier | wt% | AAM 5466 | -- | 2 | |
| Hydrocarbon Type, Mono-olefin | wt% | AAM 5469 | 99 | -- | 100 minus percent paraffins |
| Hydrocarbon Type, Paraffin | wt% | AAM 5469 | -- | 1 | |
| Olefin Isomers, Linear Terminal | mol% | AAM 5484 | 89 | -- | |
| Olefin Isomers, Branched Terminal | mol% | AAM 5484 | -- | 10 | |
| Olefin Isomers, Linear Internal | mol% | AAM 5484 | -- | 4 | |

Technical information contained herein is furnished without charge or obligation, and is given and accepted at recipient's sole risk. Because conditions of use may vary and are beyond our control, INEOS makes no representation about, and is not responsible or liable for the accuracy or reliability of data, nor for toxicological effects or Industrial Hygiene requirements associated with particular uses of any product described herein. Nothing contained in this document shall be considered a recommendation for any use that may infringe patent rights, or an endorsement of any particular material, equipment, service, or other item not supplied by INEOS. The "Properties" and "Applications" listed in this document are not specifications. They are provided as information only and in no way modify, amend, enlarge, or create any specification or warranty, and ALL WARRANTIES, EXPRESS OR IMPLIED, INCLUDING WITHOUT LIMITATION THE WARRANTIES OF MERCHANTABILITY AND FITNESS FOR A PARTICULAR PURPOSE, ARE EXCLUDED.

The name INEOS is a trademark of INEOS Capital Limited.

FIG. 10

SALES SPECIFICATION 5

Shell Chemicals
Technical Data Sheet

NEODENE® 14

Higher Olefins

Issued: November 2015
SICC Product Code: V1143

Description:

NEODENE® 14 Linear Alpha Olefin is high purity 1-tetradecene made by the Shell Higher Olefins Process (SHOP) by the oligomerisation of ethylene.

| | Property | Unit | Value | Method |
|---|---|---|---|---|
| TYPICAL CHEMICAL PROPERTIES[a] | C12 and lower | %m/m | <2 | SMS2895 |
| | C14 | %m/m | > 95 | SMS2895 |
| | C16 and higher | %m/m | < 3 | SMS2895 |
| | Total n-Alpha Olefins | %m/m | > 93 | SMS2895 |
| | Branched + Internal Olefins | %m/m | < 7.0 | SMS2895 |
| | Total Paraffins | %m/m | < 0.2 | SMS2895 |
| | Appearance | | CSFVI[b] | Visual |
| | Color, Pt-Co | | <5 | ASTM D1209 |
| | Carbonyl as C=O | mg/kg | <15 | SMS2894 |
| | Peroxides as O | mg/kg | <3 | SMS359 |
| | Water | mg/kg | <100 | ASTM E1064 | a: An official sales specification is available from your local Shell Chemicals representative.
b: Clear & Substantially free of visual impurities www.shell.com/chemicals Shell Global Solutions, One Shell Plaza, 910 Louisiana, Houston, TX 77002-4916, United States of America

FIG. 11A

Technical Data Sheet

| Typical Physical Properties | Property | Unit | Value |
|---|---|---|---|
| | Density @ 20°C | kg/l | 0.771 |
| | Boiling Point Range | °C | 214-285 |
| | Flashpoint | °C | 113 |
| | Freezing point | °C | -13 |
| | Kinematic viscosity @ 20°C | mm2/s | 2.7 |

Storage and Handling

NEODENE® Alpha Olefins can be supplied containing antioxidant as requested. Advice on the storage and handling of NEODENE® Linear Alpha Olefins can be found in the Safety Data Sheet on our website at www.shell.com/chemicals/msds or by contacting your local Shell Chemicals Representative.

Hazard Identification

Alpha Olefins are potentially hazardous material; everyone concerned with handling it must be conversant with the nature of the hazards and trained in the recommended handling procedures for both normal and emergency situations. Before handling the product refer to the Safety Data Sheet that is available on our website at www.shell.com/chemicals/msds or by contacting your local Shell Chemicals Representative.

Emergency Helpline

For emergency telephone numbers refer to the Safety Data Sheet relevant for your company's country and language.

Shell Warranties

NEODENE® is a Shell trademark.

The expression 'Shell Chemicals' refers to the companies of Royal Dutch/Shell Group which are engaged in chemical businesses. Each of the companies which make up the Royal Dutch/Shell Group of companies is an independent entity and has its own separate identity.

The information contained in this publication is to the best of our knowledge, true and accurate, but any recommendations or suggestions that may be made are without guarantee, since the conditions of use are beyond our control. Furthermore, nothing contained herein shall be construed as a recommendation to use any product in conflict with existing patents covering any material or its use.

NEODENE®14     www.shell.com/chemicals     Page 2

Shell Chemicals, One Shell Plaza, 910 Louisiana, Houston, TX 77002-4916, United States of America

FIG. 11B

INEOS Oligomers — SALES SPECIFICATION 6

*Alpha Olefin C14 (tetradecene-1)*
*Sales Specifications*

| Property | Units | Method | Min | Max | Comments |
|---|---|---|---|---|---|
| Carbon Number C12 | wt% | AAM 5466 | -- | 3 | |
| Carbon Number C14 | wt% | AAM 5466 | 95 | -- | |
| Carbon Number C16 | wt% | AAM 5466 | -- | 3 | |
| Hydrocarbon Type, Mono-olefin | wt% | AAM 5469 | 99 | -- | 100 minus percent paraffins |
| Hydrocarbon Type, Paraffin | wt% | AAM 5469 | -- | 1 | |
| Olefin Isomers, Linear Terminal | mol% | AAM 5484 | 75 | -- | |

Technical information contained herein is furnished without charge or obligation, and is given and accepted at recipient's sole risk. Because conditions of use may vary and are beyond our control, INEOS makes no representation about, and is not responsible or liable for the accuracy or reliability of data, nor for toxicological effects or Industrial Hygiene requirements associated with particular uses of any product described herein. Nothing contained in this document shall be considered a recommendation for any use that may infringe patent rights, or an endorsement of any particular material, equipment, service, or other item not supplied by INEOS. The "Properties" and "Applications" listed in this document are not specifications. They are provided as information only and in no way modify, amend, enlarge, or create any specification or warranty, and ALL WARRANTIES, EXPRESS OR IMPLIED, INCLUDING WITHOUT LIMITATION THE WARRANTIES OF MERCHANTABILITY AND FITNESS FOR A PARTICULAR PURPOSE, ARE EXCLUDED.

The name INEOS is a trademark of INEOS Capital Limited.

FIG. 12

COMPOSITION COMPRISING BRANCHED ALDEHYDES

CROSS-REFERENCE TO RELATED APPLICATIONS

This patent application is a US nonprovisional application of and claims benefit of the filing date of U.S. provisional patent application No. 63/126,780 titled "Branched Products" filed 17 Dec. 2020.

This patent application is a US nonprovisional application of and claims benefit of the filing date of U.S. provisional patent application No. 63/035,479 titled "Branched Alcohols" filed 5 Jun. 2020.

This patent application is a US nonprovisional application of and claims benefit of the filing date of U.S. provisional patent application No. 63/035,073 titled "Alcohols Production" filed 5 Jun. 2020.

This patent application is a US nonprovisional application of and claims benefit of the filing date of U.S. provisional patent application No. 63/035,280 titled "Branched Compounds" filed 5 Jun. 2020.

This patent application is a US nonprovisional continuation-in-part application of and claims benefit of the filing date of copending U.S. nonprovisional patent application Ser. No. 17/246,580 titled "Alcohols Production" filed 30 Apr. 2021, which issued as U.S. Pat. No. 11,680,032 on Jun. 20, 2023, and which claims benefit of the filing date of U.S. provisional patent application No. 63/035,073 titled "Alcohols Production" filed 5 Jun. 2020.

This patent application is a US nonprovisional continuation-in-part application of and claims benefit of the filing date of copending PCT Application number PCT/US2021/030341 (PCT/US21/30341) titled "Alcohols Production" filed 30 Apr. 2021 which claims benefit of the filing date of U.S. provisional patent application No. 63/035,073 titled "Alcohols Production" filed 5 Jun. 2020.

This patent application is a US nonprovisional continuation-in-part application of and claims benefit of the filing date of copending U.S. nonprovisional patent application Ser. No. 17/331,371 titled "Branched Compounds" filed 26 May 2021 which claims benefit of priority to each of the following: 63/035,280 titled "Branched Compounds" filed 5 Jun. 2020; 63/035,479 titled "Branched Alcohols" filed 5 Jun. 2020; 63/035,073 titled "Alcohols Production" filed 5 Jun. 2020; 63/126,780 titled "Branched Products" filed 17 Dec. 2020; Ser. No. 17/246,580 titled "Alcohols Production" filed 30 Apr. 2021, which issued as U.S. Pat. No. 11,680,032 on Jun. 20, 2023, and which also claims benefit to 63/035,073 titled "Alcohols Production" filed 5 Jun. 2020; PCT/US2021/030341 titled "Alcohols Production" filed 30 Apr. 2021 which also claims benefit to 63/035,073 titled "Alcohols Production" filed 5 Jun. 2020.

This patent application is a US nonprovisional continuation-in-part application of and claims benefit of the filing date of copending PCT Application number PCT/US2021/034189 titled "Branched Compounds" filed 26 May 2021 which claims benefit of priority to each of the following: 63/035,280 titled "Branched Compounds" filed 5 Jun. 2020; 63/035,479 titled "Branched Alcohols" filed 5 Jun. 2020; 63/035,073 titled "Alcohols Production" filed 5 Jun. 2020; 63/126,780 titled "Branched Products" filed 17 Dec. 2020; Ser. No. 17/246,580 titled "Alcohols Production" filed 30 Apr. 2021, which issued as U.S. Pat. No. 11,680,032 on Jun. 20, 2023, and which also claims benefit of priority to 63/035,073 titled "Alcohols Production" filed 5 Jun. 2020; PCT/US2021/030341 titled "Alcohols Production" filed 30 Apr. 2021; which also claims benefit of priority to 63/035,073 titled "Alcohols Production" filed 5 Jun. 2020.

This patent application is a US nonprovisional continuation-in-part application of and claims benefit of the filing date of copending U.S. nonprovisional application Ser. No. 17/336,099 titled "Branched Alcohols" filed 1 Jun. 2021, which issued as U.S. Pat. No. 12,054,455 on Aug. 6, 2024, and which claims benefit of each of the following: 63/035,479 titled "Branched Alcohols" filed 5 Jun. 2020; 63/035,073 titled "Alcohols Production" filed 5 Jun. 2020; 63/035,280 titled "Branched Compounds" filed 5 Jun. 2020; 63/126,780 titled "Branched Products" filed 17 Dec. 2020; Ser. No. 17/246,580 titled "Alcohols Production" filed 30 Apr. 2021 which issued as U.S. Pat. No. 11,680,032 on Jun. 20, 2023, which also claims benefit of the filing date of U.S. provisional patent application No. 63/035,073 titled "Alcohols Production" filed 5 Jun. 2020; PCT/US2021/030341 titled "Alcohols Production" filed 30 Apr. 2021 which also claims benefit of the filing date of copending U.S. provisional patent application No. 63/035,073 titled "Alcohols Production" filed 5 Jun. 2020.

This patent application is a US nonprovisional continuation-in-part application of and claims benefit of the filing date of copending U.S. nonprovisional application Ser. No. 17/336,099 titled "Branched Alcohols" filed 1 Jun. 2021, which issued as U.S. Pat. No. 12,054,455 on Aug. 6, 2024, and which claims benefit of Ser. No. 17/331,371 titled "Branched Compounds" filed 26 May 2021 which claims benefit of priority to each of the following: 63/035,280 titled "Branched Compounds" filed 5 Jun. 2020; 63/035,479 titled "Branched Alcohols" filed 5 Jun. 2020; 63/035,073 titled "Alcohols Production" filed 5 Jun. 2020; 63/126,780 titled "Branched Products" filed 17 Dec. 2020; Ser. No. 17/246,580 titled "Alcohols Production" filed 30 Apr. 2021, which issued as U.S. Pat. No. 11,680,032 on Jun. 20, 2023, and which also claims benefit to 63/035,073 titled "Alcohols Production" filed 5 Jun. 2020; PCT/US2021/030341 titled "Alcohols Production" filed 30 Apr. 2021 which also claims benefit to 63/035,073 titled "Alcohols Production" filed 5 Jun. 2020.

This patent application is a US nonprovisional continuation-in-part application of and claims benefit of the filing date of copending U.S. nonprovisional application Ser. No. 17/336,099 titled "Branched Alcohols" filed 1 Jun. 2021, which issued as U.S. Pat. No. 12,054,455 on Aug. 6, 2024, and which claims benefit of PCT/US2021/034189 titled "Branched Compounds" filed 26 May 2021 which claims benefit of priority to each of the following: 63/035,280 titled "Branched Compounds" filed 5 Jun. 2020; 63/035,479 titled "Branched Alcohols" filed 5 Jun. 2020; 63/035,073 titled "Alcohols Production" filed 5 Jun. 2020; 63/126,780 titled "Branched Products" filed 17 Dec. 2020; Ser. No. 17/246,580 titled "Alcohols Production" filed 30 Apr. 2021, which issued as U.S. Pat. No. 11,680,032 on Jun. 20, 2023, and which also claims benefit to 63/035,073 titled "Alcohols Production" filed 5 Jun. 2020; PCT/US2021/030341 titled "Alcohols Production" filed 30 Apr. 2021 which also claims benefit to 63/035,073 titled "Alcohols Production" filed 5 Jun. 2020.

This patent application is a US nonprovisional continuation-in-part application of and claims benefit of the filing date of copending PCT Application number PCT/US2021/035169 titled "Branched Alcohols" filed 1 Jun. 2021, which claims benefit of each of the following: 63/035,479 titled "Branched Alcohols" filed 5 Jun. 2020; 63/035,073 titled "Alcohols Production" filed 5 Jun. 2020; 63/035,280 titled "Branched Compounds" filed 5 Jun. 2020; 63/126,780 titled "Branched Products" filed 17 Dec. 2020; Ser. No. 17/246,580 titled "Alcohols Production" filed 30 Apr. 2021, which issued as U.S. Pat. No. 11,680,032 on Jun. 20, 2023, and which claims benefit of the filing date of U.S. provisional patent application No. 63/035,073 titled "Alcohols Production" filed 5 Jun. 2020; PCT/US2021/030341 titled "Alcohols Production" filed 30 Apr. 2021 which claims benefit of the filing date of U.S. provisional patent application No. 63/035,073 titled "Alcohols Production" filed 5 Jun. 2020.

This patent application is a US nonprovisional continuation-in-part application of and claims benefit of the filing date of copending PCT Application number PCT/US2021/035169 titled "Branched Alcohols" filed 1 Jun. 2021 which claims benefit of Ser. No. 17/331,371 titled "Branched Compounds" filed 26 May 2021 which claims benefit of priority to each of the following: 63/035,280 titled "Branched Compounds" filed 5 Jun. 2020; 63/035,479 titled "Branched Alcohols" filed 5 Jun. 2020; 63/035,073 titled "Alcohols Production" filed 5 Jun. 2020; 63/126,780 titled "Branched Products" filed 17 Dec. 2020; Ser. No. 17/246,580 titled "Alcohols Production" filed 30 Apr. 2021, which issued as U.S. Pat. No. 11,680,032 on Jun. 20, 2023, and which also claims benefit to 63/035,073 titled "Alcohols Production" filed 5 Jun. 2020; PCT/US2021/030341 titled "Alcohols Production" filed 30 Apr. 2021 which also claims benefit to 63/035,073 titled "Alcohols Production" filed 5 Jun. 2020.

This patent application is a US nonprovisional continuation-in-part application of and claims benefit of the filing date of copending PCT Application number PCT/US2021/035169 titled "Branched Alcohols" filed 1 Jun. 2021 which claims benefit of PCT/US2021/034189 titled "Branched Compounds" filed 26 May 2021 which claims benefit of priority to each of the following: 63/035,280 titled "Branched Compounds" filed 5 Jun. 2020; 63/035,479 titled "Branched Alcohols" filed 5 Jun. 2020; 63/035,073 titled "Alcohols Production" filed 5 Jun. 2020; 63/126,780 titled "Branched Products" filed 17 Dec. 2020; Ser. No. 17/246,580 titled "Alcohols Production" filed 30 Apr. 2021, which issued as U.S. Pat. No. 11,680,032 on Jun. 20, 2023, and which also claims benefit to 63/035,073 titled "Alcohols Production" filed 5 Jun. 2020; PCT/US2021/030341 titled "Alcohols Production" filed 30 Apr. 2021 which also claims benefit to 63/035,073 titled "Alcohols Production" filed 5 Jun. 2020.

Thus, this nonprovisional application claims priority to 5 Jun. 2020 through each of the following patent applications: 63/035,280 titled "Branched Compounds", 63/035,479 titled "Branched Alcohols"; 63/035,073 titled "Alcohols Production"; PCT/US2021/030341 titled "Alcohols Production"; Ser. No. 17/246,580 titled "Alcohols Production"; Ser. No. 17/331,371 titled "Branched Compounds", which issued as U.S. Pat. No. 11,680,032 on Jun. 20, 2023, and PCT/US2021/034189 titled "Branched Compounds"; Ser. No. 17/336,099 titled "Branched Alcohols" filed 1 Jun. 2021, which issued as U.S. Pat. No. 12,054,455 on Aug. 6, 2024, and PCT/US2021/035169 titled "Branched Alcohols" filed 1 Jun. 2021.

Thus, this nonprovisional application claims priority to 17 Dec. 2020 through provisional patent application 63/126,780 titled "Branched Products"; Ser. No. 17/331,371 titled "Branched Compounds" and PCT/US2021/034189 titled "Branched Compounds" Ser. No. 17/336,099 titled "Branched Alcohols" filed 1 Jun. 2021, which issued as U.S. Pat. No. 12,054,455 on Aug. 6, 2024, and PCT/US2021/035169 titled "Branched Alcohols" filed 1 Jun. 2021.

Thus, this nonprovisional application claims priority to 30 Apr. 2021 through each of the following nonprovisional applications: Ser. No. 17/246,580 titled "Alcohols Production", which issued as U.S. Pat. No. 11,680,032 on Jun. 20, 2023, and PCT/US2021/030341 titled "Alcohols Production", Ser. No. 17/331,371 titled "Branched Compounds" and PCT/US2021/034189 titled "Branched Compounds"; Ser. No. 17/336,099 titled "Branched Alcohols" filed 1 Jun. 2021, which issued as U.S. Pat. No. 12,054,455 on Aug. 6, 2024, and PCT/US2021/035169 titled "Branched Alcohols" filed 1 Jun. 2021.

Thus, this nonprovisional application claims priority to 26 May 2021 through each of the following nonprovisional applications: Ser. No. 17/331,371 titled "Branched Compounds" and PCT/US2021/034189 titled "Branched Compounds"; Ser. No. 17/336,099 titled "Branched Alcohols" filed 1 Jun. 2021 , which issued as U.S. Pat. No. 12,054,455 on Aug. 6, 2024, and PCT/US2021/035169 titled "Branched Alcohols" filed 1 Jun. 2021.

Thus, this nonprovisional application claims priority to 1 Jun. 2021 through each of the following nonprovisional applications: Ser. No. 17/336,099 titled "Branched Alcohols" filed 1 Jun. 2021 , which issued as U.S. Pat. No. 12,054,455 on Aug. 6, 2024, and PCT/US2021/035169 titled "Branched Alcohols" filed 1 Jun. 2021.

INCORPORATION BY REFERENCE

This patent application incorporates by reference in its entirety copending U.S. provisional patent application No. 63/035,280 titled "Branched Compounds" filed 5 Jun. 2020.

This patent application incorporates by reference in its entirety copending U.S. provisional patent application No. 63/035,479 titled "Branched Alcohols" filed 5 Jun. 2020.

This patent application incorporates by reference in its entirety copending U.S. provisional patent application No. 63/035,073 titled "Alcohols Production" filed 5 Jun. 2020.

This patent application incorporates by reference in its entirety copending U.S. provisional patent application No. 63/126,780 titled "Branched Products" filed 17 Dec. 2020.

This patent application incorporates by reference in its entirety copending U.S. nonprovisional patent application Ser. No. 17/246,580 titled "Alcohols Production" filed 30 Apr. 2021, which issued as U.S. Pat. No. 11,680,032 on Jun. 20, 2023.

This patent application incorporates by reference in its entirety copending PCT Application number PCT/US2021/030341 titled "Alcohols Production" filed 30 Apr. 2021.

This patent application incorporates by reference in its entirety copending US nonprovisional patent application number Ser. No. 17/331,371 titled "Branched Compounds" filed 26 May 2021.

This patent application incorporates by reference in its entirety copending PCT Application number PCT/US2021/034189 titled "Branched Compounds" filed 26 May 2021.

This patent application incorporates by reference in its entirety copending U.S. nonprovisional patent application Ser. No. 17/336,099 titled "Branched Alcohols" filed 1 Jun. 2021, which issued as U.S. Pat. No. 12,054,455 on Aug. 6, 2024.

This patent application incorporates by reference in its entirety copending PCT Application number PCT/US2021/035169 titled "Branched Alcohols" filed 1 Jun. 2021.

FIELD OF THE INVENTION

The present invention relates to branched aldehydes and branched alcohols and methods for producing and manufacturing one or more branched products.

BACKGROUND OF THE INVENTION

The chemical industry has suffered a long felt need to produce branched aldehydes, branched alcohols and branched products derived from branched aldehydes and branched alcohols in a cost-effective manner. There is a ready and large supply of alpha olefins which are inexpensive. However, there is no known way to efficiently and cost effectively produce branched aldehydes, branched alcohols and branched products on an industrial scale using alpha olefins as a feedstock.

SUMMARY OF THE INVENTION

There is a ready and large supply of alpha olefins globally which are inexpensive. Alpha olefins are typically produced from economically priced ethylene via ethylene oligomerization processes. However, it is a significant problem that these alpha olefins are largely linear in nature and there is no known way to efficiently and cost effectively produce branched products from these linear alpha olefins. Specifically, there is no known way to efficiently produce valuable products such as branched aldehydes, branched alcohols and other branched products on an industrial scale using alpha olefins as a feedstock. The various embodiments herein can produce multiple branched aldehyde products simultaneously from alpha olefin feedstocks. In embodiments herein multiple branched alcohol products can be produced simultaneously from alpha olefin feedstocks.

It is well known that alpha olefins can be hydroformylated to produce aldehyde products. However, these products are predominately linear in nature because the olefin function (i.e. double bond) is in the alpha position (i.e. between the first and second carbons) which leads to linear aldehyde products. For example, the hydroformylation of the C12 alpha olefin 1-Dodecene produces a C13 aldehyde product consisting essentially of the linear aldehyde 1-Tridecanal. In order to produce branched products, it is necessary as a first step to accomplish the isomerization of the olefin function from the alpha position to an internal olefin position before as a second step to hydroformylate the olefins to aldehydes. In this manner, a two-step process of first isomerization and secondly hydroformylation can produce branched aldehyde products from linear alpha olefin starting feedstocks. It is very advantageous that both the isomerization step and the hydroformylation step utilize the same catalyst such that this two-step process can be carried out in an efficient and economical manner. The branched aldehydes produced via this two-step process from alpha olefins will largely be "2-alkyl" branched aldehydes wherein the branching occurs at the second carbon from the aldehyde function. From these 2-alkyl branched aldehydes, it is then possible via hydrogenation to efficiently produced 2-alkyl branched alcohols products, and via further reactions produce other 2-alkyl derivatives such as surfactants. The position of the alkyl branching in these products as well as the length of the alkyl branches are known to be important to final product properties.

In an embodiment, a two-step process is disclosed herein that produces greater than 20% branched aldehyde products, with 25% to 98+% branching, that are produced from an alpha olefin feedstock. Additionally, the two-step process disclosed herein employs a rhodium organophosphorous catalyst for both the first step which is an isomerization reaction step and the second step which is a hydroformylation reaction step. In an embodiment, the two-step process disclosed herein employs a cobalt organophosphorous catalyst for both the first step which is an isomerization reaction step and the second step which is a hydroformylation reaction step. In an embodiment, the two-step process disclosed herein employs a mixed cobalt-rhodium organophosphorous catalyst for both the first step which is an isomerization reaction step and the second step which is a hydroformylation reaction step.

In an embodiment, an embodiment of the methods disclosed herein can be a process having a first process step and a second process step. The first process step can be a reaction isomerizing an alpha olefin under a Carbon Monoxide (CO) and Hydrogen (H2) (herein also as "CO/H2") atmosphere at a first pressure. The isomerizing step can be catalyzed by a first catalyst comprising an organometallic complex of rhodium and one type of an organophosphorus ligand or an organometallic complex of rhodium and more than one type of an organophosphorus ligand, said isomerizing producing an isomerized olefin. The second step of this embodiment can be a reaction hydroformylating the isomerized olefin under a CO/H2 atmosphere at a second pressure higher than said first pressure. The hydroformylating step can be catalyzed by the first catalyst and said hydroformylating step can produce a branched aldehyde.

In an embodiment, the catalyst used in the isomerizing step can be the same catalyst as in the hydroformylating step. In an embodiment the second pressure can be lower than the first pressure. In another embodiment, the first pressure and second pressure are different. Thus, optionally the second pressure can be either higher or lower than the first pressure.

In an embodiment, the organophosphorous ligand can be a phosphine. In a nonlimiting example of a phosphine ligand, the phosphine ligand can be triphenylphosphine. In another embodiment, the organophosphorous ligand can be a phosphite. In a nonlimiting example of a phosphite ligand, the phosphite ligand can be tris (2,4-di-t-butylphenyl) phosphite. In yet another embodiment, a mixture of organophosphorous ligands of different types can be used, such as a mixture of a phosphine and a phosphite. In a nonlimiting example of a mixture of organophosphorous ligands, the organophosphorous ligands can be a mixture of triphenylphosphine and tris (2,4-di-t-butylphenyl) phosphite. In an embodiment, the alpha olefin can be a C4-C36 alpha olefin. In an embodiment, the first catalyst can be formed when the molar ratio of phosphorous to rhodium is in a range of 1:1 to 1000:1.

In an embodiment, the molar ratio of CO to H2 in the isomerizing step can be in a range of 10:1 to 1:10. In an embodiment, the molar ratio of CO to H2 in the hydrofomylating step can be in a range of 10:1 to 1:10. In an embodiment, the molar ratio of CO to 112 in the isomerizing step can be the same as the molar ratio of CO to H2 in the hydrofomylating step. In an embodiment, the molar ratio of CO to H2 in the isomerizing step can be different than the molar ratio of CO to 1-12 in the hydrofomylating step.

In an embodiment, the alpha olefin can comprise at least one of a short chain alpha olefin, a medium chain alpha olefin and a long chain alpha olefin. In an embodiment, the alpha olefin can comprise at least one of a C4 or greater alpha olefin. In an embodiment, the alpha olefin can comprise at least one of a C4 or greater alpha olefin, a C6 or greater alpha olefin, a C10 or greater alpha olefin, a C16 or greater alpha olefin, a C20 or greater alpha olefin, and a C30 or greater alpha olefin and a C36 or greater alpha olefin.

In an embodiment, the isomerizing produces a reaction product comprising an isomerized olefin which comprises a 20 wt. % or greater isomerized olefin.

In an embodiment, said isomerizing step produces a reaction product comprising a 5 wt. % or greater isomerized olefin, or a 10 wt. % or greater isomerized olefin, or a 15 wt. % or greater isomerized olefin, or a 20 wt. % or greater isomerized olefin, or a 30 wt. % or greater isomerized olefin, or a 40 wt. % or greater isomerized olefin, or a 50 wt. % or greater isomerized olefin, or a 60 wt. % or greater isomerized olefin, or a 70 wt. % or greater isomerized olefin, or a 80 wt. % or greater isomerized olefin, or a 90 wt. % or greater isomerized olefin, or a 95 wt. % or greater isomerized olefin, or a 99 wt. % or greater isomerized olefin.

In an embodiment, said hydroformylating step produces a reaction product comprising a 25 wt. % or greater branched aldehyde, or a 30 wt. % or greater branched aldehyde, or a 40 wt. % or greater branched aldehyde, or a 50 wt. % or greater branched aldehyde, or a 60 wt. % or greater branched aldehyde, or a 70 wt. % or greater branched aldehyde, or a 80 wt. % or greater branched aldehyde, or a 90 wt. % or greater branched aldehyde, or a 95 wt. % or greater branched aldehyde, or a 99 wt. % or greater branched aldehyde.

In an embodiment, a process can have the steps of: providing a first catalyst which is an organometallic complex of rhodium and one type of an organophosphorus ligand or an organometallic complex of rhodium and more than one type of an organophosphorus ligand; activating said first catalyst with CO to achieve an activated first catalyst; isomerizing an alpha olefin by said activated first catalyst at a first pressure to produce an isomerized olefin; providing hydrogen; hydroformylating said isomerized olefin by reaction with CO and H2 at a second pressure to produce a branched aldehyde. In an embodiment, the isomerizing step occurs in an atmosphere having a molar percentage of CO of 10%-100% and a molar percentage of hydrogen of 0%-90%. In an embodiment, the isomerizing step occurs in an atmosphere comprising both CO and H2. In an embodiment, the molar ratio of CO to H2 in the isomerizing step can be in a range of 10:1 to 1:10. In an embodiment, the molar ratio of CO to H2 in the hydroformylating step can be in a range of 10:1 to 1:10. In an embodiment, the alpha olefin is a linear alpha olefin having a number of carbons in the range of C4-C36. In an embodiment, the alpha olefin can be a C4-C36 alpha olefin. In an embodiment, the organophosphorous ligand can be a phosphine. In a nonlimiting example of a phosphine ligand, the phosphine ligand can be triphenylphosphine. In another embodiment, the organophosphorous ligand can be a phosphite. In a nonlimiting example of a phosphite ligand, the phosphite ligand can be tris (2,4-di-t-butylphenyl) phosphite. In yet another embodiment, a mixture of organophosphorous ligands of different types can be used, such as a mixture of a phosphine and a phosphite. In a nonlimiting example of a mixture of organophosphorous ligands, the organophosphorous ligands can be a mixture of triphenylphosphine and tris (2,4-di-t-butylphenyl) phosphite. In an embodiment, the first catalyst can be formed when the molar ratio of phosphorous to rhodium is in a range of 1:1 to 1000:1.

In an embodiment, a process can have the steps of: providing CO and H2; providing a first catalyst which is an organometallic complex of rhodium and one type of an organophosphorus ligand or an organometallic complex of rhodium and more than one type of an organophosphorus ligand; providing a linear alpha olefin; isomerizing said linear alpha olefin (also herein described as a normal alpha olefin) by said first catalyst in the presence of CO and H2 at a first pressure to produce an isomerized olefin; and hydroformylating said isomerized olefin by said first catalyst in the presence of CO and 112 at a second pressure different from said first pressure to produce a branched aldehyde. In an embodiment, the branched aldehyde is a 2-alkyl branched aldehyde. In an embodiment, the linear alpha olefin is a C4-C36 linear alpha olefin. In an embodiment, the branched aldehyde produced from the C4-C36 linear alpha olefin is a C5-C37 branched aldehyde. In an embodiment, the linear alpha olefin can be 1-Butene and said branched aldehyde can be branched Pentanals. In an embodiment, the linear alpha olefin can be 1-Hexene and said branched aldehyde can be branched Heptanals. In an embodiment, the linear alpha olefin can be 1-Octene and said branched aldehyde can be branched Nonanals. In an embodiment, the linear alpha olefin can be 1-Decene and said branched aldehyde can be branched Undecanals. In an embodiment, the linear alpha olefin can be 1-Dodecene and said branched aldehyde can be branched Tridecanals. In an embodiment, the linear alpha olefin can be 1-Tetradecene and said branched aldehyde can be branched Pentadecanals.

In an embodiment, the linear alpha olefin can be 1-Hexadecene and said branched aldehyde can be branched Heptadecanals. In an embodiment, the linear alpha olefin can be 1-Octadecene and said branched aldehyde can be branched Nonadecanals. In an embodiment, the organophosphorous ligand can be a phosphine. In a nonlimiting example of a phosphine ligand, the phosphine ligand can be triphenylphosphine. In another embodiment, the organophosphorous ligand can be a phosphite. In a nonlimiting example of a phosphite ligand, the phosphite ligand can be tris (2,4-di-t-butylphenyl) phosphite. In yet another embodiment, a mixture of organophosphorous ligands of different types can be used, such as a mixture of a phosphine and a phosphite. In a nonlimiting example of a mixture of organophosphorous ligands, the organophosphorous ligands can be a mixture of triphenylphosphine and tris (2,4-di-t-butylphenyl) phosphite.

In an embodiment, the first catalyst is formed when the molar ratio of phosphorous to rhodium is in a range of 1:1 to 1000:1. In an embodiment, the first catalyst is formed when the molar ratio of phosphorous to rhodium is in a range of 1:1 to 1000:1 in the isomerization step and/or reactor. In an embodiment, the first catalyst is formed when the molar ratio of phosphorous to rhodium is in a range of 1:1 to 1000:1 in the hydroformylation step and/or reactor.

In an embodiment, a process can have the steps of: providing CO and H2; providing a first catalyst which is an organometallic complex of rhodium and one type of an organophosphorus ligand or an organometallic complex of rhodium and more than one type of an organophosphorus ligand; providing an alpha olefin; isomerizing said alpha olefin by said first catalyst in the presence of CO and H2 at a first pressure to produce an isomerized olefin; and hydroformylating said isomerized olefin by said first catalyst in the presence of CO and H2 at a second pressure different from said first pressure to produce a branched aldehyde. In an embodiment, the alpha olefin can be a C4-C36 alpha olefin. In an embodiment, the organophosphorous ligand can be a phosphine. In a nonlimiting example of a phosphine ligand, the phosphine ligand can be triphenylphosphine. In another embodiment, the organophosphorous ligand can be a phosphite. In a nonlimiting example of a phosphite ligand, the phosphite ligand can be tris (2,4-di-t-butylphenyl) phosphite. In yet another embodiment, a mixture of organophosphorous ligands of different types can be used, such as a mixture of a phosphine and a phosphite. In a nonlimiting example of a mixture of organophosphorous ligands, the organophosphorous ligands can be a mixture of triphenylphosphine and tris (2,4-di-t-butylphenyl) phosphite. In an embodiment, the first catalyst can be formed when the molar ratio of phosphorous to rhodium is in a range of 1:1 to 1000:1.

In an embodiment, a process can have the steps of: providing CO and H2; providing a first catalyst which is an organometallic complex of rhodium and one type of an organophosphorus ligand or an organometallic complex of rhodium and more than one type of an organophosphorus ligand; providing an alpha olefin; isomerizing said alpha olefin by said first catalyst in the presence of CO and H2 at a first pressure to produce an isomerized olefin; and hydroformylating said isomerized olefin by said first catalyst in the presence of CO and H2 at a second pressure different from said first pressure to produce a branched aldehyde; and hydrogenating said branched aldehyde to produce a branched alcohol. In an embodiment, the isomerizing step produces a reaction product comprising 5 wt. % or greater isomerized olefins, or 10 wt. % or greater isomerized olefins, or 20 wt. % or greater isomerized olefins, or 40 wt. % or greater isomerized olefins. In an embodiment, the hydroformylating step produces a reaction product comprising 25 wt. % or greater branched aldehydes, or 50 wt. % or greater branched aldehydes. In an embodiment, the hydrogenating step produces a reaction product comprising 25 wt. % or greater branched alcohols, or 50 wt. % or greater branched alcohols.

In an embodiment a process for producing a branched aldehyde can have the steps of: providing an alpha olefin; providing a first catalyst; isomerizing said alkene catalyzed by said first catalyst under an atmosphere comprising a CO and an H2 at a first pressure; producing an intermediate isomerized olefin product composition having internal olefins; hydroformylating said intermediate isomerized olefin product catalyzed by said first catalyst under an atmosphere comprising a CO and an $H_2$ at a second pressure higher than said first pressure; and producing a branched aldehyde product. In an embodiment, this process can also have the step of separating said branched aldehyde product from the first catalyst stream via a distillation process. In an embodiment, this process can also have the steps of: hydrogenating said branched aldehyde in the presence of a hydrogenation catalyst; and producing a branched alcohols product composition. In an embodiment, the alpha olefin is a C4 to C36, or greater, alpha olefin. In an embodiment, the catalyst is a rhodium catalyst. In an embodiment, the catalyst is a homogeneous rhodium catalyst. In an embodiment, the catalyst is a homogeneous rhodium catalyst having an organophosphorous ligand. In an embodiment, the first pressure can be in a range of 0.01 bar(absolute) to 20 bar(absolute) (which in gauge units is a range of −0.99 bar(g) (a negative value, vacuum) to 19 bar(g)). In an embodiment, the intermediate isomerized olefin product can comprise at least 10 wt. % of internal olefins, or at least 20 wt. % of internal olefins. In an embodiment, the second pressure can be in a range of from 1 bar(g) to 400 bar(g). the branched aldehyde product comprises at least 25 wt. % of branched aldehydes:

In an embodiment, a process can have the steps of: providing CO and H2; providing a first catalyst which is an organometallic complex of rhodium and one type of an organophosphorus ligand or an organometallic complex of rhodium and more than one type of an organophosphorus ligand; providing an alpha olefin; isomerizing said alpha olefin by said first catalyst in the presence of CO and H2 at a first pressure to produce an isomerized olefin; hydroformylating said isomerized olefin by said first catalyst in the presence of CO and H2 at a second pressure different from said first pressure to produce a branched aldehyde; hydrogenating said branched aldehyde to produce a branched alcohol; and producing a branched surfactant from said branched alcohol. In an embodiment, the producing step comprises sulfating the branched alcohol to produce a branched alcohol sulfate. In an embodiment, the producing step comprises alkoxylating the branched alcohol to produce a branched alkoxylated alcohol. In an embodiment, the alkoxylating agent can be ethylene oxide, propylene oxide or mixtures of ethylene oxide and propylene oxide. In an embodiment, the alkoxylating agent can be ethylene oxide and propylene oxide, added simultaneously or step-wise (i.e. block oxide). In an embodiment, the alkoxylating agent can be ethylene oxide, propylene oxide, butylene oxide and mixtures of ethylene oxide, propylene oxide and butylene oxide. In an embodiment, the alkoxylated alcohol can be sulfated to produce a branched sulfated alkoxylated alcohol. In an embodiment, the isomerizing step can produce a reaction product comprising 20 wt. % or greater internal olefins. In an embodiment, the isomerizing can produce a reaction product comprising 50 wt. % or greater internal olefins. In an embodiment, the hydroformylating can produce a reaction product comprising 25 wt. % or greater branched aldehydes. In an embodiment, the hydroformylating can produce a reaction product comprising 50 wt % or greater branched aldehydes. In an embodiment, the hydrogenating can produce a reaction product comprising 40 wt. % or greater branched alcohols. In an embodiment, the hydrogenating step can produce a reaction product comprising 50 wt. % or greater branched alcohols. In an embodiment, the said surfactant can have 40 wt. % or greater branched surfactants. In an embodiment, the surfactant can have 50 wt. % or greater branched surfactants.

Downstream Products of Branched Alcohols

The branched alcohols products produced by the processes in their varied embodiments disclosed herein can be used to produce myriad different products.

In embodiments, the branched alcohol products of the processes disclosed herein can be used to produce fuel and lubricant additives, food additives, solvents, emulsifiers, emollients, thickeners, coatings, elastomers, adhesives, antioxidants, polymer stabilizers, cosmetics.

Carboxylation Products

In embodiments, the branched alcohol products of the processes disclosed herein can be carboxylated by reaction with carboxylic acids, dicarboxylic acids or polyacids to produce esters. Applications for such esters produced by the processes disclosed herein can be lubricants, plasticizers, solvents, coatings, inks, cleaners, binders, paint strippers and/or oilfield chemicals.

Branched Aldehyde, Amine & Carboxylic Products

In various embodiments, numerous downstream products can be manufactured as products of the processes disclosed herein. The branched aldehydes produced by the embodiments herein can be reacted to produce a number of branched aldehyde products. The branched aldehydes can be further reacted to produce branched amine products. In other embodiments the branched aldehydes can be reacted to produce branched carboxylic acid products.

Branched Aldehyde Products

In an embodiment, branched aldehyde products of the processes disclosed herein can be for example, but not limited to, fragrance molecules, flavoring agents, solvents, intermediates in the manufacture of plastics, dyes, and pharmaceuticals.

In an embodiment, the branched aldehydes produced by the processes disclosed herein can be reacted with ammonia and hydrogen to produce primary branched amines.

In an embodiment, the branched aldehydes produced by the processes disclosed herein can be reacted with amines and hydrogen to produce secondary branched amines.

In an embodiment, the branched aldehydes produced by the processes disclosed herein can be reacted with secondary amines to produce tertiary branched amines.

Branched Amine Products

In embodiments, the branched amine products of the processes disclosed herein can be for example, but not limited to, chemical catalysts, corrosion inhibitors, emulsifiers, flotation aids, ion exchange resins, rubber chemicals, antioxidants, stabilizers, antistatic agents, plasticizers, dyes, gasoline and lubricant additives, hardeners for epoxy resins, solvents, metal extraction, photographic developers and anticaking agents.

In embodiments, the branched amine products of the processes disclosed herein can be intermediates for the synthesis of pharmaceuticals, herbicides, fungicides and insecticides.

In an embodiment, the branched amine products of the processes disclosed herein can be alkoxylated to produce alkoxylated amine surfactants.

In an embodiment, the branched amine products of the embodiments of the processes disclosed herein can be oxidized to produce amine oxide surfactants.

Branched Carboxylic Acid Products

In an embodiment, the branched aldehyde products of the processes disclosed herein can be oxidized with oxygen or other oxidizing agents to produce branched carboxylic acids.

In embodiments, the branched carboxylic acid products of the processes disclosed herein can be corrosion inhibitors, emulsifiers, ion exchange resins, food additives, fragrance molecules, plastic additives, lubricants, solvents, coatings, dyes, rubber chemicals, plasticizers.

In an embodiment, a method can have the steps of: providing a feed having an alpha olefin; providing a catalyst; catalyzing an isomerization of said alpha olefin by said catalyst; producing an isomerized olefin by said isomerization of said alpha olefin; catalyzing a hydroformylation of said isomerized olefin by said catalyst; and producing a branched aldehyde by said hydroformylation of said isomerized olefin. In an embodiment, this method can also have the steps of: reacting said branched aldehyde with hydrogen; and producing a branched alcohol by said reacting said branched aldehyde.

In an embodiment, this method can also have the step of: providing said feed having one or more internal olefins. In an embodiment, this method can also have the step of: providing said feed having one or more internal olefins which are C4 to C36 internal olefins. In an embodiment, a method can have the steps of: providing a feed having one or more internal olefins; providing a catalyst; catalyzing an isomerization of said internal olefin(s) by said catalyst; producing an isomerized olefin mixture by said isomerization of said internal olefin(s); catalyzing a hydroformylation of said isomerized olefin mixture by said catalyst; and producing a branched aldehyde mixture by said hydroformylation of said isomerized olefin mixture. In an embodiment, this method can also have the steps of: reacting said branched aldehyde mixture with hydrogen; and producing a branched alcohol mixture by said reacting said branched aldehyde mixture.

In an embodiment, this method can also have the step of: providing a mixed olefins feed which is a mixture of an internal olefin and an alpha olefin. In an embodiment, this method can also have the step of: providing said mixed olefins feed which is a mixture of one or more C4 to C36 internal olefins, and one or more C4 to C36 alpha olefins. In an embodiment, a method can have the steps of: providing said mixed olefins feed; providing a catalyst; catalyzing an isomerization of said mixed olefins by said catalyst; producing an isomerized olefin mixture by said isomerization of said mixed olefins; catalyzing a hydroformylation of said mixed olefins by said catalyst; and producing a branched aldehyde mixture by said hydroformylation of said mixed olefins. In an embodiment, this method can also have the steps of: reacting said branched aldehyde mixture with hydrogen; and producing a branched alcohol mixture by said reacting said branched aldehyde mixture.

In an embodiment, a method can have the steps of: providing a C4-C36 alkene; providing a first catalyst; isomerizing said C4-C36 alkene catalyzed by said first catalyst; and producing an intermediate product composition having a plurality of isomerized alkenes, wherein said intermediate product composition has at least 60 wt. % of said plurality of isomerized alkenes; and hydroformylating said plurality of isomerized alkenes. In an embodiment, this process can further have the step of: producing a branched aldehyde. In an embodiment, this process can further have the step of: producing a branched aldehyde product composition by said hydroformylating that has a branched aldehyde product of at least 60 wt. % of said plurality of branched aldehydes.

In an embodiment, a composition can have a mixture of C8-C36 alcohols, wherein less than 60% of the mixture of C8-C36 alcohols are linear alcohols, wherein greater than 25% of the mixture of C8-C36 alcohols are 2-methyl branched alcohols, and wherein and greater than 8% of the mixture of C8-C36 alcohols are 2-ethyl branched alcohols. In an embodiment, this composition can have a mixture of C8-C36 alcohols wherein greater than 10% of the alcohols are 2-ethyl branched alcohols. In an embodiment, this composition can have a mixture of C8-C36 alcohols wherein greater than 12% of the alcohols are 2-ethyl branched alcohols. In an embodiment, this composition can have a mixture of C8-C36 alcohols wherein greater than 14% of the alcohols are 2-ethyl branched alcohols. In an embodiment, this composition can have a mixture of C8-C36 alcohols wherein greater than 16% of the alcohols are 2-ethyl branched alcohols. In an embodiment, this composition can have a mixture of C8-C36 alcohols wherein greater than 18% of the alcohols are 2-ethyl branched alcohols. In an embodiment, this composition can have a mixture of C8-C36 alcohols wherein greater than 20% of the alcohols are 2-ethyl branched alcohols.

In another embodiment, a composition can have a mixture of C8-C36 alcohols, wherein less than 50% of the C8-C36 alcohols are linear alcohols, wherein greater than 30% of the C8-C36 alcohols are 2-methyl branched alcohols, and wherein greater than 8% of the C8-C36 alcohols are 2-ethyl branched alcohols. In an embodiment, this composition can have a mixture of C8-C36 alcohols wherein greater than 10% of the alcohols are 2-ethyl branched alcohols. In an embodiment, this composition can have a mixture of C8-C36 alcohols wherein greater than 12% of the alcohols are 2-ethyl branched alcohols. In an embodiment, this composition can have a mixture of C8-C36 alcohols wherein greater than 14% of the alcohols are 2-ethyl branched alcohols. In an embodiment, this composition can have a mixture of C8-C36 alcohols wherein greater than 16% of the alcohols are 2-ethyl branched alcohols. In an embodiment, this composition can have a mixture of C8-C36 alcohols wherein greater than 18% of the alcohols are 2-ethyl branched alcohols. In an embodiment, this composition can have a mixture of C8-C36 alcohols wherein greater than 20% of the alcohols are 2-ethyl branched alcohols.

In an embodiment, the composition can have a mixture of C8-C36 alcohols, wherein less than 60% of the mixture of C8-C36 alcohols are linear alcohols, wherein greater than 25% of the mixture of C8-C36 alcohols are 2-methyl branched alcohols, wherein and greater than 8% of the mixture of C8-C36 alcohols are 2-ethyl branched alcohols, and wherein the alcohol mixture contains about 90% or greater C13 alcohols (i.e. tridecanols), less than 60% of the alcohol mixture is linear 1-tridecanol, and greater than 25% of the alcohol mixture is 2-methyldodecanol and greater than 8% of the alcohol mixture is 2-ethylundecanol. In an embodiment, this composition can have a mixture of C8-C36 alcohols wherein greater than 10% of the alcohol mixture is 2-ethylundecanol. In an embodiment, this composition can have a mixture of C8-C36 alcohols wherein greater than 12% of the alcohol mixture is 2-ethylundecanol. In an embodiment, this composition can have a mixture of C8-C36 alcohols wherein greater than 14% of the alcohol mixture is 2-ethylundecanol. In an embodiment, this composition can have a mixture of C8-C36 alcohols wherein greater than 16% of the alcohol mixture is 2-ethylundecanol. In an embodiment, this composition can have a mixture of C8-C36 alcohols wherein greater than 18% of the alcohol mixture is 2-ethylundecanol. In an embodiment, this composition can have a mixture of C8-C36 alcohols wherein greater than 20% of the alcohol mixture is 2-ethylundecanol.

The composition can have a mixture of C8-C36 alcohols, wherein less than 60% of the mixture of C8-C36 alcohols are linear alcohols, wherein greater than 25% of the mixture of C8-C36 alcohols are 2-methyl branched alcohols, wherein and greater than 8% of the mixture of C8-C36 alcohols are 2-ethyl branched alcohols, and wherein the alcohol mixture contains about 90% or greater C15 alcohols (i.e. pentadecanols) wherein less than 60% of the alcohol mixture is linear 1-pentadecanol, and greater than 25% of the alcohol mixture is 2-methyltetradecanol and greater than 8% of the alcohol mixture is 2-ethyltridecanol. In an embodiment, the composition can have a mixture of C8-C36 alcohols wherein greater than 10% of the alcohol mixture is 2-ethyltridecanol. In an embodiment, the composition can have a mixture of C8-C36 alcohols wherein greater than 12% of the alcohol mixture is 2-ethyltridecanol. In an embodiment, the composition can have a mixture of C8-C36 alcohols wherein greater than 14% of the alcohol mixture is 2-ethyltridecanol. In an embodiment, this composition can have a mixture of C8-C36 alcohols wherein greater than 16% of the alcohol mixture is 2-ethyltridecanol. In an embodiment, this composition can have a mixture of C8-C36 alcohols wherein greater than 18% of the alcohol mixture is 2-ethyltridecanol. In an embodiment, this composition can have a mixture of C8-C36 alcohols wherein greater than 20% of the alcohol mixture is 2-ethyltridecanol.

A composition, can have a mixture of C8-C36 aldehydes, wherein less than 60% of the mixture of C8-C36 aldehydes are linear aldehydes, wherein greater than 25% of the mixture of C8-C36 aldehydes are 2-methyl branched aldehydes, and wherein greater than 8% of the mixture of C8-C36 aldehydes are 2-ethyl branched aldehydes. In an embodiment, this composition can have a mixture of C8-C36 aldehydes wherein greater than 10% of the aldehydes are 2-ethyl branched aldehydes. In an embodiment, this composition can have a mixture of C8-C36 aldehydes wherein greater than 12% of the aldehydes are 2-ethyl branched aldehydes. In an embodiment, this composition can have a mixture of C8-C36 aldehydes wherein greater than 14% of the aldehydes are 2-ethyl branched aldehydes. In an embodiment, this composition can have a mixture of C8-C36 aldehydes wherein greater than 16% of the aldehydes are 2-ethyl branched aldehydes. In an embodiment, this composition can have a mixture of C8-C36 aldehydes wherein greater than 18% of the aldehydes are 2-ethyl branched aldehydes. In an embodiment, this composition can have a mixture of C8-C36 aldehydes wherein greater than 20% of the aldehydes are 2-ethyl branched aldehydes.

In an embodiment, a composition can have a mixture of C8-C36 aldehydes, wherein less than 50% of the mixture of C8-C36 aldehydes are linear aldehydes, wherein greater than 30% of the mixture of C8-C36 aldehydes are 2-methyl branched aldehydes, and wherein greater than 8% of the mixture of C8-C36 aldehydes are 2-ethyl branched aldehydes. In an embodiment, this composition can have a mixture of C8-C36 aldehydes wherein greater than 10% of the aldehydes are 2-ethyl branched aldehydes. In an embodiment, this composition can have a mixture of C8-C36 aldehydes wherein greater than 12% of the aldehydes are 2-ethyl branched aldehydes. In an embodiment, this composition can have a mixture of C8-C36 aldehydes wherein greater than 14% of the aldehydes are 2-ethyl branched aldehydes. In an embodiment, this composition can have a mixture of C8-C36 aldehydes wherein greater than 16% of the aldehydes are 2-ethyl branched aldehydes. In an embodiment, this composition can have a mixture of C8-C36 aldehydes wherein greater than 18% of the aldehydes are 2-ethyl branched aldehydes. In an embodiment, this composition can have a mixture of C8-C36 aldehydes wherein greater than 20% of the aldehydes are 2-ethyl branched aldehydes.

In an embodiment, a composition can have a mixture of C8-C36 aldehydes, wherein less than 60% of the mixture of C8-C36 aldehydes are linear aldehydes, wherein greater than 25% of the mixture of C8-C36 aldehydes are 2-methyl branched aldehydes, wherein greater than 8% of the mixture of C8-C36 aldehydes are 2-ethyl branched aldehydes, and wherein the aldehyde mixture contains about 90% or greater C13 aldehydes (i.e. tridecanals) wherein less than 60% of the aldehyde mixture is linear 1-tridecanal, and greater than 25% of the aldehyde mixture is 2-methyldodecanal and greater than 8% of the aldehyde mixture is 2-ethylundecanal. In an embodiment, this composition can have a mixture of C8-C36 aldehydes wherein greater than 10% of the aldehyde mixture is 2-ethylundecanal. In an embodiment, this composition can have a mixture of C8-C36 aldehydes wherein greater than 12% of the aldehyde mixture is 2-ethylundecanal. In an embodiment, this composition can have a mixture of C8-C36 aldehydes wherein greater than 14% of the aldehyde mixture is 2-ethylundecanal. In an embodiment, this composition can have a mixture of C8-C36 aldehydes wherein greater than 16% of the aldehyde mixture is 2-ethylundecanal. In an embodiment, this composition can have a mixture of C8-C36 aldehydes wherein greater than 18% of the aldehyde mixture is 2-ethylundecanal. In an embodiment, this composition can have a mixture of C8-C36 aldehydes wherein greater than 20% of the aldehyde mixture is 2-ethylundecanal.

In an embodiment, the composition can have a mixture of C8-C36 aldehydes, wherein less than 60% of the mixture of C8-C36 aldehydes are linear aldehydes, wherein greater than 25% of the mixture of C8-C36 aldehydes are 2-methyl branched aldehydes, wherein greater than 8% of the mixture of C8-C36 aldehydes are 2-ethyl branched aldehydes, and wherein the aldehyde mixture contains about 90% or greater C15 aldehydes (i.e. pentadecanals) wherein less than 60% of the aldehyde mixture is linear 1-pentadecanal, and greater than 25% of the aldehyde mixture is 2-methyltetradecanal and greater than 8% of the aldehyde mixture is 2-ethyltridecanal. In an embodiment, this composition can have a mixture of C8-C36 aldehydes wherein greater than 10% of the aldehyde mixture is 2-ethyltridecanal. In an embodiment, this composition can have a mixture of C8-C36 aldehydes wherein greater than 12% of the aldehyde mixture is 2-ethyltridecanal. In an embodiment, this composition can have a mixture of C8-C36 aldehydes wherein greater than 14% of the aldehyde mixture is 2-ethyltridecanal. In an embodiment, this composition can have a mixture of C8-C36 aldehydes wherein greater than 16% of the aldehyde mixture is 2-ethyltridecanal. In an embodiment, this composition can have a mixture of C8-C36 aldehydes wherein greater than 18% of the aldehyde mixture is 2-ethyltridecanal. In an embodiment, this composition can have a mixture of C8-C36 aldehydes wherein greater than 20% of the aldehyde mixture is 2-ethyltridecanal.

A product composition produced as a product of a process, can have the steps of: reacting a mixture of C8-C36 aldehydes, wherein less than 60% of the mixture of C8-C36 aldehydes are linear aldehydes, wherein greater than 25% of the mixture of C8-C36 aldehydes are 2-methyl branched aldehydes, and wherein greater than 8% of the mixture of C8-C36 aldehydes are 2-ethyl branched aldehydes, with an amine and hydrogen to produce a mixture of C8-C36 amines wherein less than 60% of the amines are linear amines, and greater than 25% of the amines are 2-methyl branched amines and greater than 8% of the amines are 2-ethyl branched amines; and producing an amine composition. The product composition is produced by the reacting step wherein the reacting amine is ammonia and the amine composition produced is a mixture of primary amines. The product composition is produced by the reacting step wherein the reacting amine is a primary amine and the amine composition produced is a mixture of secondary amines. The product composition is produced by the reacting step wherein the reacting amine is a secondary amine and the amine composition produced is a mixture of tertiary amines.

A product amine oxide composition produced as a product of a process having the steps of: reacting a mixture of C8-C36 aldehydes, wherein less than 60% of the mixture of C8-C36 aldehydes are linear aldehydes, wherein greater than 25% of the mixture of C8-C36 aldehydes are 2-methyl branched aldehydes, and wherein greater than 8% of the mixture of C8-C36 aldehydes are 2-ethyl branched aldehydes, with an amine and hydrogen to produce a mixture of C8-C36 amines wherein less than 60% of the amines are linear amines, and greater than 25% of the amines are 2-methyl branched amines and greater than 8% of the amines are 2-ethyl branched amines; producing an amine composition wherein less than 60% of the amines are linear amines, and greater than 25% of the amines are 2-methyl branched amines and greater than 8% of the amines are 2-ethyl branched amines with; and further comprising the step of reacting the amine composition with oxygen or other oxidizing agents to produce an amine oxide mixture having a mixture of C8-C36 amine oxides wherein less than 60% of the amine oxides are linear amine oxides, and greater than 25% of the amine oxides are 2-methyl branched amine oxides and greater than 8% of the amine oxides are 2-ethyl branched amine oxides. In an embodiment, this process produces at least one amine oxide, or a plurality of amine oxides, each of which is a surfactant. In an embodiment, the amide oxide mixture produced by this process has a surfactant. In an embodiment, the amide oxide mixture produced by this process is a surfactant composition.

A product carboxylic acid composition produced as a product of a process, comprising the steps of: reacting a mixture of C8-C36 aldehydes, wherein less than 60% of the mixture of C8-C36 aldehydes are linear aldehydes, wherein greater than 25% of the mixture of C8-C36 aldehydes are 2-methyl branched aldehydes, and wherein greater than 8% of the mixture of C8-C36 aldehydes are 2-ethyl branched aldehydes, with oxygen or other oxidizing agents to produce a mixture of C8-C36 carboxylic acids wherein less than 60% of the carboxylic acids are linear carboxylic acids, and greater than 25% of the carboxylic acids are 2-methyl branched carboxylic acids and greater than 8% of the carboxylic acids are 2-ethyl branched carboxylic acids; and producing a product carboxylic acid composition. In an embodiment, the carboxylic acids produced by this process are corrosion inhibitors. In an embodiment, the product ester composition produced by this process are lubricants, or lubricant additives. In an embodiment, the product ester composition produced by this process are plasticizers.

A product ester composition produced by the process comprising the steps of: reacting a mixture of C8-C36 alcohols, wherein less than 60% of the mixture of C8-C36 alcohols are linear alcohols, wherein greater than 25% of the mixture of C8-C36 alcohols are 2-methyl branched alcohols, and wherein and greater than 8% of the mixture of C8-C36 alcohols are 2-ethyl branched alcohols, with compounds having one or more carboxylic acid functions. The product ester composition of this process wherein the compounds comprising one or more carboxylic acid functions are mono-carboxylic acids and the ester composition produced is a mixture of mono-esters. The product ester composition of this process wherein the compounds comprising one or more carboxylic acid functions are dicarboxylic acids and the ester composition produced is a mixture of diesters. The product ester composition of this process wherein the compounds having one or more carboxylic acid functions are polyacids and the ester composition produced has a mixture of polyesters.

A product ester composition produced by a process comprising the steps of: reacting a mixture of C8-C36 aldehydes, wherein less than 60% of the mixture of C8-C36 aldehydes are linear aldehydes, wherein greater than 25% of the mixture of C8-C36 aldehydes are 2-methyl branched aldehydes, and wherein greater than 8% of the mixture of C8-C36 aldehydes are 2-ethyl branched aldehydes, with oxygen or other oxidizing agents to produce a mixture of C8-C36 carboxylic acids wherein less than 60% of the carboxylic acids are linear carboxylic acids, and greater than 25% of the carboxylic acids are 2-methyl branched carboxylic acids and greater than 8% of the carboxylic acids are 2-ethyl branched carboxylic acids; producing a product carboxylic acid composition; and reacting the product carboxylic acid composition with compounds having one or more alcohol functions to produce the product ester composition. The product ester composition of this process wherein the compounds having one or more alcohol functions are mono-alcohols and the ester composition produced is a mixture of mono-esters. The product ester composition of this process wherein the compounds having one or more alcohol functions are diols (glycols) and the ester composition produced is a mixture of diesters. The product ester composition of this process wherein the compounds having one or more alcohol functions are polyols and the ester composition produced has a mixture of polyesters. In an embodiment, the product ester compositions produced by this process are lubricants or lubricant additives. In an embodiment, the product ester compositions produced by this process are plasticizers.

A product alkyl sulfate composition produced by the process having the steps of reacting a mixture of C8-C36 alcohols, wherein less than 60% of the mixture of C8-C36 alcohols are linear alcohols, wherein greater than 25% of the mixture of C8-C36 alcohols are 2-methyl branched alcohols, and wherein and greater than 8% of the mixture of C8-C36 alcohols are 2-ethyl branched alcohols, with a sulfating agent to produce a mixture of C8-C36 alcohol sulfates wherein less than 60% of the alcohol sulfates are linear alcohol sulfates, and greater than 25% of the alkyl sulfates are 2-methyl branched alkyl sulfates and greater than 8% of the alkyl sulfates are 2-ethyl branched alkyl sulfates. In an embodiment, this process produces at least one alkyl sulfate, or a plurality of alkyl sulfates, each of which is a surfactant. The product alkyl sulfate composition of this process wherein the alkyl sulfate mixture has a surfactant. The product alkyl sulfate composition of this process wherein the alkyl sulfate mixture is a surfactant composition.

A product alcohol alkoxylate composition produced by a process comprising the steps of: reacting a mixture of C8-C36 alcohols, wherein less than 60% of the mixture of C8-C36 alcohols are linear alcohols, wherein greater than 25% of the mixture of C8-C36 alcohols are 2-methyl branched alcohols, and wherein and greater than 8% of the mixture of C8-C36 alcohols are 2-ethyl branched alcohols, with an alkoxylating agent to produce a product alcohol alkoxylate composition comprising a mixture comprising C8-C36 alcohol alkoxylates wherein less than 60% of the alcohol alkoxylates are linear alcohol alkoxylates, and greater than 25% of the alcohol alkoxylates are 2-methyl branched alcohol alkoxylates and greater than 8% of the alcohol alkoxylates are 2-ethyl branched alcohol alkoxylates. In an embodiment, this process produces at least one alcohol alkoxylate, or a plurality of alcohol alkoxylates, each of which is a surfactant. The product alcohol alkoxylate composition produced by this process wherein the alcohol alkoxylate mixture comprises a surfactant. The product alcohol alkoxylate composition produced by this process is a surfactant composition. The product alcohol alkoxylate composition produced by this process wherein said alkoxylating agent is ethylene oxide, propylene oxide, butylene oxide or epoxide mixtures comprising ethylene oxide, propylene oxide or butylene oxide.

A product alcohol alkoxylated sulfate (i.e. alkyl ether sulfate) produced by the steps of: reacting a product alcohol alkoxylate composition produced by a process having the step of reacting a mixture of C8-C36 alcohols, wherein less than 60% of the mixture of C8-C36 alcohols are linear alcohols, wherein greater than 25% of the mixture of C8-C36 alcohols are 2-methyl branched alcohols, and wherein and greater than 8% of the mixture of C8-C36 alcohols are 2-ethyl branched alcohols, with an alkoxylating agent to produce a product alcohol alkoxylate composition comprising a mixture comprising C8-C36 alcohol alkoxylates wherein less than 60% of the alcohol alkoxylates are linear alcohol alkoxylates, and greater than 25% of the alcohol alkoxylates are 2-methyl branched alcohol alkoxylates and greater than 8% of the alcohol alkoxylates are 2-ethyl branched alcohol alkoxylates; and reacting the product alcohol alkoxylate composition with a sulfating agent to produce a product alcohol alkoxylated sulfate mixture comprising C8-C36 alcohol alkoxylated sulfates wherein less than 60% of the alcohol alkoxylated sulfates are linear alcohol alkoxylated sulfates, and greater than 25% of the alcohol alkoxylated sulfates are 2-methyl branched alcohol alkoxylated sulfates and greater than 8% of the alcohol alkoxylated sulfates are 2-ethyl branched alcohol alkoxylated sulfates. In an embodiment, this process produces at least one alcohol alkoxylated sulfate (i.e. alkyl ether sulfate), or a plurality of alcohol alkoxylated sulfates (i.e. alkyl ether sulfates), each of which is a surfactant. A product alcohol alkoxylated sulfate (i.e. alkyl ether sulfate) produced by this process wherein the alcohol alkoxylated sulfate mixture comprises a surfactant. A product alcohol alkoxylated sulfate (i.e. alkyl ether sulfate) produced by this process wherein the alcohol alkoxylated sulfate mixture is a surfactant composition.

A process for producing a product aldehyde composition comprising a mixture of two or more branched aldehydes, comprising the steps of: providing at least two C4-C36 alpha olefins of different chain lengths; providing a first catalyst; isomerizing said alpha olefin mixture catalyzed by said first catalyst under an atmosphere comprising CO and H2 at a first pressure; producing an intermediate isomerized olefins product composition having a mixture of alpha olefins and internal olefins; hydroformylating said intermediate isomerized olefins product catalyzed by said first catalyst under an atmosphere comprising CO and H2 at a second pressure higher than said first pressure; and producing a product aldehyde composition which is a mixture of branched aldehydes of at least two different C5-C37 chain lengths. This process for producing a product aldehyde composition having a mixture of C5-C37 branched aldehydes further comprising the step of: separating said mixture of C5-C37 branched aldehydes from the first catalyst stream via a distillation process. This process for producing a product aldehyde composition having a mixture of C5-C37 branched aldehydes in which the catalyst is a rhodium catalyst. This process for producing a product aldehyde composition having a mixture of C5-C37 branched aldehydes in which the catalyst is a homogeneous rhodium catalyst. This process for producing a product aldehyde composition having a mixture of C5-C37 branched aldehydes in which the catalyst is an organometallic complex of rhodium and one type of an organophosphorus ligand or an organometallic complex of rhodium and more than one type of an organophosphorus ligand. This process for producing a product aldehyde composition having a mixture of C5-C37 branched aldehydes in which the first pressure is in a range of from 0.01 bar(absolute) and 20 bar(absolute). This process for producing a product aldehyde composition having a mixture of C5-C37 branched aldehydes in which the intermediate isomerized olefin product comprises at least 20 wt. % of internal olefins. This process for producing a product aldehyde composition having a mixture of C5-C37 branched aldehydes in which the second pressure is in a range of from 1 bar(g) to 400 bar(g). This process for producing a product aldehyde composition having a mixture of C5-C37 branched aldehydes wherein the product branched aldehydes are 2-alkyl branched aldehydes. This process for producing a product aldehyde composition having a mixture of C5-C37 branched aldehydes wherein the product aldehyde composition comprises at least 25 wt. % of branched aldehydes. This process for producing a product aldehyde composition having a mixture of C5-C37 branched aldehydes, wherein a product aldehyde composition has at least two different C5-C37 chain lengths, further having the step of separating the product aldehyde composition comprising a mixture of at least two different C5-C37 branched aldehydes, via a series of distillation processes, into individual, purified branched aldehyde products wherein each purified branched aldehyde product that is distilled consists essentially of a single carbon number chain length product in the carbon number range of C5-C37.

A process for producing a mixture of two or more branched alcohols, comprising the steps of: providing at least two C4-C36 alpha olefins of different chain lengths; providing a first catalyst; isomerizing said alpha olefin mixture catalyzed by said first catalyst under an atmosphere comprising CO and H2 at a first pressure; producing an intermediate isomerized olefins product composition having a mixture of alpha olefins and internal olefins; hydroformylating said intermediate isomerized olefins product catalyzed by said first catalyst under an atmosphere comprising CO and H2 at a second pressure higher than said first pressure to produce a mixture of branched aldehydes of at least two different C5-C37 chain lengths; separating said mixture of C5-C37 branched aldehydes from the rhodium comprising catalyst stream via a distillation process; hydrogenating said mixture of C5-C37 branched aldehydes in the presence of hydrogen and a hydrogenation catalyst at elevated hydrogen pressure; and producing a product which is a mixture of branched alcohols of at least two different carbon chain lengths in the carbon number range of C5-C37, which can also be expressed as two different C5-C37 chain lengths. This process for producing a mixture of C5-C37 branched alcohols in which the catalyst is a rhodium catalyst. This process for producing a mixture of C5-C37 branched alcohols in which the catalyst is a homogeneous rhodium catalyst. This process for producing a mixture of C5-C37 branched alcohols in which the catalyst is an organometallic complex of rhodium and one type of an organophosphorus ligand or an organometallic complex of rhodium and more than one type of an organophosphorus ligand. This process for producing a mixture of C5-C37 branched alcohols wherein the first pressure is in a range of 0.01 bar(absolute) and 20 bar(absolute). This process for producing a mixture of C5-C37 branched alcohols wherein the intermediate isomerized olefin product comprises at least 20 wt. % of internal olefins. This process for producing a mixture of C5-C37 branched alcohols wherein the second pressure is in a range of from 1 bar(g) to 400 bar(g). This process for producing a mixture of C5-C37 branched alcohols wherein the mixture of C5-C37 branched alcohols are 2-alkyl branched alcohols. This process for producing a mixture of C5-C37 branched alcohols wherein the mixture of C5-C37 branched alcohols comprises at least 25 wt. % of branched alcohols. This process for producing a mixture of C5-C37 branched alcohols wherein the mixture has at least two different C5-C37 chain lengths, and further comprising the step of: separating the mixture of at least two C5-C37 branched alcohols, via a series of distillation processes, into individual, purified branched alcohol products wherein each purified branched alcohol product that is distilled consists essentially of a single carbon number chain length product in the carbon number range of C5-C37. This process for producing a mixture of C5-C37 branched alcohols, further comprises the steps of: providing two alpha olefins wherein the first alpha olefin is a C12 alpha olefin (i.e. 1-dodecene) and the second alpha olefin is a C14 alpha olefin (i.e. 1-tetradecene); and producing a mixture of branched C13 aldehydes and branched C15 aldehydes; and producing a mixture of branched C13 alcohols and branched C15 alcohols. This process for producing a mixture of C13 branched alcohols further comprising the steps of: separating the mixture of C13 branched alcohols and C15 branched alcohols, via a first distillation step to produce a purified C13 branched alcohol product and via a second distillation step to produce a purified branched C15 alcohol product.

A process, having the steps of: providing a first catalyst having an organometallic complex having at least one of a rhodium and a cobalt; and at least one type of an organophosphorus ligand; providing a mixture of one or more C4-C36 linear alpha olefins; providing a gas phase comprising CO; isomerizing the linear alpha olefin by the first catalyst in the presence of CO at a first pressure to produce an isomerized olefin; and hydroformylating the isomerized olefin by the first catalyst in the presence of CO and H2 at a second pressure different from the first pressure producing a branched aldehyde. In an embodiment, the branched aldehyde can be a 2-alkyl branched aldehyde. In an embodiment, the organophosphorous ligand can be a phosphite ligand. In an embodiment, the organophosphorous ligand can be a phosphite ligand which is tris (2,4-di-t-butylphenyl) phosphite. In an embodiment, the at least one type of organophosphorus ligand can be a mixture of triphenylphosphine and tris (2,4-di-t-butylphenyl) phosphite. In an embodiment, this process can further have the steps of: providing a hydrogenation catalyst; providing hydrogen; hydrogenating the branched aldehyde in the presence of the hydrogen and the hydrogenation catalyst producing a branched alcohol.

A process, having the steps of: providing a first catalyst having an organometallic complex, the organometallic complex having at least one of a rhodium and a cobalt and at least one of an organophosphorus ligand; providing a mixture of one or more C4-C36 linear alpha olefins; providing a gas phase having CO; isomerizing the linear alpha olefin by the first catalyst in the presence of the CO at a first pressure to produce an isomerized olefin; and hydroformylating the isomerized olefin by the first catalyst in the presence of CO and H2 at a second pressure different from the first pressure producing a branched aldehyde. In an embodiment, the branched aldehyde can be a 2-alkyl branched aldehyde. In an embodiment, the organophosphorous ligand can be a phosphite ligand. In an embodiment, the organophosphorous ligand can be a phosphite ligand which is tris (2,4-di-t-butylphenyl) phosphite. In an embodiment, this process can further have a first organophosphorous ligand which can be triphenylphosphine and a second organophosphorous ligand which can be tris (2,4-di-t-butylphenyl) phosphite. In an embodiment, this process can further have the steps of: providing a hydrogenation catalyst; providing a hydrogen; and hydrogenating the branched aldehyde in the presence of the hydrogen and the hydrogenation catalyst producing a branched alcohol.

BRIEF DESCRIPTION OF THE DRAWINGS

The present invention in its several aspects and embodiments solves the problems discussed above and significantly advances the technology of branched compounds and methods for producing and manufacturing branched compounds. The present invention can become more fully understood from the detailed description and the accompanying drawings, wherein:

FIG. 7 shows Sales Specification 1;

FIG. 8 shows Sales Specification 2;

FIG. 9A shows Sales Specification 3, page 1;

FIG. 9B shows Sales Specification 3, page 2;

FIG. 10 shows Sales Specification 4;

FIG. 11A shows Sales Specification 5, page 1;

FIG. 11B shows Sales Specification 5, page 2;

FIG. 12 shows Sales Specification 6;

Herein, like reference numbers in one figure refer to like reference numbers in another figure.

DETAILED. DESCRIPTION OF THE INVENTION

Figure 1:
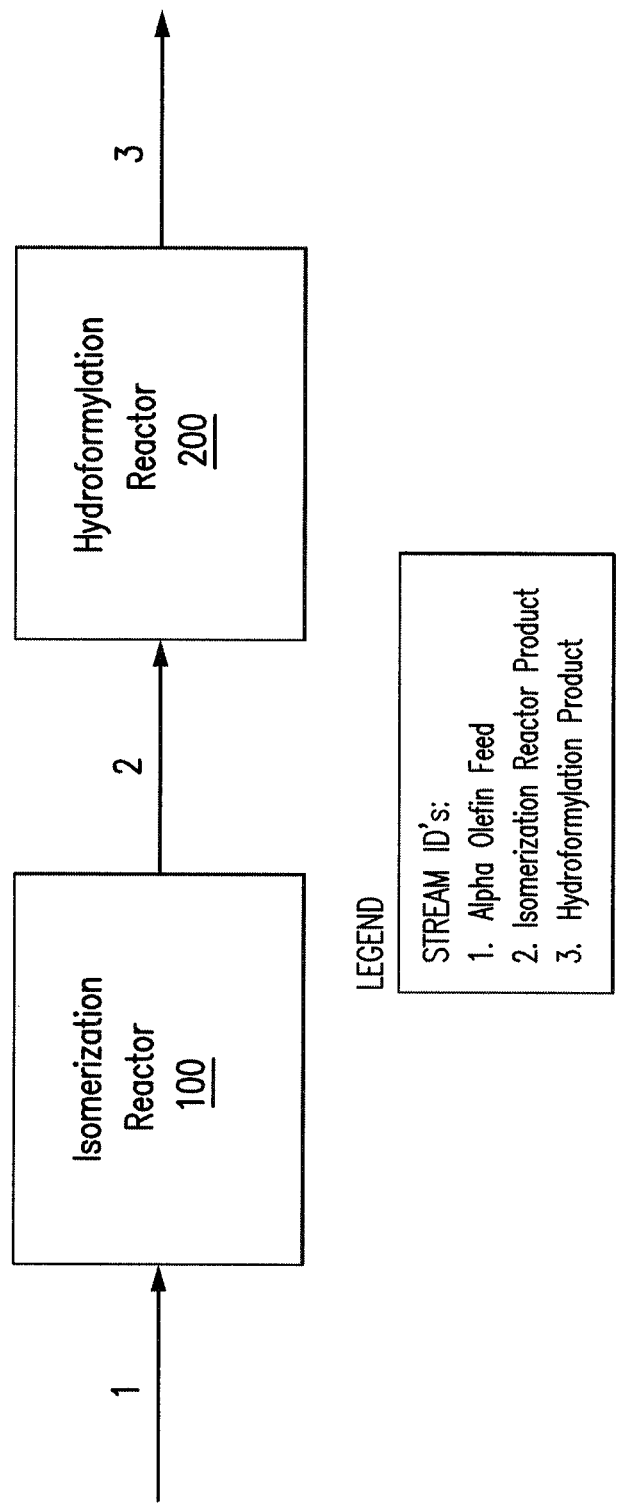
FIG. 1 shows an embodiment of a chemical manufacturing process having an isomerization reactor and an hydroformylation reactor.

In an embodiment, a two-step process is disclosed herein that produces branched aldehyde products, with 25% to 98%, or greater percent, branching, that are produced from an alpha olefin feedstock. Additionally, the two-step process disclosed herein employs an organometallic complex of rhodium and at least one organophosphorous ligand for both the first step which is an isomerization reaction step and the second step which is a hydroformylation reaction step. Additionally, the two-step process disclosed herein can use an organometallic complex of cobalt and at least one organophosphorous ligand for both a first step which is an isomerization reaction step and a second step which is a hydroformylation reaction step. Additionally, the two-step process disclosed herein can employ a mixed organometallic complex containing cobalt, rhodium and at least one organophosphorous ligand for both a first step which is an isomerization reaction step and a second step which is a hydroformylation reaction step.

Numeric values and ranges herein, unless otherwise stated, also are intended to have associated with them a tolerance and to account for variances of design and manufacturing. Thus, a number can include values "about" that number. For example, a value X is also intended to be understood as "about X". Likewise, a range of Y-Z, is also intended to be understood as within a range of from "about Y-about Z". Unless otherwise stated, significant digits disclosed for a number are not intended to make the number an exact limiting value. Variance and tolerance are inherent in mechanical design and the numbers disclosed herein are intended to be construed to allow for such factors (in non-limiting e.g., ±10 percent of a given value). Likewise, the claims are to be broadly construed in their recitations of numbers and ranges.

Every numerical range given throughout this specification will include every narrower numerical range that falls within such broader numerical range, as if such narrower numerical ranges were all expressly written herein. As regarding ranges and endpoints, every maximum numerical limitation given throughout this specification includes every lower numerical limitation, as if such lower numerical limitations were expressly written herein. Every minimum numerical limitation given throughout this specification will include every higher numerical limitation, as if such higher numerical limitations were expressly written herein.

Herein the term "reactor" means one or more physical reactors that individually or in combination are used to achieve a reactive step in chemical processing. Herein, "reaction step" and "reactive step" are used synonymously. A "reactor" can be a single vessel or optionally multiple vessels. A "reactor" can optionally be configured such that a reactive step occurs in one or more reactor vessels. If there are a number of reactor vessels, such reactor vessels can be operated in series, in parallel, or any combination thereof. Herein, the term "reactor" is the unit operation of conducting a chemical reaction processing step, also referred to as a reaction step, or reactive step.

For example, as shown in FIGS. 1-6 the representation of a reactor and/or the recitation of a reactor should not be construed to be limited to specifically a single physical reactor. Optionally a single physical reactor can be used to achieve a reaction step, or optionally a number of physical reactor vessels can be used to achieve the reaction step. Herein, the term "reactor" should be construed to mean a reactive step which in fact could be carried out in one or more reactors operating in series, parallel, or any combination thereof. Therefore, "isomerization reactor" should be construed to mean an isomerization step (meaning an isomerization reaction step) occurring in one or more reactors operating in series, parallel, or any combination thereof. Analogously, "hydroformylation reactor" should be construed to mean a hydroformylation step (meaning an hydroformylation reaction step) occurring in one or more reactors operating in series, parallel, or any combination thereof. Further, "hydrogenation reactor" should be construed to mean a hydrogenation step (meaning a hydrogenation reaction step) occurring in one or more reactors operating in series, parallel, or any combination thereof.

Unless otherwise stated temperatures recited herein are in degrees Celsius ("° C.")

Unless otherwise stated pressures recited herein are in bar(g), i.e. bars gauge. Herein, 0 bar(g) is atmospheric pressure, e.g. 14.70 psia (aka 0 psig).

Pressures herein can also be stated in bars absolute; herein noted as bar(a) or bar(absolute).

Pressures can also be stated in millibar; herein noted as millibar, millibar(a), millibar absolute or millibar(absolute), for which each of these means a pressure stated in units of millibar absolute, and are all equivalent and used interchangeably.

Unless otherwise stated percentages of composition recited herein are on a weight basis and disclosed as weight percent (wt. %).

Alternatively, herein, concentration can be expressed in units of parts per million, or ppm.

Herein, the number of carbons in a molecule is denoted with a capital "C" followed by an integer representing the carbon number of the molecule. For example, a "C12" molecule is a molecule having 12 carbons (i.e. 1-dodecene for example).

Herein, the term "olefin" is used synonymously with the term "alkene", meaning a molecule comprising a carbon-carbon double bond.

Herein "linear" is defined as a molecule, compound or chemical structure, having no branching along a carbon backbone (i.e. straight-chain).

Herein "branched" is defined as a molecule, compound or chemical structure, having one or more alkyl groups attached along a carbon backbone. "Branched" molecules are isomers of linear (i.e. straight-chain) molecules having the same number of carbon atoms.

Herein, the term "percent linear", in additional to its ordinary and customary meaning, is defined herein to mean the wt. % linear molecules in a composition.

Herein, the term "percent branched", in additional to its ordinary and customary meaning, is defined herein to mean the wt. % branched molecules in a composition. The term "percent branching" is use synonymously with "percent branched" and has the same meaning as "percent branched". As an example, for an aldehyde composition, the "percent branching" (also as "% branching") of the aldehyde means the wt. % of the aldehyde isomers that are branched versus the total wt. % of aldehydes present, i.e.:

Branching=100*(wt. % branched aldehydes)÷(wt. % branched aldehydes+wt. % linear aldehyde).

As an example, a branched C6 aldehyde composition comprising:

| | |
|---|---|
| 25 wt. % 1-Hexanal | (linear molecule) |
| 40 wt. % 2-Methyl-Pentanal | (branched molecule) |
| 35 wt. % 2-Ethyl-butanal | (branched molecule) |
| would have a Percent Branching = 75% | |

In another example, a branched C13 aldehyde composition comprising:

| | |
|---|---|
| 25 wt. % 1-Tridecanal | (linear molecule) |
| 40 wt. % 2-Methyl-dodecanal | (branched molecule) |
| 20 wt. % 2-Ethyl-undecanal | (branched molecule) |
| 15 wt. % 2-Propyl-decanal | (branched molecule) |
| would have a Percent Branching = 75%. | |

In this example, the C13 aldehyde branching occurs at the second carbon position from the aldehyde carbon and is defined as "2-alkyl" branching.

Herein, the percent "2-methyl branched" is defined as the wt. % of compounds having a methyl group branch at the second carbon position. In this C13 aldehyde example, the percent 2-methyl branched aldehyde=40 wt. % (i.e. the wt. % of 2-Methyl-dodecanal).

Herein, the percent "2-ethyl branched" is defined as the wt. % of compounds having an ethyl group branch at the second carbon position. In this C13 aldehyde example, the percent 2-ethyl branched aldehyde=20 wt. % (i.e. the wt. % of 2-Ethyl-undecanal).

Unless otherwise stated percent branching and percent linear recited herein are in weight percent (wt. %) is calculated based upon reactant and product weights, excluding nonparticipating compounds.

Herein, the term "percent isomerized", in additional to its ordinary and customary meaning, is defined herein to mean the wt. % of olefin molecules where the olefin has been isomerized from the alpha position to an internal olefin position. Specifically, the "percent isomerized" means the wt. % of the olefin composition being internal olefins, i.e.:

100*(wt. % internal olefin)÷(wt. % alpha olefin+wt. % internal olefin).

As an example, a C12 alpha olefin isomerized to produce a composition comprising:

| | |
|---|---|
| 25 wt. % 1-Dodecene | (alpha olefin) |
| 40 wt. % 2-Dodecene | (internal olefin)) |
| 35 wt. % 3-Dodecene | (internal olefin) |
| would have a Percent Isomerized = 75% | |

Unless otherwise stated the term "internal olefin" recited herein means an olefin in which a double bond is present in a position other than the alpha position.

Unless otherwise stated percent isomerized recited herein are in weight percent (wt. %) is calculated based upon reactant and product weights, excluding nonparticipating compounds.

In an embodiment, branched alcohols, can be manufactured by a process having the method steps of:

1. providing a C4-C36 alpha olefin;
2. providing a homogeneous rhodium organophosphorous ligand catalyst;
3. isomerizing said C4-C36 olefin catalyzed by said rhodium catalyst under an atmosphere of CO/H2 at a pressure between 0.01 bar(absolute) and 20 bar(absolute);
4. producing an intermediate isomerized olefin product composition having at least 20 wt. % of internal (non-alpha) olefins;
5. hydroformylating said intermediate isomerized olefin product catalyzed by said rhodium catalyst under an atmosphere of CO/H2 at a pressure between 1 bar(g) and 400 bar(g);
6. producing a branched aldehyde product composition having at least 25 wt. % branched aldehydes;

7. separating said branched aldehyde product from the rhodium comprising catalyst stream via a distillation process;
8. hydrogenating said branched aldehyde in the presence of a hydrogenation catalyst at elevated hydrogen pressure; and
9. producing a branched alcohols product composition having at least 40 wt. % branched alcohols.

In an embodiment, branched alcohols, can be manufactured by the a process having the method steps of:
1. providing a C4-C36 alpha olefin;
2. providing a homogeneous rhodium organophosphorous ligand catalyst;
3. isomerizing said C4-C36 olefin catalyzed by said rhodium catalyst under an atmosphere of CO/H2 at a pressure in a range of 0.01 bar(absolute) and 20 bar (absolute) and a CO/H2 molar ratio in a range of 10:1 and 1:10;
4. producing an intermediate isomerized olefin product composition having at least 20 wt. % of internal (non-alpha) olefins;

embodiment, the isomerization and hydroformylation reactions can be catalyzed by a cobalt organophosphorus ligand catalyst. In an embodiment, the isomerization and hydroformylation reactions can be catalyzed by a cobalt-rhodium organophosphorus ligand catalyst.

In an embodiment the catalyst can be a rhodium (—PPh$_3$) catalyst system.

For Example, a rhodium triphenylphosphine (—PPh$_3$) catalyst system can exist in different states and/or configurations which allow for use in different reactions such as for the isomerization reactions and hydroformylation reactions disclosed herein. As shown in sequence one below, on the far left it is shown that without the presence of CO, the catalyst is in an inactive state because the three attached —PPh$_3$ groups "block" the sites for catalyst activity. However, as CO is added to the system the —PPh$_3$ groups on the rhodium are increasingly replaced with CO groups which "opens" up the catalyst and makes it active and able to catalyze the isomerization and hydroformylation reactions of the embodiments disclosed herein.

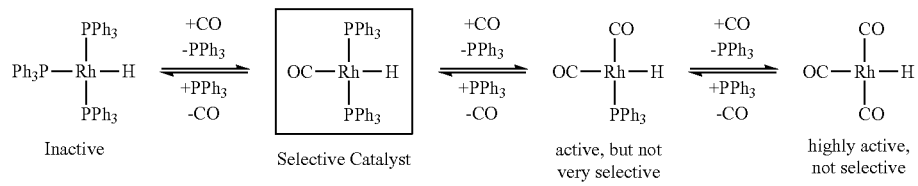

Sequence 1: Activation Sequence For Rhodium Triphenylphosphine 5. hydroformylating said intermediate isomerized olefin product catalyzed by said rhodium catalyst under an atmosphere of CO/H2 at a pressure between 1 bar(g) and 400 bar(g) and a CO/H2 molar ratio in a range of 10:1 and 1:10;
6. producing a branched aldehyde product composition having at least 25 wt. % branched aldehydes;
7. separating said branched aldehyde product from the rhodium comprising catalyst stream via a distillation process;
8. hydrogenating said branched aldehyde in the presence of a hydrogenation catalyst at elevated hydrogen pressure; and
9. producing a branched alcohols product composition having at least 40 wt. % branched alcohols.

FIG. 1 shows an embodiment of a chemical manufacturing process having an isomerization reactor and an hydroformylation reactor.

FIG. 1 describes a two-step process in which Stream 1 having alpha olefins that is fed to isomerization reactor 100 which produces Stream 2 having isomerized olefins that is fed to hydroformylation reactor 200 which produces Stream 3 having branched aldehydes.

Catalyst Specifications & Compositions

In an embodiment the same catalyst can be used in each of the first step and second step of the two-step process. In an embodiment, the same catalyst can be used in the isomerization reactor 100 and the hydroformylation reactor 200.

In an embodiment, the isomerization and hydroformylation reactions can be catalyzed by a rhodium organophosphorus ligand catalyst. The organophosphorus ligand catalyst can be activated by the presence of CO. In an Catalyst Composition In an embodiment, the molar ratio (P:Rh) of phosphorous ("P") to rhodium ("Rh") in the isomerization reaction or the hydroformylation reaction can be in a range of 1:1 to 1000:1, or 3:1 to 200:1, or 5:1 to 50:1, such as for non-limiting example 1:1, 3:1, 5:1, 10:1, 20:1, 30:1, 40:1, 50:1, 100:1, 200:1, 500:1 or 1000:1.

In an embodiment, the concentration of Rh in the isomerization reaction or the hydroformylation reaction can be in a range of 1 to 10000 ppm, 10 to 1,000 ppm, or 20-200 ppm, such as in non-limiting example 1 ppm, 20 ppm, 50 ppm, 100 ppm, 200 ppm, 300 ppm, 400 ppm, 500 ppm, 1000 ppm, 2000 ppm, 5000 ppm, 7500 ppm, or 10000 ppm In an embodiment, the catalyst used in the isomerization and hydroformylation reactions is an organometallic rhodium ligand complex formed from Rh(CO)$_2$ACAC ((Acetylacetonato)dicarbonylrhodium(I)) and tris (2,4,-di-t-butylphenyl) phosphite ligand.

Isomerization

The first step occurs in isomerization reactor 100 where the Stream 1 feed to isomerization reactor 100 can have a composition comprising:

A C4-C36 alpha olefin (or mixtures thereof);
Rhodium catalyst A;
Carbon Monoxide (CO); and
Hydrogen.

Optionally, Stream 1 can have a high-boiling inert solvent, for example Polyalphaolefin.

Rhodium catalyst A is an organometallic complex of Rhodium and at least one organophosphorus ligand. The isomerization reaction can proceed at a temperature of 30-300° C., e.g. 90° C. in the presence of CO and H2 at a pressure of 0.01 bar(absolute)-20 bar(absolute). The isomerization reaction conditions can also be described as proceeding at a temperature of 30-300° C., e.g. 90° C. under a CO and H2 atmosphere at a pressure of 0.01 bar(absolute)-20 bar(absolute). The isomerization reaction can proceed at a CO:H2 molar ratio in a range of 10:1 to 1:10.

The isomerization process can be processed batchwise, or on a continuous basis. All reactions and unit operations disclosed herein can be processed batchwise, or on a continuous basis.

In an embodiment, the catalyst used in this isomerization and hydroformylation reaction is a rhodium ligand complex as Rh(CO)$_2$ACAC ((Acetylacetonato)dicarbonylrhodium (I)) with tris (2,4,-di-t-butylphenyl) phosphite in a PAO-4 (polyalphaolefin) highboiling inert solvent.

In a nonlimiting example, Stream 1 can have one or more of the feedstocks specific in the sales specification of FIGS. 7-12.

In an embodiment, the feed having an alpha olefin, or having a mixture of linear olefins, can be isomerized at a temperature in a range of 30° C. to 500° C., or 40° C. to 200° C., or 50° C. to 120° C., such as in non-limiting example 30° C., 50° C., 80° C., 90° C., 100° C., 120° C., 150° C., 180° C., 200° C., 250° C., 300° C., 400° C., or 500° C.

In an embodiment, the feed having an alpha olefin, or having a mixture of linear olefins, can be isomerized at a pressure in a range of 0.0 bar(g) to 20 bar(g), 0.1 bar(g) to 10 bar(g), 0.5 bar(g) to 5 bar(g), such as in non-limiting example 0.01 bar(g), 1 bar(g), 5 bar(g), 7.5 bar(g), 9 bar(g), 10 bar(g), 12 bar(g), 15 bar(g), 18 bar(g), or 20 bar(g).

In an embodiment, an isomerization of a linear alpha olefin, or mixture of linear alpha olefins, can be isomerized at a pressure in a range of 0 bar(g) to 20 bar(g), such as 0 bar(g), 0.1 bar(g), 0.5 bar(g), 1 bar(g), 2 bar(g), 5 bar(g), 10 bar(g), or 20 bar(g).

In an embodiment, an isomerization of a linear alpha olefin, or mixture of linear alpha olefins, can be isomerized at a CO/H2 molar ratio in a range of 10:1 to 1:10, such as 5:1, 2:1, 1.5:1, 1.1:1, 1.05:1, 1:1, 1:1.05, 1:1.1, 1:1.15, 1:1.2, 1:1.3, 1:1.5, 1:2, 1:3, 1:5 or 1:10.

In an embodiment, an isomerization of a linear alpha olefin, or mixture of linear alpha olefins, can be isomerized at a CO/H2 molar ratio in a range of 1.2:1 to 1:1.2.

In an embodiment, an isomerization of a linear alpha olefin, or mixture of linear alpha olefins, can be isomerized at a pressure of 20 bar(g) or less and 100° C. or less, e.g. 1 bar(g) and 90° C. In an embodiment, an isomerization of a linear alpha olefin, or mixture of linear alpha olefins, can be isomerized at a pressure of 20 bar(g) or less and 100° C. or less and at a CO:H2 molar ratio of 1:1 or less, e.g.: 1 bar(g), 90° C. and a CO:H2 ratio of 1:1.15.

Stream 1—Alpha Olefin Feed Composition

In an embodiment, Stream 1 can be a C4-C36 linear alpha olefin. For example, the Stream 1 feed can be a 1-dodecene feedstock which substantially is a C12 linear alpha olefin, such as the AlphaPlus® 1-Dodecene (Chevron Phillips Chemical Company LP, P.O. Box 4910, The Woodlands, Tex. 77387-4910, phone (800) 231-3260) as shown in FIG. 7, Sales Specification 1.

In an embodiment, the Stream 1 feed can be a 1-dodecene feedstock which substantially is a C12 linear alpha olefin, such as the NEODENE® 12 (Shell Global Solutions, One Shell Plaza, 910 Louisiana, Houston, Tex. 77002-4916, US, phone (832) 337-2000) as shown in Sales specification 3, as shown in FIG. 9A-9B.

In another embodiment, Stream 1 feed can be a 1-dodecene feedstock which substantially is a C12 linear alpha olefin, such as INEOS Oligomers, Alpha Olefin C12 (dodecane-1) (2600 South Shore Boulevard, Suite 400, League City, Tex. 77573, phone (281) 535-4266) as shown in Sales specification 4, as shown in FIG. 10.

In an embodiment, the Stream 1 feed can be a 1-tetradecene feedstock which substantially is a C14 linear alpha olefin, such as the AlphaPlus® 1-tetradecene (Chevron Phillips Chemical Company LP, P.O. Box 4910, The Woodlands, Tex. 77387-4910, US, phone (800) 231-3260) as shown in FIG. 8, Sales Specification 2.

In an embodiment, the Stream 1 feed can be a 1-tetradecene feedstock which substantially is a C14 linear alpha olefin, such as the NEODENE® 14 (Shell Global Solutions, One Shell Plaza, 910 Louisiana, Houston, Tex. 77002-4916, US, phone (832) 337-2000) as shown in FIG. 11A-11B, Sales specification 5.

In another embodiment, Stream 1 feed can be a 1-tetradecene feedstock which substantially is a C14 linear alpha olefin, such as INEOS Oligomers, Alpha Olefin C14 (tetradecane-1) (2600 South Shore Boulevard, Suite 400, League City, Tex. 77573, phone (281) 535-4266) as shown in FIG. 12, Sales specification 6.

In an embodiment, the Stream 1 feedstock can be a composition having one or more alpha olefins. The alpha olefins of the Stream 1 feed can be the same, or different, and have the same or different carbon chain lengths. For example, the Stream 1 alpha olefins fed as reactants for isomerization can be one or more alpha olefins from the group of C4-C36 alpha olefins, or greater.

In an embodiment, a C12 linear alpha olefin fed as a reactant for isomerization can be 90.0 wt. % or greater, such as greater than 94.0 wt. % C12 linear alpha olefin, or 94.6 wt. % C12 linear alpha olefin, or 99 wt. % C12 linear alpha olefin, or greater.

In an embodiment, a C14 alpha olefin fed as a reactant for isomerization can be 90.0 wt. % or greater, such as greater than 93.0 wt. % C14 linear alpha olefin, or 93.4 wt. % C14 linear alpha olefin, or 99 wt. % C14 linear alpha olefin, or greater.

In an embodiment, the alpha olefin feedstock to the isomerization reactor has a concentration of vinylidene of 10 wt. % or less, e.g. 4 wt. % or less.

Stream 2, Isomerization Reactor Product Stream Composition

The isomerization reaction of isomerization reactor 100 produces an isomerization reaction product stream which can be fed into hydroformylation reaction 200. Stream 2, can have a composition comprising internal olefin products of the isomerization reaction in which a portion of the starting alpha olefins have been isomerized to an olefin mixture comprising in non-limiting example:
  >20 wt. % internal olefins, i.e. olefins where the double bond has been isomerized internally to the molecule and is no longer in the alpha position; and
  <80 wt. % alpha olefins.

Stream 2 is an isomerization reactor product stream having isomerized olefins which can have a percent isomerization in a range of 5 wt. % to 99%, or greater, e.g. 5 wt. %, 10 wt. %, 15 wt. %, 20 wt. %, 25 wt. %, 30 wt. %, 35 wt. %, 40 wt. %, 45 wt. %, 50 wt. %, 60 wt. %, 70 wt. %, 80 wt. %, 90 wt. %, or 99 wt. %. In an embodiment, stream 2 which is an isomerization reactor product stream can have internal olefins in a composition of 20 wt. %, or greater.

Stream 3, Hydroformylation Product Composition

In an embodiment, stream 3 which is a hydroformylation product stream can have a composition which is greater than 25 wt. % branched aldehydes.

Hydroformylation

The second step of the two-step process depicted in FIG. 1 occurs in Hydroformylation Reactor 200. In this step, the feed (Stream 2) has a composition comprising:

A C4-C36 olefin mixture comprising;
>20 wt. % linear internal olefins,
<80 wt. % linear alpha olefins;
Rhodium catalyst A,
Carbon Monoxide (CO),
Hydrogen, and
C5-C37 Aldehydes (minor components).

Optionally, stream 2 can comprise a high-boiling inert solvent.

The reaction in Hydroformylation Reactor 200 proceeds using the same Rhodium Catalyst A and at a temperature of 30-300 C. The reaction in Hydroformylation Reactor 200 occurs under a CO/H2 atmosphere and at a pressure greater than the pressure in Isomerization Reactor (100) as the higher pressure favors the production of the desired branched aldehydes. This step produces a reaction product (Stream 3) where the olefin mixture (or a portion of the olefin mixture) has been hydroformylated to produce an aldehyde mixture comprising:

>25 wt. % branched aldehydes, and
<75 wt. % linear aldehydes.

In an embodiment, the feed to hydroformylation having an internal olefin, or having a mixture alpha olefins and internal olefins, can be hydroformylated at a temperature in a range of 30° C. to 500° C., or 40° C. to 200° C., or 50° C. to 120° C., such as in non-limiting example 30° C., 50° C., 80° C., 90° C., 100° C., 120° C., 150° C., 180° C., 200° C., 250° C., 300° C., 400° C., or 500° C.

In an embodiment, the feed to hydroformylation having an internal olefin, or having a mixture of alpha olefins and internal olefins, can be hydroformylated at a pressure in a range of 0 bar(g) to 500 bar(g), 5 bar(g) to 100 bar(g), 7 bar(g) to 30 bar(g), such as in non-limiting example 0 bar(g), 1 bar(g), 5 bar(g), 7 bar(g), 10 bar(g), 15 bar(g), 30 bar(g), 50 bar(g), 100 bar(g), 150 bar(g), 200 bar(g), 250 bar(g), 300 bar(g), 350 bar(g), 400 bar(g), 500 bar(g).

In an embodiment, the feed to hydroformylation having an internal olefin, or having a mixture of alpha olefins and internal olefins, can be hydroformylated at a CO/H2 molar ratio in a range of 10:1 to 1:10, such as 5:1, 2:1, 1.5:1, 1.1:1, 1.05:1, 1:1, 1:1.05, 1:1.1, 1:1.15, 1:1.2, 1:1.3, 1:1.5, 1:2, 1:3, 1:5 or 1:10.

In an embodiment, the feed to hydroformylation having an internal olefin, or having a mixture of alpha olefins and internal olefins, can be hydroformylated at a CO/H2 molar ratio in a range of 1.2:1 to 1:1.2.

In an embodiment, the feed having an alpha olefin, or having a mixture of linear olefins, can be hydroformylated at a pressure of 15 bar(g) and 90° C.

Stream 2 can also contain a small portion of mixed aldehydes of carbon number C5-C37 produced from hydroformylation of the C4-C36 alpha olefins and C4-C36 internal olefins. The production of aldehydes in Isomerization Reactor (100) is not an intended purpose but is to be expected to occur at low rates. Production of aldehydes in this step should be controlled at a low level as aldehydes formed in this step tend to be disproportionately linear aldehydes rather than the desired branched aldehydes.

Figure 2:
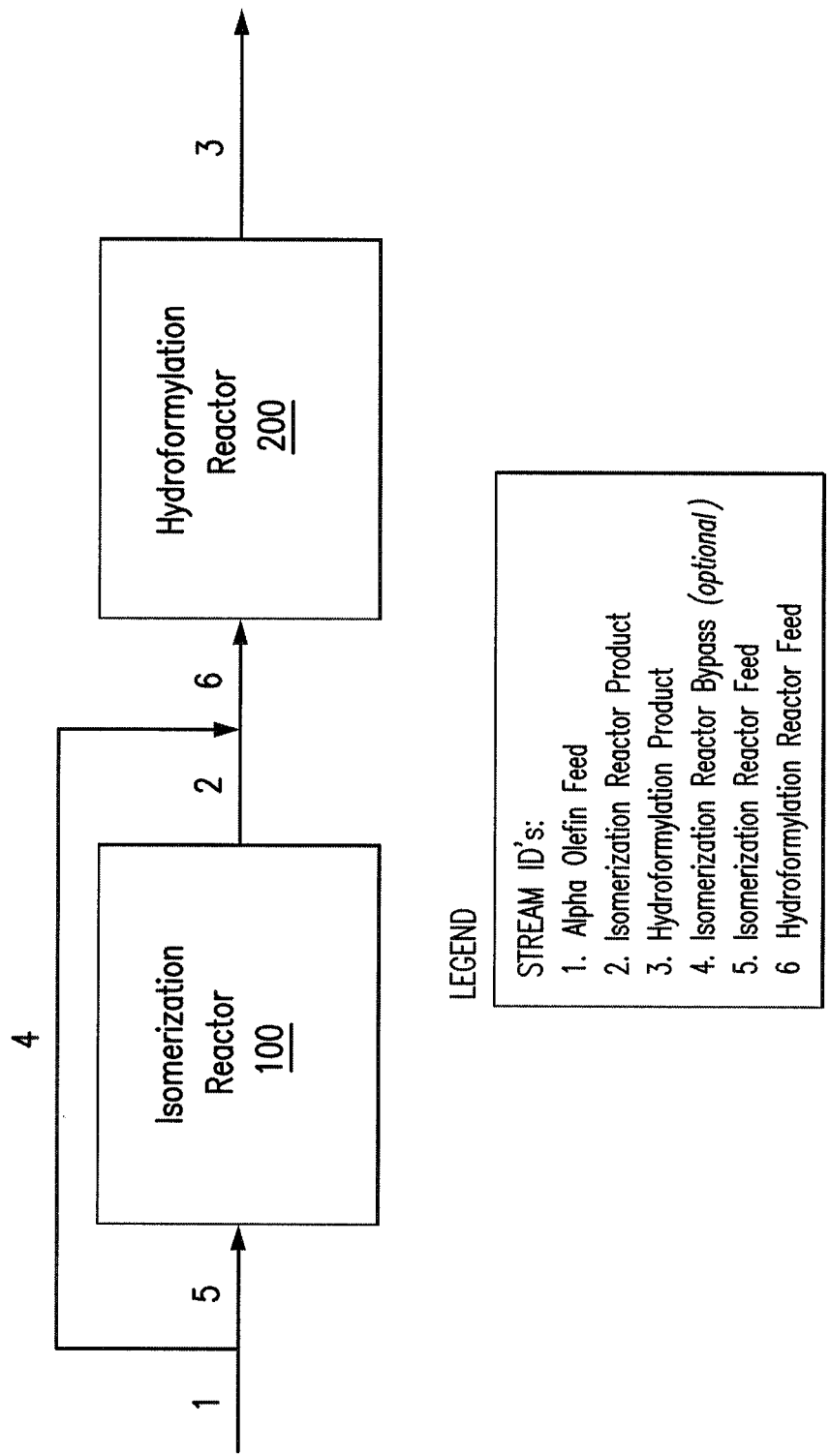
FIG. 2 shows an embodiment of a chemical manufacturing process having an isomerization reactor with an isomerization reactor bypass and a hydroformylation reactor.

FIG. 2 shows an embodiment of a chemical manufacturing process having an isomerization reactor 100 and which uses a Stream 4, which is optional, and which is an isomerization reactor bypass that can be used to control the feed composition to the hydroformylation reactor 200. In the embodiment of FIG. 2, isomerization reactor products Stream 2 is blended with the isomerization reactor bypass stream of Stream 4 to produce Stream 6 which is a hydroformylation reactor feed stream of the embodiment of FIG. 2.

FIG. 2 describes the two-step process of FIG. 1 in an embodiment that has Stream 4, which is an optional olefin bypass stream around Isomerization Reactor (100). In this manner a portion of Stream 1 can be bypassed around the Isomerization Reactor (100) as Stream 4 and a portion of Stream 1 is fed to Isomerization Reactor (100) as Stream 5. Stream 2 is the isomerized output of Isomerization Reactor (100) and is combined with Stream 4 to provide Stream 6, which is the reactor feed to Hydroformylation Reactor 200. The bypass functionality of Stream 4 provides a convenient and effective means to control the degree of olefin isomerization in the process. By adjusting the portion of Stream 1 that is isomerized (Stream 5) and the portion of Stream 1 that is not isomerized (Stream 4) the degree of olefin isomerization can be controlled to a specified, desired value. The degree of olefin isomerization is a key variable in determining the degree of aldehyde branching achieved. Thus, by controlling the degree of olefin isomerization, one can control the degree of aldehyde branching achieved in Stream 3 to a specified, desired value.

In the embodiment of FIG. 2, the compositions of Stream 1, the isomerization reactor bypass stream of Stream 4 and Stream 5 can be the same. As shown in FIG. 2, Stream 4 and Stream 5 are streams split from Stream 1.

Figure 3:
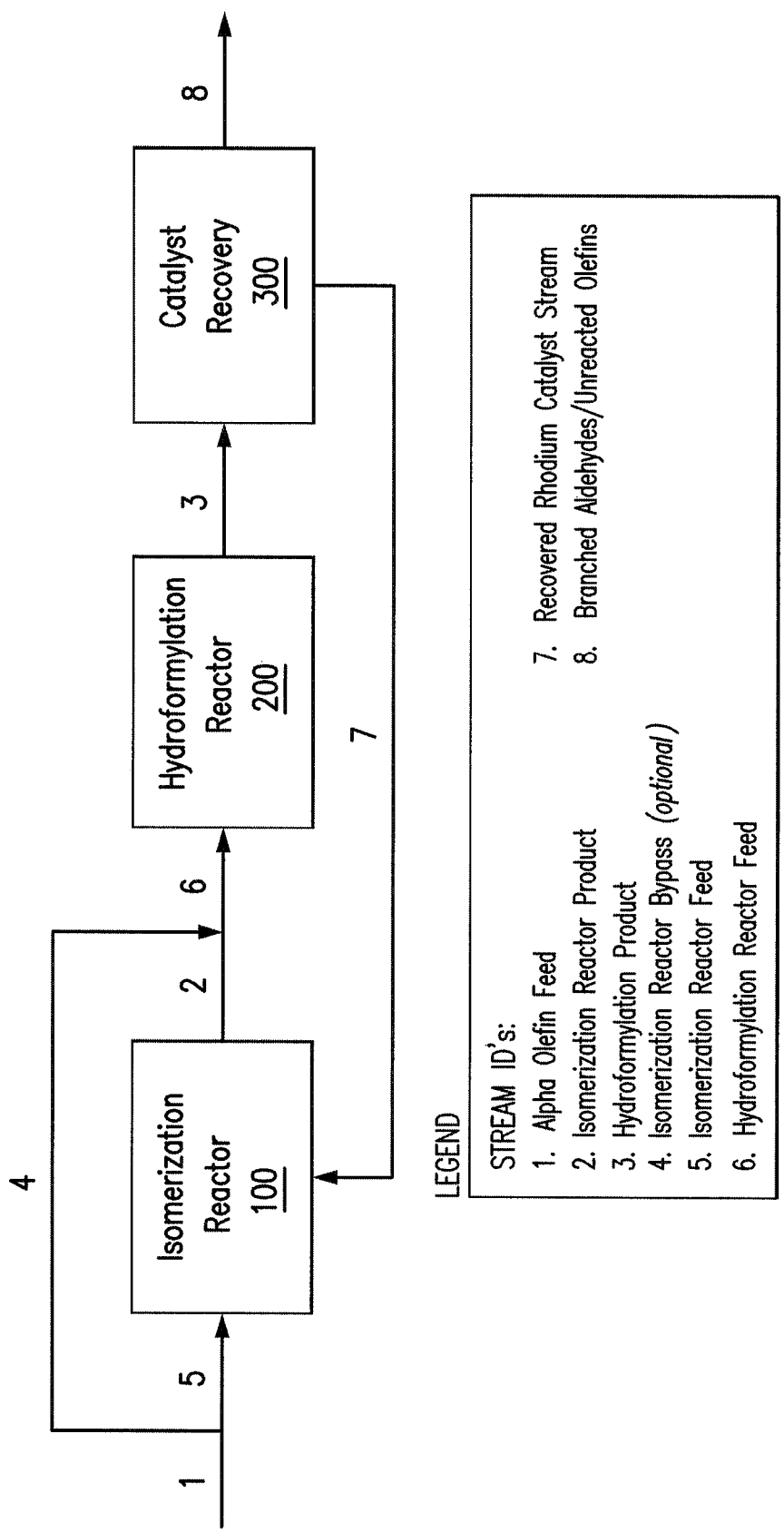
FIG. 3 shows an embodiment of a chemical manufacturing process having an isomerization reactor, a hydroformylation reactor and catalyst recovery.

Stream 1—Alpha Olefin Feed Composition
Stream 2—Isom. Reactor Product (>20% internal olefins) Composition
Stream 3—Hydroformylation Product (>25% branching) Composition
Stream 4—Isom. Reactor Bypass (optional) Composition
Stream 5—Isom. Reactor Feed Composition
Stream 6—Hydroformylation Reactor Feed Composition FIG. 3 shows an embodiment of a chemical manufacturing process having an isomerization reactor, a hydroformylation reactor and catalyst recovery. In this nonlimiting embodiment, the process of FIG. 2 is modified by the addition of a catalyst recovery step, i.e. Catalyst Recovery 300, which recovers the rhodium catalyst and produces Stream 7 which is a recovered rhodium catalyst stream that is recycled back to the isomerization reactor 100 and produces Stream 8 having a composition of branched aldehydes and unreacted olefins. Stream 8 is a branched aldehydes and unreacted olefins product stream.

FIG. 3 the process of FIG. 2 with the addition of catalyst recovery 300. Stream 3 is the reactor product of Hydroformylation Reactor 200 and has a stream 3 composition having:

A C5-C37 aldehyde mixture comprising:
>25 wt. % branched aldehydes, and
<75 wt. % linear aldehydes;
Unreacted C4-C36 olefins;
Unreacted CO/H2; and
Rhodium catalyst A.

In an embodiment the stream 3 composition can optionally comprise a high-boiling inert solvent.

In the Catalyst Recovery 300 step, unreacted CO/H2 gases are vented off, and the aldehyde mixture and unreacted olefins are distilled overhead under reduced pressure, for example <0.1 bar(absolute) and elevated temperature, for example 100-200° C., to produce overhead liquid Stream 8. In an embodiment, the olefins fed to hydroformylation reactor 200 are completely (or nearly completely) converted to aldehydes in Hydroformylation Reactor 200 and Stream 8 will be a mixed aldehyde product stream not requiring further purification.

In the embodiment of FIG. 3, the non-volatile liquid residue from Catalyst Recovery 300 is shown as Stream 7 which has the recovered rhodium Catalyst A and optionally the high-boiling inert solvent, if such solvent is used. Stream 7, the recovered rhodium catalyst stream, is then recycled back to isomerization reactor 100 for re-use in the process. While it is not required for the invention to include a high-boiling inert solvent in the system, it is often convenient to do so in order to provide a convenient liquid carrier for the recovered rhodium catalyst. Polyalphaolefins (PAO's) are an example of such a high boiling inert solvent. In an embodiment, Rhodium catalyst A can be an organometallic complex of rhodium and a water soluble organophosphorus ligand. In this embodiment, in the Catalyst Recovery 300 step, the catalyst can optionally be separated from the aldehyde product via an aqueous-organic extraction step, rather than via a distillation step. In an embodiment, optionally, one or more of an extraction and/or a distillation step can be used. In these embodiments, the rhodium catalyst can recovered in the aqueous phase and can form a recycle that can be recycled back to the isomerization reactor 100 for re-use in the process, and the aldehyde product and unreacted olefins can be recovered as an organic phase produced from the extraction step.

Stream 1—Alpha Olefin Feed Composition.
Stream 2—Isom. Reactor Product Composition.
Stream 3—Hydroformylation Product Composition.
Stream 4—Isom. Reactor Bypass Composition.
Stream 5—Isom. Reactor Feed Composition.
Stream 6—Hydroformylation Reactor Feed Composition.
Stream 7—Recovered Rhodium Catalyst Stream Composition.
Stream 8—Branched Aldehydes/Unreacted Olefins Composition.

Figure 4:
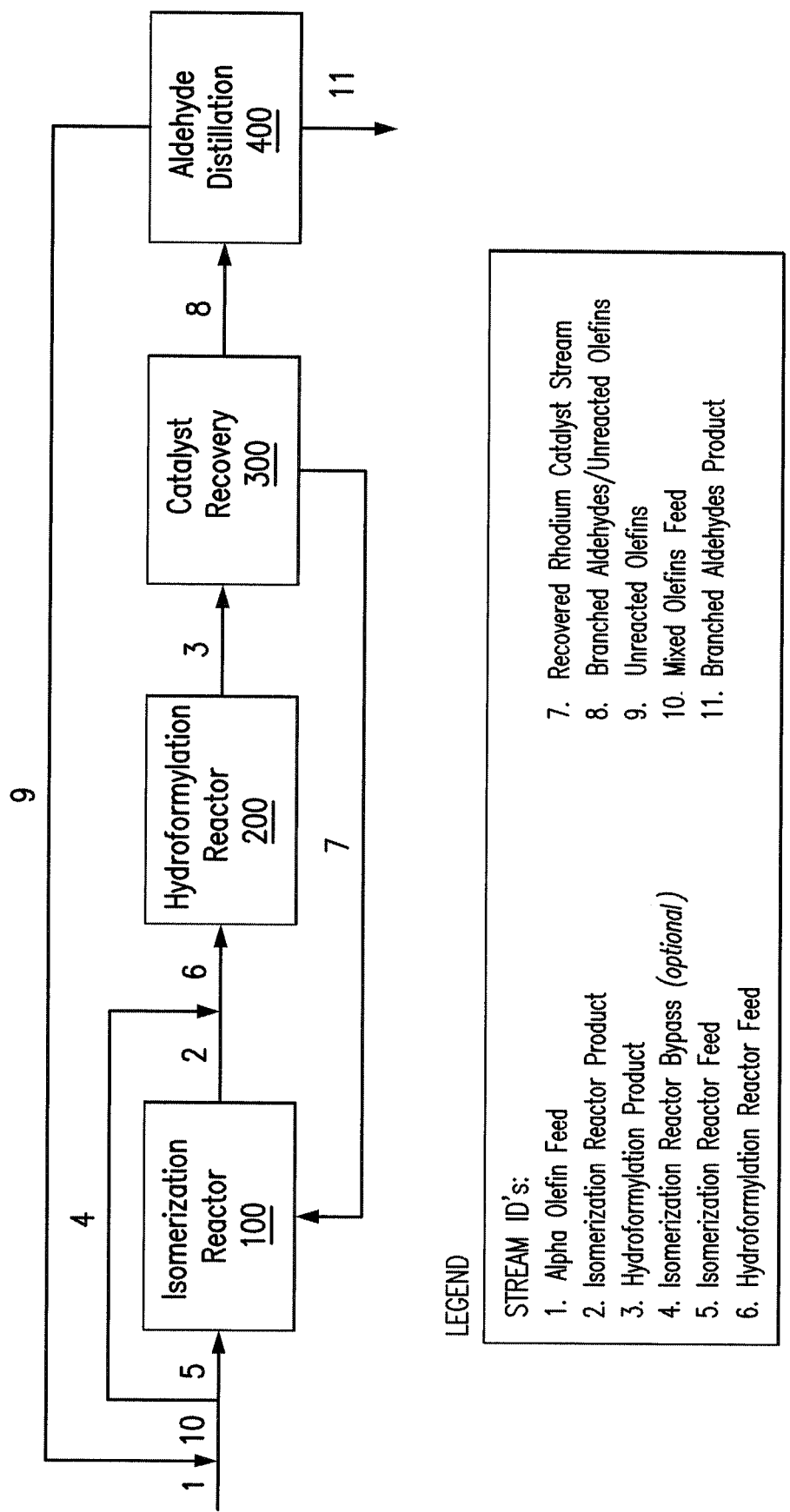
FIG. 4 shows an embodiment of a chemical manufacturing process having an isomerization reactor, a hydroformylation reactor, catalyst recovery and aldehyde distillation.

FIG. 4 shows the process of FIG. 3 to which an aldehyde distillation unit 400 has been added. FIG. 4 shows an embodiment of a chemical manufacturing process having an isomerization reactor, a hydroformylation reactor, catalyst recovery and aldehyde distillation.

FIG. 4 shows the process of FIG. 3 with the addition of an aldehyde distillation step shown an aldehyde distillation 400. In this embodiment, Stream 8 is the feed stream to Aldehyde Distillation (400) and can in an embodiment have a composition of, e.g.:

1. A C5-C37 aldehyde mixture comprising,
    >25 wt. % branched aldehydes,
    <75 wt. % linear aldehydes; and
2. Unreacted C4-C36 olefins.

In the embodiment of FIG. 4, during the distillation process of aldehyde distillation 400, unreacted C4-C36 olefins which were not converted to aldehydes in the hydroformylation reactor 200 are distilled overhead as a lights product shown as Stream 9 having unreacted olefin. The unreacted olefins of Stream 9 are recycled back to the beginning of the process and in the embodiment of FIG. 4 are blended with Stream 1. As shown, the unreacted olefins of Stream 9 are combined with the alpha olefin feed Stream 1 to create a Stream 10 which is a mixed olefins feed to the Isomerization Reactor 100.

In the embodiment of FIG. 4, the C5-C37 aldehyde mixture of Stream 8 produced by catalyst recovery 300 is further refined and purified by distillation in aldehyde distillation 400 to produce a distilled, high purity C5-C37 branched aldehyde product stream shown as Stream 11 which in an embodiment is free of, or nearly free of, unreacted C4-C36 olefins.

Stream 1—Alpha Olefin Feed Composition.
Stream 2—Isom. Reactor Product Composition.
Stream 3—Hydroformylation Product Composition.
Stream 4—Isom. Reactor Bypass Composition.
Stream 5—Isom. Reactor Feed Composition.
Stream 6—Hydroformylation Reactor Feed Composition.
Stream 7—Recovered Rhodium Catalyst Stream Composition.
Stream 8—Branched Aldehydes/Unreacted Olefins Composition.
Stream 9—Unreacted Olefins Composition.
Stream 10—Mixed Olefins Feed Composition.
Stream 11—Branched Aldehydes Product Composition.

Figure 5:
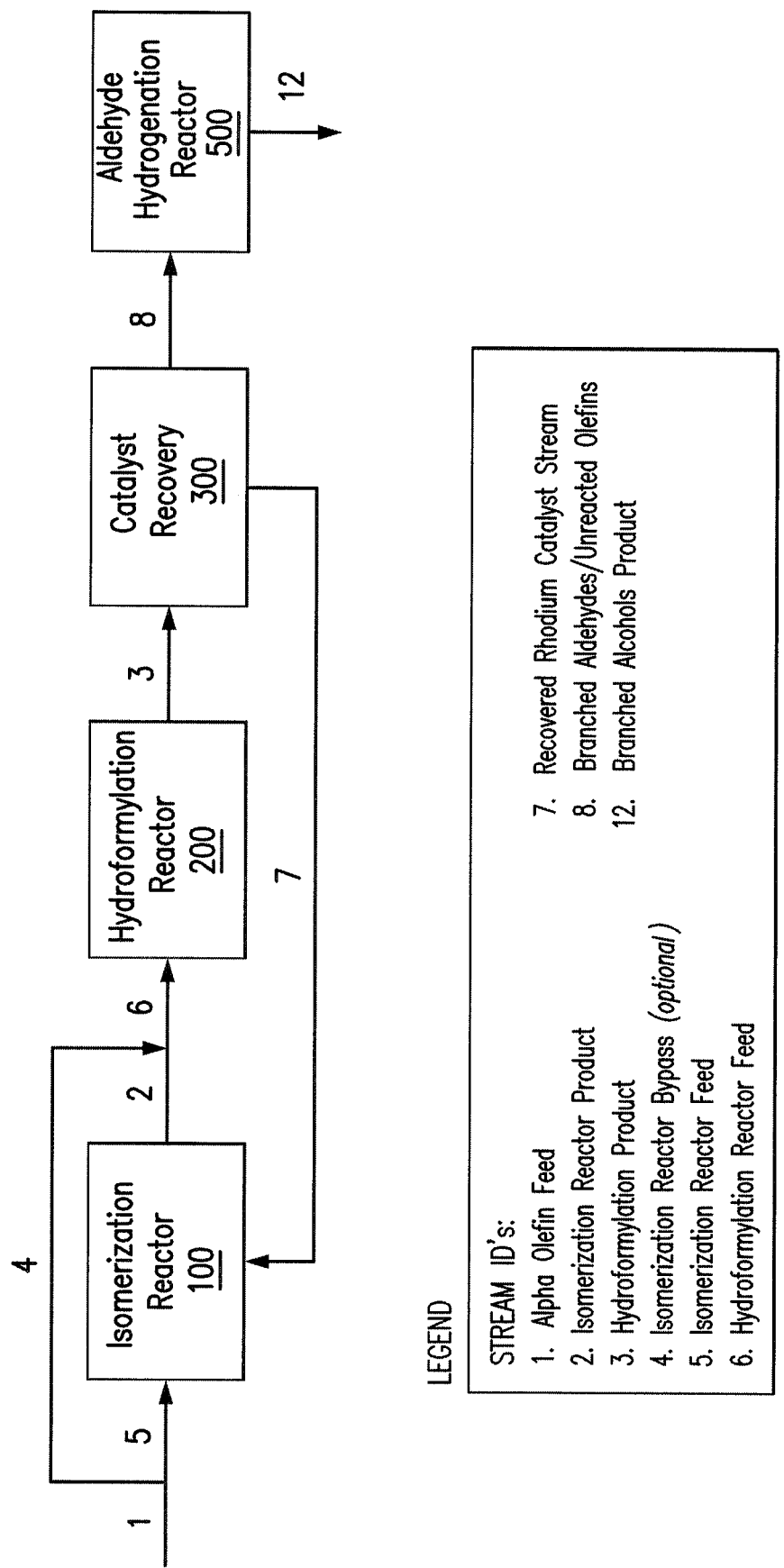
FIG. 5 shows an embodiment of a chemical manufacturing process having an isomerization reactor, a hydroformylation reactor, catalyst recovery and an aldehyde hydrogenation reactor.

FIG. 5 shows an embodiment of a chemical manufacturing process having an isomerization reactor, a hydroformylation reactor, catalyst recovery and an aldehyde hydrogenation reactor.

FIG. 5 shows a different embodiment modifying the process of FIG. 3 in which Stream 8 is fed to an aldehyde hydrogenation reactor 500 which produces branched alcohols as Stream 9 which is a branched alcohols product stream.

FIG. 5 shows the process of FIG. 3 with the addition of an aldehyde hydrogenation step shown as aldehyde hydrogenation reactor 500. In an embodiment, Stream 8 is the feed stream to the Aldehyde Hydrogenation Reactor (500) and can have a composition, e.g.:

1. A C5-C37 aldehyde mixture comprising,
    a. >25 wt. % branched aldehydes,
    b. <75 wt. % linear aldehydes, and
2. Unreacted C4-C36 olefins.

In the embodiment of FIG. 5, the C5-C37 aldehydes are hydrogenated in the Aldehyde Hydrogenation Reactor (500) in the presence of hydrogen and a hydrogenation catalyst, e.g. Catalyst A, to produce Stream 12.

Examples of suitable hydrogenation catalysts are supported base metal catalysts on high surface area supports such as ceramics, carbons, aluminas, silicas, titanias and zirconias, where the metal is affixed to and dispersed on the surface of the support such as those whose primary base metal components consist of nickel, cobalt, copper, manganese, molybdenum, zinc and/or iron or varied combinations thereof. As an example, for the base metal nickel: nickel on alumina catalysts, nickel on silica catalysts, nickel on titania catalysts, nickel on zirconia catalysts or nickel on carbon catalysts. Analogous supported metal catalysts can be found for the other base metals. Supported precious metal catalysts on high surface area supports such as ceramics, carbons, aluminas, silicas, titanias and zirconias, where the metal is affixed to and dispersed on the surface of the support, are also suitable, including those of whose metals consist of platinum, palladium, gold, silver, iridium and ruthenium or varied combinations thereof. As an example, for the precious metal platinum: platinum on carbon, platinum on silica, platinum on titania, platinum on zirconia or platinum on alumina catalysts. Analogous supported precious metal catalysts can be found for the other precious metals. Raney® nickel catalysts and Raney® cobalt catalysts from W. R. Grace & Co. (7500 Grace Drive, Columbia, Md. 21044, US, phone 1-410-531-4000) are also suitable hydrogenation catalysts. Suitable hydrogenation catalysts can either be finely divided slurry-type catalysts for use in stirred batch reactors or continuously stirred tank reactors (i.e. CSTR's) or can be fixed-bed type catalysts for use in reactors such as trickle-bed reactors.

Stream 12 is a branched alcohols product and in an embodiment can have a composition comprising:
1. A C5-C37 alcohol mixture comprising,
   a. >30 wt. % branched alcohols,
   b. <70 wt. % linear alcohols, and
2. C4-C36 paraffins (alkanes).

In the embodiment of FIG. 5, the C5-C37 alcohols are produced from the hydrogenation of the corresponding aldehydes in aldehyde hydrogenation reactor 500 and the C4-C36 paraffins also produced in aldehyde hydrogenation reactor 500 resulting from the hydrogenation of the unreacted C4-C36 olefins contained in Stream 8.

Optionally, the C5-C37 alcohols content (purity) can be increased in Stream 12, with a related decrease in the C4-C36 paraffin content by using an optional distillation step after aldehyde hydrogenation reactor 500 to remove the low-boiling C4-C36 paraffins and produce a distilled, high purity C5-C37 Branched Alcohols Product which is free of, or nearly free of, C4-C36 paraffins.

Stream 1—Alpha Olefin Feed Composition.
Stream 2—Isom. Reactor Product Composition.
Stream 3—Hydroformylation Product Composition.
Stream 4—Isom. Reactor Bypass Composition.
Stream 5—Isom. Reactor Feed Composition.
Stream 6—Hydroformylation Reactor Feed Composition.
Stream 7—Recovered Rhodium Catalyst Stream Composition.
Stream 8—Branched Aldehydes/Unreacted Olefins Composition.
Stream 12—Branched Alcohols Product.

In an embodiment, Stream 12 can be a branched alcohols product composition having greater than 25% branching.

Figure 6:
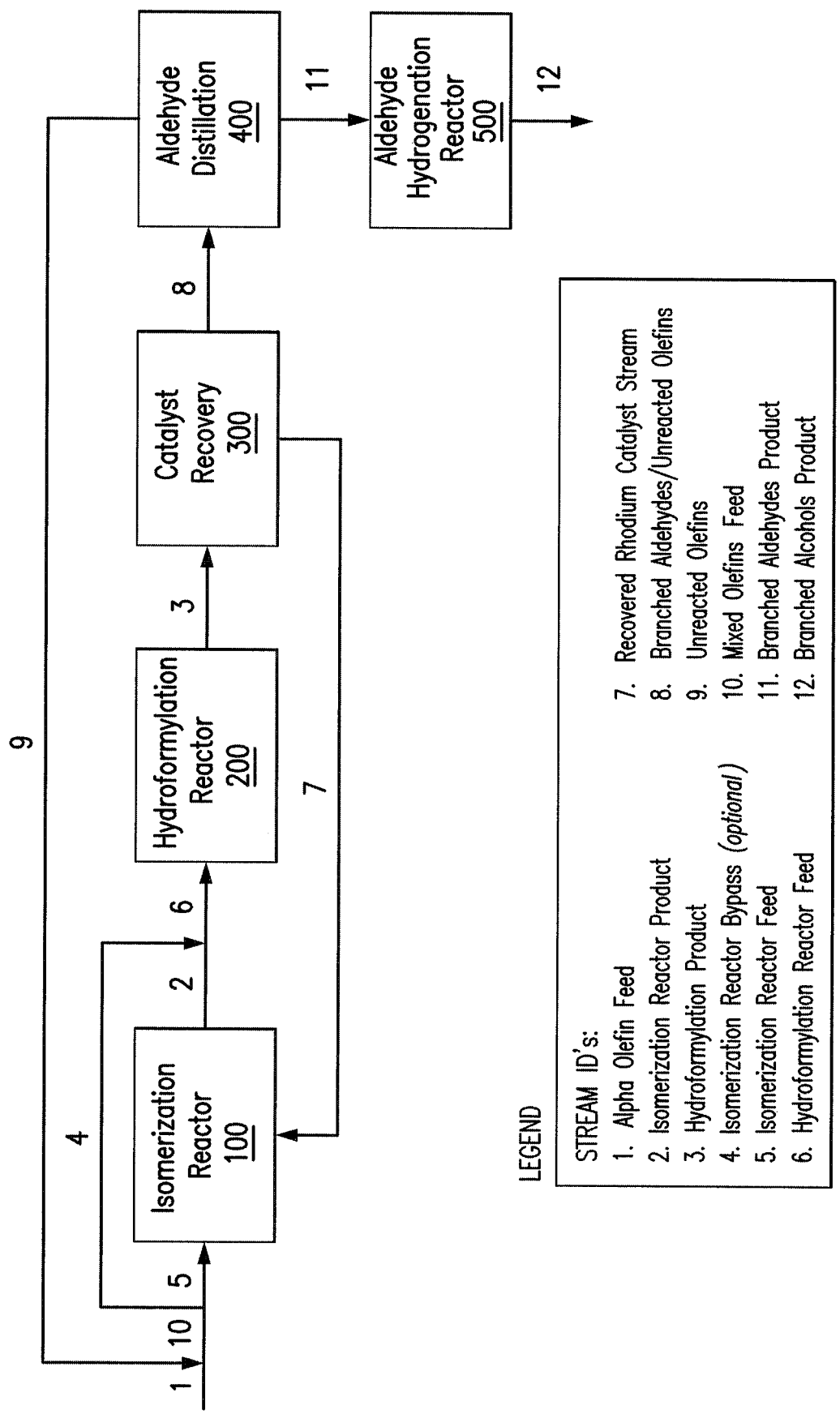
FIG. 6 shows an embodiment of a chemical manufacturing process having an isomerization reactor, a hydroformylation reactor, catalyst recovery, aldehyde distillation and an aldehyde hydrogenation reactor.

FIG. 6 shows an embodiment of a chemical manufacturing process having an isomerization reactor, a hydroformylation reactor, catalyst recovery, aldehyde distillation and an aldehyde hydrogenation reactor. FIG. 6 shows the process of FIG. 4 with the addition of an aldehyde hydrogenation reactor 500. In the embodiment of FIG. 6, Stream 11, the branched aldehyde product stream, is the feed stream to the Aldehyde Hydrogenation Reactor (500) and can have a C5-C37 aldehyde mixture comprising, e.g.:
1. >25 wt. % branched aldehydes, and
2. <75 wt. % linear aldehydes.

In the embodiment of FIG. 6, in the Aldehyde Hydrogenation Reactor (500), the C5-C37 aldehydes are hydrogenated in the presence of hydrogen and a hydrogenation catalyst, e.g. catalyst A, to produce Stream 12. Stream 12 is a branched alcohols product stream and can have a C5-C37 alcohol composition of, e.g.:
1. >30 wt. % branched alcohols, and
2. <70 wt. % linear alcohols.

In the embodiment of FIG. 6, the C5-C37 alcohols are produced from the hydrogenation of the corresponding aldehydes which are the reaction products of the hydroformylation reactor 200.

Optionally, the C5-C37 alcohols content (purity) in Stream 12 can be increased and the level of any undesired impurities decreased, for example low levels of C4-C36 paraffins, by adding a distillation step after aldehyde hydrogenation reactor 500 to remove such impurities and produce a purified, distilled C5-C37 Branched Alcohols Product.

Stream 1—Alpha Olefin Feed Composition.
Stream 2—Isom. Reactor Product Composition.
Stream 3—Hydroformylation Product Composition.
Stream 4—Isom. Reactor Bypass Composition.
Stream 5—Isom. Reactor Feed Composition.
Stream 6—Hydroformylation Reactor Feed Composition.
Stream 7—Recovered Rhodium Catalyst Stream Composition.
Stream 8—Branched Aldehydes/Unreacted Olefins Composition.
Stream 9—Unreacted Olefins Composition.
Stream 10—Mixed Olefins Feed Composition.
Stream 11—Branched Aldehydes Product Composition.
Stream 12—Branched Alcohols Product (>30% branching).

Example 1: Preparation of a Branched C13 Aldehyde Product

Introduction

In an embodiment, isomerization, hydroformylation and hydrogenation reactions produce two branched alcohol products based on two starting alpha olefins. Optionally a mixture of a number of alpha olefins can be used.

In an embodiment a first alpha olefin, 1-Dodecene, can be converted through the process chemistry described herewith to a mixture of branched tridecanols, while the second alpha olefin, 1-Tetradecene, is converted through analogous process chemistry to a mixture of branched pentadecanols.

The process can be run batchwise, or as a continuous process.

Batch Process Embodiment

In an embodiment, the first step in the process can be the batch-wise isomerization of the individual alpha olefins at moderate temperatures and pressures utilizing a homogeneous rhodium organophosphorus ligand catalyst system. The second step can be a hydroformylation with the same rhodium organophosphorus ligand catalyst system that proceeds with high yield and selectivity to the corresponding branched tridecanals and branched pentadecanals. For example, the branched tridecanals product from such an isomerization and hydroformylation process would yield a composition comprising a mixture of linear 1-tridecanal and 2-alkyl branched tridecanal isomers, i.e.:

TABLE 1

1-Dodecene Isomerization and Hydroformylation Reaction Products

No. 1  $CH_3-CH_2-CH_2-CH_2-CH_2-CH_2-CH_2-CH_2-CH_2-CH_2-CH_2-CH_2-CH$(=O)  1-Tridecanal  CAS No. 10486-19-8  $C_{13}H_{26}O$  MW 198.34

No. 2  $CH_3-CH_2-CH_2-CH_2-CH_2-CH_2-CH_2-CH_2-CH_2-CH_2-CH_2-CH(CH_3)-CH$(=O)  2-Methyl Dodecanal  CAS No. 37596-36-4  $C_{13}H_{26}O$  MW 198.34

TABLE 1-continued

1-Dodecene Isomerization and Hydroformylation Reaction Products

| No. 3 | CH$_3$–CH$_2$–CH$_2$–CH$_2$–CH$_2$–CH$_2$–CH$_2$–CH(O=CH)–CH$_2$–CH$_3$ | 2-Ethyl Undecanal<br>CAS No. 35518-76-4<br>$C_{13}H_{26}O$<br>MW 198.34 |
|---|---|---|
| No. 4 | CH$_3$–CH$_2$–CH$_2$–CH$_2$–CH$_2$–CH$_2$–CH(O=CH)–CH$_2$–CH$_3$ (propyl branch) | 2-Propyl Decanal<br>CAS No.<br>$C_{13}H_{26}O$<br>MW 198.34 |
| No. 5 | CH$_3$–CH$_2$–CH$_2$–CH$_2$–CH(O=CH)–CH$_2$–CH$_2$–CH$_3$ (butyl branch) | 2-Butyl Nonanal<br>CAS No. 65899-14-1<br>$C_{13}H_{26}O$<br>MW 198.34 |
| No. 6 | CH$_3$–CH$_2$–CH$_2$–CH$_2$–CH(O=CH)–CH$_2$–CH$_2$–CH$_2$–CH$_3$ (pentyl branch) | 2-Pentyl Octanal<br>CAS No.<br>$C_{13}H_{26}O$<br>MW 198.34 |

In an embodiment, the catalyst used in the isomerization and hydroformylation reactions is an organometallic rhodium ligand complex formed from Rh(CO)2ACAC ((Acetylacetonato)dicarbonylrhodium(I)) and tris (2,4,-di-t-butylphenyl) phosphite ligand.

After completion of the hydroformylation batch chemistry, the crude aldehydes can be flashed distilled to remove the high value catalyst ligand complex for recycle. The flashed aldehydes vapor can be fed directly to distillation to provide a high purity branched aldehyde intermediate.

In this embodiment, the branched tridecanals and pentadecanals can be separately batch hydrogenated at high pressures and moderate temperature in the presence of a hydrogenation catalyst such as a base metal catalyst, a supported nickel catalyst, a Raney® (W. R. Grace & Co., 7500 Grace Drive, Columbia, Md. 21044, US, phone 1-410-531-4000) nickel catalyst or a precious metal catalyst. During hydrogenation, the aldehyde functionality will be converted into the equivalent alcohol, producing the desired branched tridecanols and the desired branched pentadecanols.

In a batch reaction embodiment, the isomerization and hydroformylation reactions can be performed in the same or different reactors.

If the same reactor is used for both the isomerization and hydroformylation reactions, the isomerization can be executed under one set of reaction conditions and the hydroformylation can be executed under a different set of reaction conditions. The reaction temperatures of the isomerization and hydroformylation reactions can be the same or different. The reaction pressures of the isomerization and hydroformylation reactions can be the same or different. The molar ratio of CO:H2 in the isomerization and hydroformylation reactions can be the same or different. In one embodiment, the hydroformylation reaction is conducted at a higher pressure than the isomerization reaction.

In one embodiment, the batchwise hydroformylation reaction will be performed at moderate temperatures of 80° C. to 100° C. and at a moderate pressure of 15-20 bar(g). In this embodiment, the flash removal of the branched aldehydes can be performed in a flash unit operation, e.g. flash drum, optionally in conjunction with a distillation column. In another embodiment, the flash removal of the branched aldehydes can be performed in an evaporator unit operation, e.g. a wiped-film evaporator or a falling film evaporator, optionally in conjunction with a distillation column. The optional distillation can be performed at pressures including variable vacuums down from 1 millibar absolute to 999 millibar absolute, such as in nonlimiting example 5 millibar absolute, 10 millibar absolute, or 20 millibar absolute, or 50 millibar absolute, or 100 millibar absolute, or 500 millibar absolute, or higher.

In an embodiment the hydrogenation of the branched aldehyde intermediate(s) will be performed in a batch reactor at hydrogen pressures of between 10 bar(g) and 100 bar(g) e.g. 20 bar(g), 30 bar(g), 40 bar(g), 50 bar(g), 60 bar(g), 70 bar(g), 80 bar(g), 90 bar(g), or higher. This hydrogenation can be performed at temperatures between 50° C. and 300° C., e.g. 50° C., 100° C., 150° C., 200° C., 250° C., 300° C., 350° C., 400° C., 450° C.

In an embodiment, the reaction of the reactants will be considered complete once there is less than 1% of the Branched Aldehyde intermediate remaining. In an embodiment, the reaction of the reactants will be considered complete once there is less than 0.1% of the Branched Aldehyde intermediate remaining. In this embodiment, the filtered crude Branched Alcohol would be a low color, high purity (>97%), highly branched (>80%) product.

In an embodiment, branched alcohols products can be manufactured from the alpha olefin feeds through a batch isomerization process, a batch hydroformylation process, followed by flash distillation to produce the Branched Aldehydes intermediates. The Branched Aldehydes intermediates will then be batch hydrogenated and the product will be filtered to remove the hydrogenation catalyst to produce the finished Branched Alcohols.

Example 2: Preparation of a Branched C13 Alcohol Product

A C12 linear alpha olefin feedstock (1-Dodecene) was obtained from the Chevron Phillips Chemical Company LP, as identified by product name AlphaPlus® 1-Dodecene (Chevron Phillips Chemical Company LP, P.O. Box 4910, The Woodlands, Tex. 77387-4910, US, phone (800) 231-3260). The homogeneous rhodium organophosphorus catalyst used in this example is prepared in a high pressure, stainless steel stirred autoclave. To the autoclave was added 0.027 wt. % Rh(CO)2ACAC ((Acetylacetonato)dicarbonylrhodium(I)), 1.36 wt. % tris (2,4,-di-t-butylphenyl) phosphite ligand and 98.62 wt. % Synfluid® PAO 4 cSt (Chevron Phillips Chemical Company LP, P.O. Box 4910, The Woodlands, Tex. 77387-4910, phone (800) 231-3260) inert solvent. The mixture was heated at 80° C. in the presence of a CO/H2 atmosphere and 2 bar(g) pressure for four hours to produce the active rhodium catalyst solution (109 ppm rhodium, P:Rh molar ratio=20). The 1-Dodecene linear alpha olefin was added to the rhodium catalyst solution in the autoclave producing a starting reaction mixture with a rhodium concentration of 35 ppm. The alpha olefin feed was then isomerized at 80° C. in the presence of a CO/H2 atmosphere and 1 bar(g) pressure for 10 hours. The isomerized olefin was then hydroformylated at 70° C. in the presence of a CO/H2 atmosphere and 20 bar(g) pressure for 8 hours. The molar ratio of CO to 112 in both the isomerization step and the hydroformylation step was equal to 1:1.15. The resulting hydroformylation reaction product was flash distilled at 140-150° C. and 25 millibar absolute to recover the rhodium catalyst solution as a bottoms product and recover a branched C13 Aldehyde overheads product with a composition comprising:

|  | Weight % |
|---|---|
| 1-Tridecanal | 13.9% |
| 2-Methyl-dodecanal | 28.3% |
| 2-Ethyl-undecanal | 15.2% |
| 2-Propyl-decanal | 14.5% |
| 2-Butyl-nonanal | 13.6% |
| 2-Pentyl-octanal | 12.6% |
| TOTAL | 98.0% |

The weight % branching in the branched C13 aldehyde product was 86.2%. The weight % linear aldehydes is 14.2%. The weight % 2-methyl branched aldehydes was 28.9%. The weight % 2-ethyl branched aldehydes was 15.5%.

The branched C13 aldehyde product was hydrogenated in a high pressure, Inconel 625 stirred autoclave at 150 C and 20 bar(g) hydrogen pressure. The hydrogenation catalyst used was a Raney® Nickel 3111 (W. R. Grace & Co., 7500 Grace Drive, Columbia, Md. 21044, US, phone 1-410-531-4000) catalyst used at a 0.25 wt. % loading. The aldehyde was hydrogenated for 10 hours and the resultant reaction mixture was filtered to produce a branched C13 alcohol product comprising:

|  | Weight % |
|---|---|
| 1-Tridecanol | 13.2% |
| 2-Methyl-dodecanol | 29.1% |
| 2-Ethyl-undecanol | 15.5% |
| 2-Propyl-decanol | 14.4% |
| 2-Butyl-nonanol | 13.2% |
| 2-Pentyl-octanol | 12.9% |
| TOTAL | 98.4% |

The weight % branching in the branched C13 alcohol product was 86.6%. The weight % linear alcohols is 13.4%. The weight % 2-methyl branched alcohols was 29.6%. The weight % 2-ethyl branched alcohols was 15.8%.

Example 3: Preparation of a Branched C15 Alcohol Product

The recovered rhodium catalyst stream from Example 2 was charged to a high pressure, stainless steel stirred autoclave and a C14 linear alpha olefin feedstock (1-Tetradecene) from the Chevron Phillips Chemical Company LP, (AlphaPlus® 1-Tetradecene by Chevron Phillips Chemical Company LP, P.O. Box 4910, The Woodlands, Tex. 77387-4910, phone (800) 231-3260) was added. The resulting mixture had a rhodium concentration of approximately 30 ppm. The 1-tetradecene linear alpha olefin was then isomerized at 80° C. in the presence of a CO/H2 atmosphere and 1 bar(g) pressure for 12 hours. The isomerized olefin was then hydroformylated at 70° C. in the presence of a CO/H2 atmosphere and 20 bar(g) pressure for 8 hours. The resulting reaction product was flash distilled at 150-160° C. and 25 millibar absolute to recover the rhodium catalyst solution as a bottoms product and recover a branched C15 Aldehyde overheads product. The recovered rhodium catalyst solution was then used again to complete a second 1-tetradecene batch isomerization (4 hours) and hydroformylation (6 hours). The resulting C15 aldehyde products from the two batches were combined to give a branched C15 Aldehyde product comprising:

|  | Weight % |
|---|---|
| 1-Pentadecanal | 12.1% |
| 2-Methyl-tetradecanal | 34.1% |
| 2-Ethyl-tridecanal | 21.9% |
| 2-Propyl-dodecanal | 14.0% |
| 2-Butyl-undecanal | 8.6% |
| 2-Pentyl-decanal + 2-hexyl-nonanal | 9.0% |
| TOTAL | 99.6% |

The weight % branching in the branched C15 aldehyde product was 87.8%. The weight % linear aldehydes is 12.1%. The weight % 2-methyl branched aldehydes was 34.2%. The weight % 2-ethyl branched aldehydes was 22.0%.

The branched C15 aldehyde product was hydrogenated in a high pressure, Inconel 625 stirred autoclave at 150 C and 20 bar(g) hydrogen pressure. The hydrogenation catalyst used was a Raney® Nickel 3111 (W. R. Grace & Co., 7500 Grace Drive, Columbia, Md. 21044, US, phone 1-410-531-4000) catalyst used at a 0.25 wt. % loading. The aldehyde was hydrogenated for 10 hours and the resultant reaction mixture was filtered to produce a branched C15 alcohol product comprising:

|  | Weight % |
|---|---|
| 1-Pentadecanol | 13.7% |
| 2-Methyl-tetradecanol | 33.8% |
| 2-Ethyl-tridecanol | 21.4% |
| 2-Propyl-dodecanol | 12.4% |
| 2-Butyl-undecanol | 8.0% |
| 2-Pentyl-decanol + 2-hexyl-nonanol | 9.2% |
| TOTAL | 98.4% |

The weight % branching in the branched C15 alcohols product was 86.1%. The weight % linear alcohols is 13.9%. The weight % 2-methyl branched alcohols was 34.3%. The weight % 2-ethyl branched alcohols was 21.7%.

Example 4: Preparation of a Branched C15 Aldehyde Product

A C14 linear alpha olefin feedstock (1-Tetradecene) was obtained from the Chevron Phillips Chemical Company LP, as identified by product name AlphaPlus® 1-Tetradecene (Chevron Phillips Chemical Company LP, P.O. Box 4910, The Woodlands, Tex. 77387-4910, US, phone (800) 231-3260). The homogeneous rhodium organophosphorus catalyst used in this example is an organometallic complex of Rh(CO)2ACAC ((Acetylacetonato)dicarbonylrhodium(I)) and triphenylphosphine ligand. The 1-Tetradecene linear alpha olefin was added to the rhodium catalyst solution in a stainless steel autoclave producing a starting reaction mixture with a rhodium concentration of 35 ppm and a P:Rh molar ratio=20. The alpha olefin feed was then isomerized at 80° C. in the presence of a CO/H2 atmosphere and 1.5 bar(g) pressure for 3.5 hours. The isomerized olefin was then hydroformylated at 95° C. in the presence of a CO/H2 atmosphere and 14 bar(g) pressure for 9 hours. The molar ratio of CO to H2 in both the isomerization step and the hydroformylation step was equal to 1:1.15. The resulting hydroformylation reaction product was flash distilled at 140-150° C. and 5 millibar absolute to recover a branched C15 Aldehyde overheads product with aldehyde composition comprising:

|  | Weight % |
|---|---|
| 1-Pentadecanal | 52.5% |
| 2-Methyl-tetradecanal | 33.1% |
| 2-Ethyl-tridecanal | 10.8% |
| 2-Propyl-dodecanal | 1.6% |
| 2-Butyl-undecanal | 0.6% |
| 2-Pentyl-decanal + 2-hexyl-nonanal | 0.9% |
| TOTAL | 99.4% |

The weight % branching in the branched C15 aldehyde product was 47.2%. The weight % linear aldehydes is 52.8%. The weight % 2-methyl branched aldehydes was 33.3%. The weight % 2-ethyl branched aldehydes was 10.9%.

Figure 13:
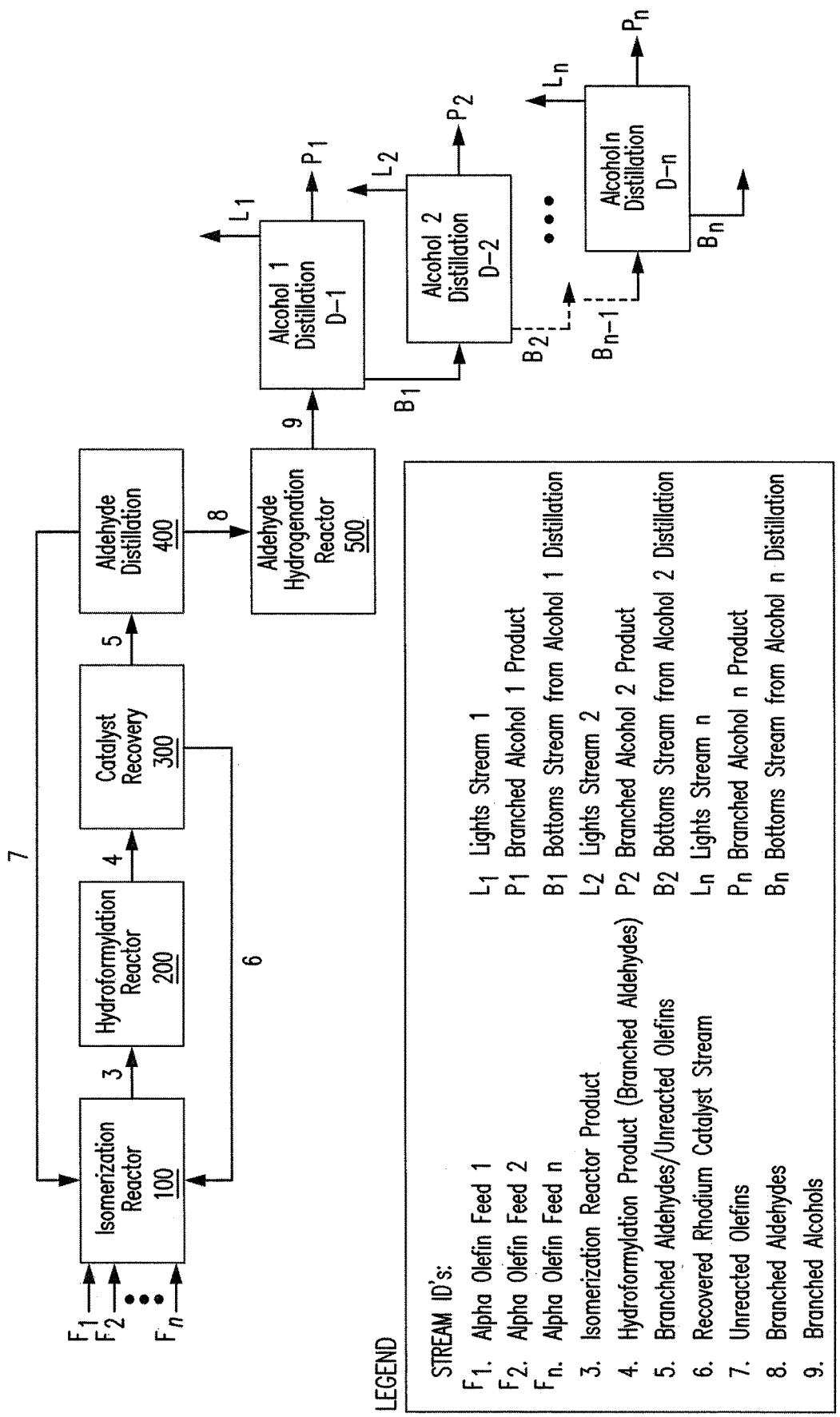
FIG. 13 shows an embodiment of a chemical manufacturing process showing a process with a number n variable alpha olefin feeds to an isomerization reactor, a hydroformylation reactor, catalyst recovery, aldehyde distillation, an aldehyde hydrogenation reactor as well as n alcohol distillation unit operations to produce n branched alcohol products.

FIG. 13 shows an embodiment of a chemical manufacturing process showing a process with a number n variable alpha olefin feeds to an isomerization reactor, a hydroformylation reactor, catalyst recovery, aldehyde distillation, an aldehyde hydrogenation reactor as well as n alcohol distillation unit operations to produce n branched alcohol products. In the embodiment of FIG. 13, n alpha olefin feeds designated as $F_1$, $F_2$ . . . $F_n$ are fed to Isomerization Reactor 100 to produce an Isomerized Reactor Product Stream 3 comprising n isomerized olefins Stream 3 is fed to Hydroformylation Reactor 200 to produce Stream 4 which is a mixture of n branched aldehydes. In the Catalyst Recovery 300 step, the mixture of n branched aldehydes and unreacted olefins are distilled overhead to produce overhead Stream 5, while the rhodium catalyst stream is recovered as bottoms product stream 6 which is recycled back to Isomerization Reactor 100 for re-use in the process. In the Aldehyde Distillation 400 step, the unreacted olefins which were not converted to aldehydes in the Hydroformylation Reactor 200 are distilled overhead and recovered as a lights product shown as Stream 7 comprising unreacted olefins. These unreacted olefins are recycled back to the beginning of the process to undergo additional reaction processes to produce additional aldehyde products. In the embodiment of FIG. 13, Stream 8 which is produced in the Aldehyde Distillation 400 step comprises a distilled, high purity mixture of n branched aldehydes, which in an embodiment is free of, or nearly free of, unreacted olefins.

In the embodiment of FIG. 13, in the Aldehyde Hydrogenation Reactor (500), the mixture of n branched aldehydes are hydrogenated in the presence of hydrogen and a hydrogenation catalyst to produce Stream 9, which is a reaction product stream comprising a mixture of n branched alcohols. In an embodiment, each of the n branched alcohols produced from hydrogenation of the corresponding n branched aldehydes and can have an alcohol isomer composition of, e.g.:
1. >30 wt. % branched alcohols, and
2. <70 wt. % linear alcohols.

In the embodiment of FIG. 13, the mixture of n branched alcohols (Stream 9) from the Aldehyde Hydrogenation Reactor 500 is fed to Alcohol 1 Distillation unit operation D-1 where the low boiling impurities are removed as Lights Stream $L_1$, the Branched Alcohol 1 is recovered as a refined, purified Branched Alcohol Product $P_1$ and the Bottoms stream from Alcohol 1 Distillation unit operation D-1 (Stream $B_1$), is fed to Alcohol 2 Distillation unit operation D-2. In Alcohol 2 Distillation unit operation D-2, the low boiling impurities are removed as Lights Stream $L_2$, the Branched Alcohol 2 is recovered as a refined, purified Branched Alcohol Product $P_2$ and the Bottoms stream from Alcohol 2 Distillation unit operation D-2 is recovered as Stream $B_2$. In an analogous manner, each of the n branched alcohols contained in the mixed branched alcohols product from the Aldehyde Hydrogenation Reactor 500 (Stream 9) is refined in a distillation unit operation to produce n purified Branched Alcohol Products.

FIG. 13 shows the following streams:
Stream $F_1$—Alpha Olefin Feed 1;
Stream $F_2$—Alpha Olefin Feed 2;
Stream $F_n$—Alpha Olefin Feed n;
Stream 3—Isomerization Reactor Product;
Stream 4—Hydroformylation Product (Branched Aldehydes);
Stream 5—Branched Aldehydes/Unreacted Olefins;
Stream 6—Recovered Rhodium Catalyst Stream;
Stream 7—Unreacted Olefins;
Stream 8—Branched Aldehydes;
Stream 9—Crude Branched Alcohols;
Stream $L_1$—Lights Stream 1;
Stream $P_1$—Branched Alcohol 1 Product;
Stream $B_1$—Bottoms Stream from Alcohol 1 Distillation;
Stream $L_2$—Lights Stream 2;
Stream $P_2$—Branched Alcohol 2 Product;
Stream $B_2$—Bottoms Stream from Alcohol 2 Distillation;
Stream $L_n$—Lights Stream n;
Stream $P_n$—Branched Alcohol n Product; and
Stream $B_n$—Bottoms Stream from Alcohol n Distillation.

Figure 14:
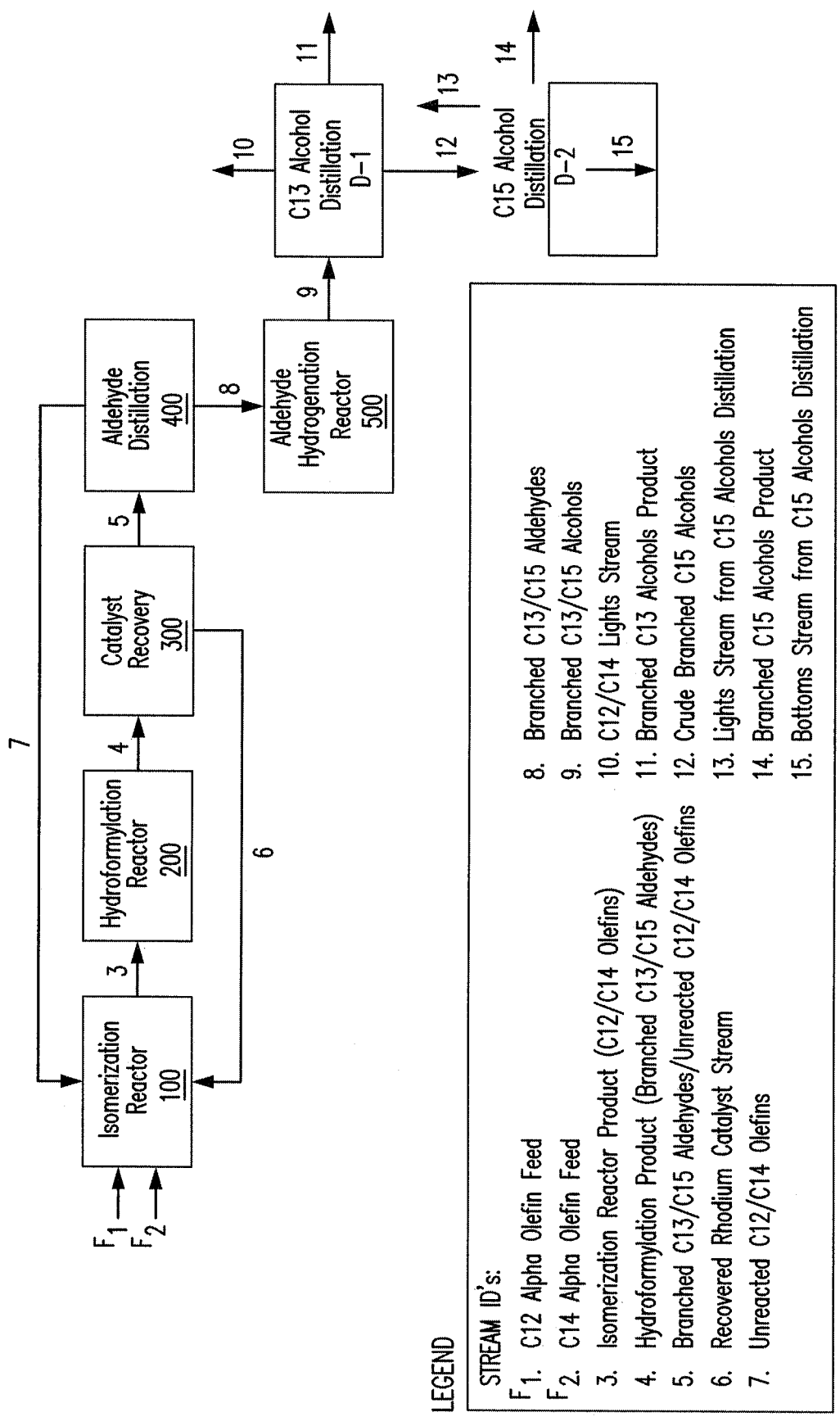
FIG. 14 shows an embodiment of a chemical manufacturing process showing C12 and C14 alpha olefin feed streams to an isomerization reactor, a hydroformylation reactor, catalyst recovery, aldehyde distillation, an aldehyde hydrogenation reactor, as well as a branched C13 alcohol distillation unit operation and a branched C15 alcohol distillation unit operation.

FIG. 14 describes an embodiment of the chemical manufacturing process described in FIG. 13 where the number of alpha olefin feeds n equals two. Specifically, the first alpha olefin feed, $F_1$, is a C12 Alpha olefin (i.e. 1-dodecene) and the second alpha olefin feed, $F_2$, is a C14 Alpha olefin (i.e. 1-tetradecene) 1. These two alpha olefin feeds are fed to Isomerization Reactor 100 to produce an Isomerized Reactor Product Stream 3 comprising isomerized C12 olefins and isomerized C14 olefins. Stream 3 is fed to Hydroformylation Reactor 200 to produce Stream 4 which is a mixture of C13 branched aldehydes and C15 branched aldehydes. In the Catalyst Recovery 300 step, the mixture of C13 and C15 branched aldehydes and unreacted C12/C14 olefins are distilled overhead to produce overhead Stream 5, while the rhodium catalyst stream is recovered as bottoms product stream 6 which is recycled back to Isomerization Reactor 100 for re-use in the process. In the Aldehyde Distillation 400 step, the unreacted C12/C14 olefins are distilled overhead and recovered as a lights product shown as Stream 7 comprising unreacted C12/C14 olefins. These unreacted C12/C14 olefins are recycled back to the beginning of the process to undergo additional reaction processes to produce additional branched C13 aldehydes and branched C15 aldehydes. In the embodiment of FIG. 14, Stream 8 which is produced in the Aldehyde Distillation 400 step comprises a distilled, high purity mixture of C13 branched aldehydes and C15 branched aldehydes, which in an embodiment is free of, or nearly free of, unreacted C12/C14 olefins.

In the embodiment of FIG. 14, in the Aldehyde Hydrogenation Reactor (500), the mixture of branched C13 aldehydes and branched C15 aldehydes are hydrogenated in the presence of hydrogen and a hydrogenation catalyst to produce Stream 9, which is a reaction product stream comprising a mixture of C13 branched alcohols and C15 branched alcohols. In an embodiment, the C13 branched alcohols produced from hydrogenation of the corresponding branched C13 aldehydes can have a C13 alcohol isomer composition of, e.g.:
1. >30 wt. % branched C13 alcohols, and
2. <70 wt. % linear C13 alcohols.

In an embodiment, the C15 branched alcohols produced from hydrogenation of the corresponding branched C15 aldehydes can have a C15 alcohol isomer composition of, e.g.:
3. >30 wt. % branched C15 alcohols, and
4. <70 wt. % linear C15 alcohols.

In the embodiment of FIG. 14, the mixture of C13 branched alcohols and C15 branched alcohols (Stream 9) from the Aldehyde Hydrogenation Reactor 500 is fed to the C13 Alcohol Distillation unit operation D-1 where the low boiling impurities are removed as Lights Stream 10, the Branched C13 Alcohol is recovered as a refined, purified Branched C13 Alcohol Product Stream 11 and the Bottoms stream from the C13 Alcohol Distillation unit operation D-1 (Stream 12), is fed to C15 Alcohol Distillation unit operation D-2. In the C15 Alcohol Distillation unit operation D-2, the low boiling impurities are removed as Lights Stream 13, the Branched C15 Alcohol is recovered as a refined, purified Branched C15 Alcohol Product Stream 14 and the Bottoms stream from C15 Alcohol Distillation unit operation D-2 is recovered as Stream 15.

FIG. 14 shows the following streams:
Stream $F_1$—C12 Alpha Olefin Feed;
Stream $F_2$—C14 Alpha Olefin Feed;
Stream 3—Isomerization Reactor Product (C12/C14 Isomerized Olefins);
Stream 4—Hydroformylation Product (Branched C13/C15 Aldehydes);
Stream 5—Branched C13/C15 Aldehydes/Unreacted C12/C15 Olefins;
Stream 6—Recovered Rhodium Catalyst Stream;
Stream 7—Unreacted C12/C14 Olefins;
Stream 8—Branched C13/C15 Aldehydes;
Stream 9—Branched C13/C15 Alcohols;
Stream 10—C12/C14 Lights Stream;
Stream 11—Branched C13 Alcohols Product;
Stream 12—Crude Branched C15 Alcohols;
Stream 13—Lights Stream from C15 Alcohols Distillation;
Stream 14—Branched C15 Alcohols Product; and
Stream 15—Bottoms Stream from C15 Alcohols Distillation.

Figure 15:
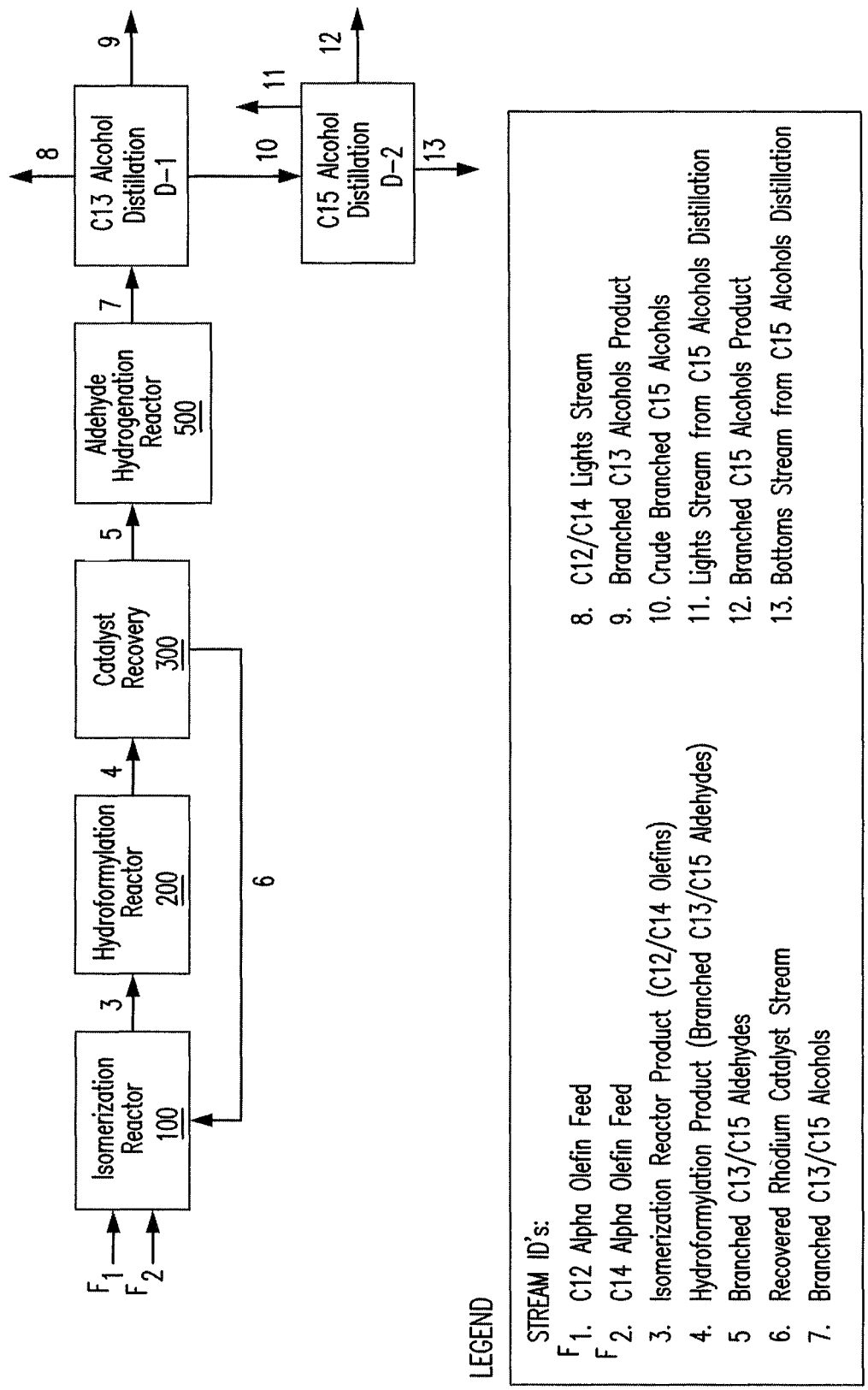
FIG. 15 shows an embodiment of a chemical manufacturing process having an isomerization reactor, a hydroformylation reactor, catalyst recovery, an aldehyde hydrogenation reactor, as well as a branched C13 alcohol distillation unit operation and a branched C15 alcohol distillation unit operation.

FIG. 15 shows an embodiment of the chemical manufacturing process described in FIG. 14 having an isomerization reactor, a hydroformylation reactor, catalyst recovery, an aldehyde hydrogenation reactor, a C13 alcohol distillation unit operation and a C15 alcohol distillation unit operation. In this embodiment, however, there is no Aldehyde Distillation unit and therefore no recovery and recycle back of the unreacted C12/C14 olefins. In this embodiment, the Hydroformylation Reactor 200 is operated such that the hydroformylation reaction converting the isomerized C12/C14 olefins to branched C13 aldehydes and branched C15 aldehydes is run to a very high chemical conversion of the C12/C14 olefins, e.g. to greater than 90% conversion, or greater than 95% conversion, or greater than 98% conversion. In this manner, there only remains a low concentration of unreacted C12/C14 olefins in the hydroformylation product (Stream 4) and the necessity of the Aldehyde Distillation step is eliminated. In the Catalyst Recovery 300 step, the rhodium catalyst stream is recovered as bottoms product stream 6 and the mixture of C13 and C15 branched aldehydes and low levels of unreacted C12/C14 olefins are distilled overhead as Stream 5. In the embodiment of FIG. 15, in the Aldehyde Hydrogenation Reactor (500), the mixture of branched C13 aldehydes and branched C15 aldehydes and low levels of unreacted C12/C14 olefins are hydrogenated in the presence of hydrogen and a hydrogenation catalyst to produce Stream 7, which is a reaction product stream comprising a mixture of C13 branched alcohols, C15 branched alcohols as well as low levels of C12 alkanes (dodecanes) and C14 alkanes (tetradecanes). These C12 alkanes and C14 alkanes are formed from the hydrogenation of the corresponding C12 and C14 alkenes. In an embodiment, the C13 branched alcohols in Stream 7 produced from hydrogenation of the corresponding branched C13 aldehydes can have a C13 alcohol isomer composition of, e.g.:
5. >30 wt. % branched C13 alcohols, and
6. <70 wt. % linear C13 alcohols.

In an embodiment, the C15 branched alcohols in Stream 7 produced from hydrogenation of the corresponding branched C15 aldehydes can have a C15 alcohol isomer composition of, e.g.:
7. >30 wt. % branched C15 alcohols, and
8. <70 wt. % linear C15 alcohols.

In the embodiment of FIG. 15, the mixture of C13 branched alcohols, C15 branched alcohols and low levels of C12 and C14 alkanes (Stream 7) from the Aldehyde Hydrogenation Reactor 500 is fed to the C13 Alcohol Distillation unit operation D-1. In this unit operation step, the C12 alkanes and C14 alkanes are removed as low boiling impurities in Lights Stream 8, the Branched C13 Alcohol is recovered as a refined, purified Branched C13 Alcohol Product Stream 9 and the Bottoms stream from the C13 Alcohol Distillation unit operation D-1 (Stream 10), is fed to C15 Alcohol Distillation unit operation D-2. In the C15 Alcohol Distillation unit operation D-2, the low boiling impurities are removed as Lights Stream 11, the Branched C15 Alcohol is recovered as a refined, purified Branched C15 Alcohol Product Stream 12 and the Bottoms stream from C15 Alcohol Distillation unit operation D-2 is recovered as Stream 13.

FIG. 15 shows the following streams:
Stream $F_1$—C12 Alpha Olefin Feed;
Stream $F_2$—C14 Alpha Olefin Feed;
Stream 3—Isomerization Reactor Product (C12/C14 Isomerized Olefins);
Stream 4—Hydroformylation Product (Branched C13/C15 Aldehydes);
Stream 5—Branched C13/C15 Aldehydes/Unreacted C12/C15 Olefins;

Stream 6—Recovered Rhodium Catalyst Stream;
Stream 7—Branched C13/C15 Alcohols and C12/C14 Alkanes;
Stream 8—C12 Alkanes/C14 Alkanes Lights Stream;
Stream 9—Branched C13 Alcohols Product;
Stream 10—Crude Branched C15 Alcohols;
Stream 11—Lights Stream from C15 Alcohols Distillation;
Stream 12—Branched C15 Alcohols Product; and
Stream 13—Bottoms Stream from C15 Alcohols Distillation.

Figure 16:
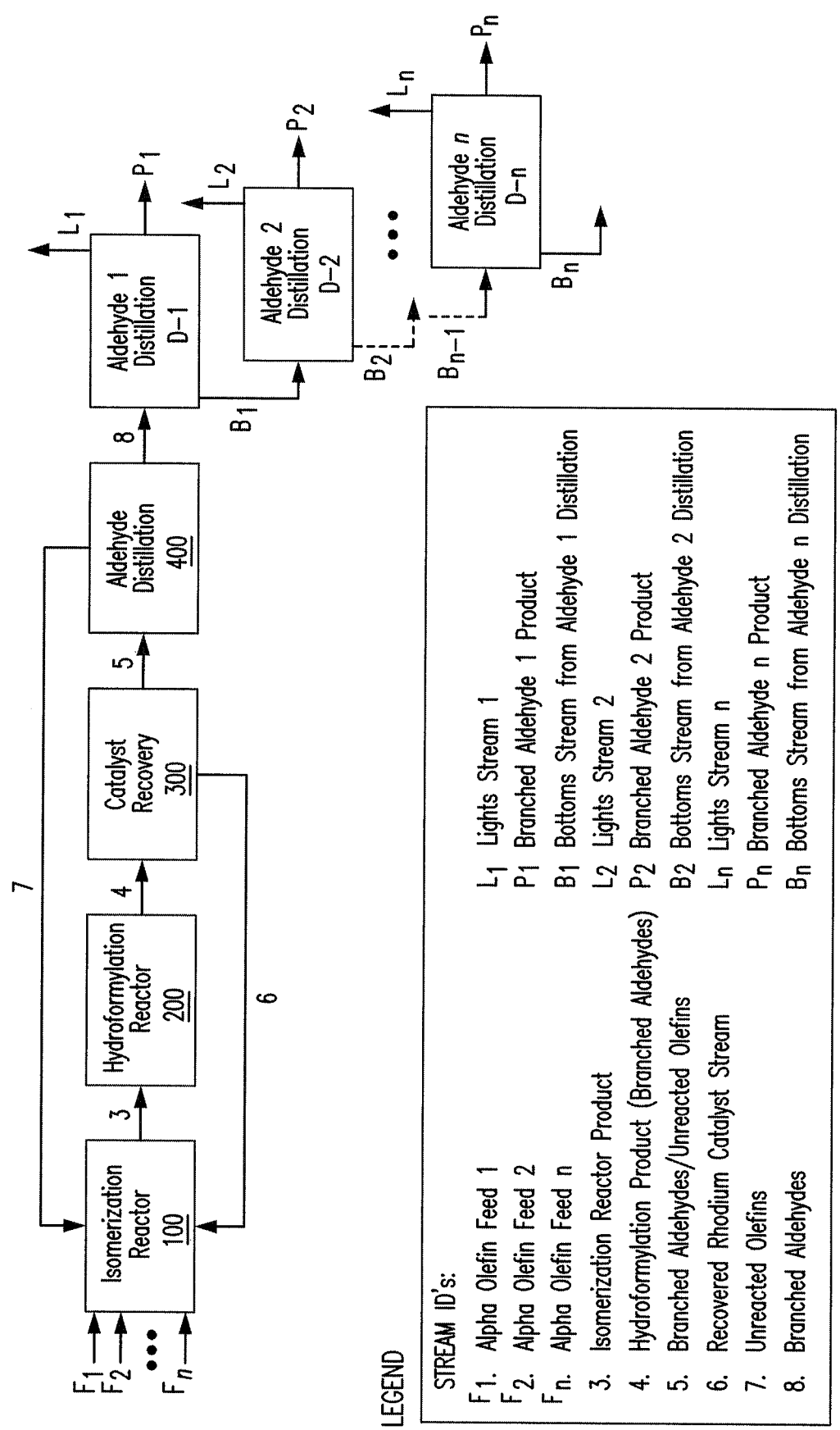
FIG. 16 shows an embodiment of a chemical manufacturing process showing a process with a number n variable alpha olefin feeds to an isomerization reactor, a hydroformylation reactor, catalyst recovery, aldehyde distillation, as well as n aldehyde distillation unit operations to produce n branched aldehyde products.

FIG. 16 shows an embodiment of the chemical manufacturing process described in FIG. 13 however in this embodiment the final products of the process are n branched aldehyde products rather than n branched alcohol products as described in FIG. 13. This embodiment would be preferred when one desired branched aldehydes as the products. This would be advantageous if purified branched aldehydes were desired as the final products to be used (for example, fragrance applications) or if the purified branched aldehydes were desired as intermediates to make other valuable derivatives such as branched amines, or branched carboxylic acids. The embodiment shown in FIG. 16 describes a chemical manufacturing process showing a process with a number n variable alpha olefin feeds to an isomerization reactor, a hydroformylation reactor, catalyst recovery, aldehyde distillation, as well as n aldehyde distillation unit operations to produce n branched aldehyde products. This process produces a distilled, high purity mixture of n branched aldehydes from the Aldehyde Distillation 400 as Stream 8 in a directly analogous manner as the process shown in FIG. 13. In an embodiment, Stream 8 is free of, or nearly free of, unreacted olefins. In the embodiment of FIG. 16, Stream 8 is fed directly to a series of Aldehyde Distillation unit operations rather than being hydrogenated to alcohols. In the embodiment of FIG. 16, the mixture of n branched aldehydes (Stream 8) from is fed to Aldehyde 1 Distillation unit operation D-1 where the low boiling impurities are removed as Lights Stream $L_1$, the Branched Aldehyde 1 is recovered as a refined, purified Branched Aldehyde Product $P_1$ and the Bottoms stream from Aldehyde 1 Distillation unit operation D-1 (Stream $B_1$), is fed to Aldehyde 2 Distillation unit operation D-2. In Aldehyde 2 Distillation unit operation D-2, the low boiling impurities are removed as Lights Stream $L_2$, the Branched Aldehyde 2 is recovered as a refined, purified Branched Aldehyde Product $P_2$ and the Bottoms stream from Aldehyde 2 Distillation unit operation D-2 is recovered as Stream $B_2$. In an analogous manner, each of the n branched aldehydes contained in the mixed branched aldehydes Stream 8 is refined in a distillation unit operation to produce n purified Branched Aldehyde Products.

FIG. 16 shows the following streams:
Stream $F_1$—Alpha Olefin Feed 1;
Stream $F_2$—Alpha Olefin Feed 2;
Stream $F_n$—Alpha Olefin Feed n;
Stream 3—Isomerization Reactor Product;
Stream 4—Hydroformylation Product (Branched Aldehydes);
Stream 5—Branched Aldehydes/Unreacted Olefins;
Stream 6—Recovered Rhodium Catalyst Stream;
Stream 7—Unreacted Olefins;
Stream 8—Branched Aldehydes;
Stream $L_1$—Lights Stream 1;
Stream $P_1$—Branched Aldehyde 1 Product;
Stream $B_1$—Bottoms Stream from Aldehyde 1 Distillation;
Stream $L_2$—Lights Stream 2;
Stream $P_2$—Branched Aldehyde 2 Product;
Stream $B_2$—Bottoms Stream from Aldehyde 2 Distillation;
Stream $L_n$—Lights Stream n;
Stream $P_n$—Branched Aldehyde n Product; and
Stream $B_n$—Bottoms Stream from Aldehyde n Distillation.

Introduction to Examples 5-7

Examples 5-7 are examples demonstrating the co-production of branched C13 aldehydes and branched C15 aldehydes, as well as demonstrating the co-production of branched C13 alcohols and branched C15 alcohols. Example 5 provides a first example of a two-step process for the coproduction of branched C13 aldehydes and branched C15 aldehydes from a starting alpha olefin feed comprising a 50:50 mixture of 1-dodecene and 1-tetradecene. Example 6 provides a second example of a two-step process for the coproduction of branched C13 aldehydes and branched C15 aldehydes from a 50:50 mixture of 1-dodecene and 1-tetradecene, wherein the degree of isomerization was increased, producing an aldehyde product with an increased degree of branching. In Example 7, the branched C13 aldehydes and branched C15 aldehydes produced in examples 5 and 6 were hydrogenated to produce a mixture of branched C13 alcohols and branched C15 alcohols.

Example 5: Production of Branched C13 Aldehydes and Branched C15 Aldehydes

A C12 linear alpha olefin feedstock (1-Dodecene) and a C14 linear alpha olefin feedstock (1-Tetradecene) were obtained from the Chevron Phillips Chemical. Company LP, respectively identified by product names AlphaPlus® 1-Dodecene and AlphaPlus® 1-Tetradecene (Chevron Phillips Chemical Company LP, P.O. Box 4910, The Woodlands, Tex. 77387-4910, US, phone (800) 231-3260). The homogeneous rhodium organophosphorus catalyst solution used in this Example 5 was a mixture comprised of 0.040 wt. % Rh(O)2ACAC ((Acetylacetonato)dicarbonylrhodium(I)), 2.51 wt. % tris (2,4,-di-t-butylphenyl) phosphite ligand and 97.45 wt. % Synfluid® PAO 4 cSt (Chevron Phillips Chemical Company LP, P.O. Box 4910, The Woodlands, Tex. 77387-4910, phone (800) 231-3260) inert solvent. The mixture was heated at 110° C. with agitation in the presence of a nitrogen atmosphere for two hours to produce an active rhodium catalyst solution (160 ppm rhodium, P:Rh molar ratio=25). The starting reaction mixture was composed of 37.5 wt. %, C12 linear alpha olefin feedstock, 37.5 wt. % C14 linear alpha olefin feedstock and 25 wt. % of the active rhodium catalyst solution.

The reaction was conducted in a batch process by placing the mixture in a high pressure, stainless steel autoclave, with the starting reaction mixture having a rhodium concentration of 40 ppm. The C12/C14 alpha olefin feed mixture was then isomerized at 70° C. in the presence of a CO/H2 atmosphere and 1.4 bar(g) pressure for 2.0 hours. The isomerized olefin mixture was then hydroformylated at 70° C. in the presence of a CO/H2 atmosphere and 15 bar(g) pressure for 4 hours. The molar ratio of CO to H2 in both the isomerization step and the hydroformylation step was equal to 1:1.15. The conversion of the starting olefins to aldehyde products was 97%. The composition of the resulting hydroformylation reaction product comprised 39.1 wt. % C13 aldehydes and 39.4 wt. % C15 aldehydes. The isomer distribution of the produced C13 aldehydes and C15 aldehydes was:

|                                    | Weight % |
| --- | --- |
| C13 Aldehydes | |
| 1-Tridecanal | 8.3% |
| 2-Methyl-dodecanal | 16.8% |
| 2-Ethyl-undecanal | 9.1% |
| 2-Propyl-decanal | 3.0% |
| 2-Butyl-nonanal | 1.4% |
| 2-Pentyl-octanal | 0.5% |
| Total C13 Aldehydes: | 39.1% |
| C15 Aldehydes | |
| 1-Pentadecanal | 8.3% |
| 2-Methyl-tetradecanal | 16.8% |
| 2-Ethyl-tridecanal | 9.1% |
| 2-Propyl-dodecanal | 3.0% |
| 2-Butyl-undenanal | 1.5% |
| 2-Pentyl-decanal + 2-hexyl-nonanal | 0.7% |
| Total C15 Aldehydes: | 39.4% |

The weight % branching in the branched C13 aldehyde product was 78.8%. The weight % branching in the branched C15 aldehyde product was 78.9%.

Example 6: Production of Branched C13 Aldehydes and Branched C15 Aldehydes

The batch C12/C14 alpha olefin isomerization/hydroformylation process detailed in Example 5 was repeated but with the time of the isomerization step increased from 2.0 hours to 3.0 hours and the time of the hydroformylation step decreased from 4.0 hours to 3.0 hours. The conversion of the starting olefins to aldehyde products in this run was 94%. The composition of the resulting hydroformylation reaction product comprised 38.0 wt. % C13 aldehydes and 37.9 wt. % C15 aldehydes. The isomer distribution of the produced C13 aldehydes and C15 aldehydes was:

|                                    | Weight % |
| --- | --- |
| C13 Aldehydes | |
| 1-Tridecanal | 4.3% |
| 2-Methyl-dodecanal | 10.5% |
| 2-Ethyl-undecanal | 8.1% |
| 2-Propyl-decanal | 6.3% |
| 2-Butyl-nonanal | 8.4% |
| 2-Pentyl-octanal | 0.4% |
| Total C13 Aldehydes: | 100.0% |
| C15 Aldehydes | |
| 1-Pentadecanal | 4.2% |
| 2-Methyl-tetradecanal | 10.4% |
| 2-Ethyl-tridecanal | 8.0% |
| 2-Propyl-dodecanal | 6.1% |
| 2-Butyl-undenanal | 8.7% |
| 2-Pentyl-decanal + 2-hexyl-nonanal | 0.5% |
| Total C15 Aldehydes: | 37.9% |

The weight % branching in the branched C13 aldehyde product was 88.7%. The weight % branching in the branched C15 aldehyde product was 88.9%.

Example 7: Production of Branched C13 Alcohols and Branched C15 Alcohols

The hydroformylation reaction products from Example 5 and Example 6 were combined and the mixture was flash distilled at 150-160° C. and 5 millibar absolute to recover the rhodium catalyst solution as a bottoms product and recover a mixture of branched C13 Aldehydes and branched C15 Aldehydes as an overheads product. The composition of this C13/C15 aldehyde mixture was 49.3 wt. % C13 Aldehydes and 45.0 wt. % C15 Aldehydes. The isomer distribution of the produced C13 aldehydes and C15 aldehydes was:

|                                    | Weight % |
| --- | --- |
| C13 Aldehydes | |
| 1-Tridecanal | 8.0% |
| 2-Methyl-dodecanal | 17.5% |
| 2-Ethyl-undecanal | 11.0% |
| 2-Propyl-decanal | 5.9% |
| 2-Butyl-nonanal | 3.8% |
| 2-Pentyl-octanal | 3.1% |
| Total C13 Aldehydes: | 49.3% |
| C15 Aldehydes | |
| 1-Pentadecanal | 6.8% |
| 2-Methyl-tetradecanal | 15.8% |
| 2-Ethyl-tridecanal | 10.1% |
| 2-Propyl-dodecanal | 5.4% |
| 2-Butyl-undenanal | 3.6% |
| 2-Pentyl-decanal + 2-hexyl-nonanal | 3.3% |
| Total C15 Aldehydes: | 45.0% |

The total weight % of C13 aldehydes and C15 aldehydes in the aldehyde mixture was 94.3%. The total weight % of branched C13 aldehydes and branched C15 aldehydes in the aldehyde mixture was 79.5%. The % branching in the branched C13/C15 aldehyde mixture was 84.3% (i.e. =79.5%÷94.3%). The total weight % of linear C13 aldehyde and linear C15 aldehyde in the aldehyde mixture was 14.8% (i.e. =8.0%+6.8%). The % linear aldehydes is 15.7% (i.e. =14.8%÷94.3%). The total weight % of 2-methyl branched C13 aldehyde and 2-methyl branched C15 aldehyde in the aldehyde mixture was 33.3% (i.e. =17.5%+15.8%). The % 2-methyl branched aldehydes was 35.3% (i.e. = 33.3%÷94.3%). The total weight % of 2-ethyl branched C13 aldehyde and 2-ethyl branched C15 aldehyde in the aldehyde mixture was 21.1% (i.e. =11.0%+ 10.1%). The % 2-ethyl branched aldehydes was 22.4% (i.e. =21.1%÷94.3%).

This branched C13/C15 aldehyde mixture was hydrogenated in a high pressure, stainless steel stirred autoclave at 150 C and 25 bar(g) hydrogen pressure. The hydrogenation catalyst used was a Raney® Nickel 3111 (W. R. Grace & Co., 7500 Grace Drive, Columbia, Md. 21044, US, phone 1-410-531-4000) catalyst used at a 0.50 wt. % loading. The branched Cl 3/C15 Aldehyde mixture was hydrogenated for 4 hours and the resultant reaction mixture was filtered to produce a mixture of branched C13/C15 alcohols which comprised 49.4 wt. % branched C13 alcohols and 44.1 wt. % branched C15 alcohols. The isomer distribution of the produced C13 alcohols and C15 alcohols was:

|                                    | Weight % |
| --- | --- |
| C13 Aldehydes | |
| 1-Tridecanol | 7.9% |
| 2-Methyl-dodecanol | 17.7% |
| 2-Ethyl-undecanol | 11.0% |
| 2-Propyl-decanol | 6.0% |

| | Weight % |
|---|---|
| 2-Butyl-nonanol | 3.8% |
| 2-Pentyl-octanol | 3.0% |
| Total C13 Alcohols: | 49.4% |
| C15 Alcohols | |
| 1-Pentadecanol | 6.5% |
| 2-Methyl-tetradecanol | 16.0% |
| 2-Ethyl-tridecanol | 9.5% |
| 2-Propyl-dodecanol | 5.3% |
| 2-Butyl-undenanol | 3.3% |
| 2-Pentyl-decanol + 2-hexyl-nonanol | 3.5% |
| Total C15 Alcohols: | 44.1% |

The total weight % of C13 alcohols and C15 alcohols in the alcohol mixture was 93.5%. The total weight % of branched C13 alcohols and branched C15 alcohols in the alcohol mixture was 79.1%. The % branching in the branched C13/C15 alcohol mixture was 84.6% (i.e. =79.1%±93.5%). The total weight % of linear C13 alcohol and linear C15 alcohol in the alcohol mixture was 14.4% (i.e. =7.9%+6.5%). The % linear alcohols is 15.4% (i.e. =14.4%÷93.5%). The total weight % of 2-methyl branched C13 alcohol and 2-methyl branched C15 alcohol in the alcohol mixture was 33.7% (i.e. =17.7%+16.0%). The % 2-methyl branched alcohols was 36.0% (i.e. =33.7%÷93.5%). The total weight % of 2-ethyl branched C13 alcohol and 2-ethyl branched C15 alcohol in the alcohol mixture was 20.5% (i.e. =11.0%+9.5%). The % 2-ethyl branched alcohols was 21.9% (i.e. =20.5%÷93.5%).

The hydrogenation reaction product also contained 2.4 wt. % C12 alkanes (paraffins) and 2.7 wt. % C14 alkanes (paraffins), which are products of the hydrogenation of unreacted C12 olefins and C14 olefins. These C12 and C14 alkane byproducts are removed in a straightforward manner as a "lights" stream in the distillation processes used to the refine the hydrogenation reaction product into a high purity C13 branched alcohols product and a high purity branched C15 alcohols product.

Example 8

Production of a Branched C15 Aldehyde/C15 Alcohol Product with a Cobalt Catalyst A C14 linear alpha olefin feedstock (1-Tetradecene) was obtained from the Chevron Phillips Chemical Company LP, identified by product name AlphaPlus® 1-Tetradecene (Chevron Phillips Chemical Company LP, P.O. Box 4910, The Woodlands, Tex. 77387-4910, US, phone (800) 231-3260). The homogeneous cobalt organophosphorus catalyst solution used in this example was a mixture comprised of 1.36 wt. % Cobalt(II) 2-Ethylhexanoate (65% solution), 16.44 wt. % tris (2,4,-di-t-butylphenyl) phosphite ligand and 82.2 wt. % Synfluid® PAO 4 cSt (Chevron Phillips Chemical Company LP) inert solvent. The mixture was heated at 150° C. with agitation in the presence of a nitrogen atmosphere for two hours to produce an active cobalt catalyst solution (1500 ppm cobalt, P:Co molar ratio=10). The starting reaction mixture was composed of 53.3 wt. % C14 linear alpha olefin feedstock and 46.7 wt. % of the active cobalt catalyst solution.

The reaction was conducted in a batch process by placing the mixture in a high pressure, stainless steel autoclave, with the starting reaction mixture having a cobalt concentration of 700 ppm. The C14 alpha olefin feed mixture was then isomerized at 180° C. in the presence of a CO/H2 atmosphere and 20 bar(g) pressure for 3 hours. The isomerized olefin mixture was then hydroformylated at 180° C. in the presence of a CO/H2 atmosphere and 60 bar(g) pressure for 3 hours. The molar ratio of CO to H2 in both the isomerization step and the hydroformylation step was equal to 1:1.1. The conversion of the starting olefins to aldehyde and alcohol products was 69.6%. The resulting hydroformylation reaction product was comprised of a mixture of C15 aldehydes and C15 alcohols. The isomer distribution of the mixture of C15 aldehydes and C15 alcohols was:

| C15 Aldehydes | |
|---|---|
| 1-Pentadecanal | 30.2% |
| 2-Methyl-tetradecanal | 13.2% |
| 2-Ethyl-tridecanal | 6.2% |
| 2-Propyl-dodecanal | 4.8% |
| 2-Butyl/2-Pentyl/2-Hexyl Isomers | 13.8% |
| Total C15 Aldehydes: | 68.2% |
| C15 Alcohols | |
| 1-Pentadecanol | 18.9% |
| 2-Methyl-tetradecanol | 8.7% |
| 2-Ethyl-tridecanol | 1.8% |
| 2-Propyl/2-Butyl/2-Pentyl/2-Hexyl | 2.4% |
| Total C15 Alcohols: | 31.8% |

The weight % linearity in C15 aldehyde/alcohol mixture was 49.1%. The weight % branching in the C15 aldehyde/alcohol mixture was 50.9%. The weight % of 2-methyl isomers in the C15 aldehyde/alcohol mixture was 21.9%. The weight % of 2-ethyl isomers in the C15 aldehyde/alcohol mixture was 8.0%. The combined weight % of 2-propyl/2-butyl/2-pentyl/2-hexyl isomers in the C15 aldehyde/alcohol mixture was 21.0%.

Example 9

Production of a Branched C15 Aldehyde/C15 Alcohol Product with a Mixed Cobalt/Rhodium Catalyst A C14 linear alpha olefin feedstock (1-Tetradecene) was obtained from the Chevron Phillips Chemical Company LP, identified by product name AlphaPlus® 1-Tetradecene (Chevron Phillips Chemical Company LP, P.O. Box 4910, The Woodlands, Tex. 77387-4910, US, phone (800) 231-3260). The homogeneous cobalt-rhodium organophosphorus catalyst solution used in this example was a mixture comprised of 1.36 wt. % Cobalt(II) 2-Ethylhexanoate (65% solution), 0.005 wt. % Rh(CO)2ACAC ((Acetylacetonato) dicarbonylrhodium(I)), 16.44 wt. % tris (2,4,-di-t-butylphenyl) phosphite ligand and 82.2 wt % Synfluid® PAO 4 cSt (Chevron Phillips Chemical Company LP, P.O. Box 4910, The Woodlands, Tex. 77387-4910, US, phone (800) 231-3260) inert solvent. The mixture was heated at 150° C. with agitation in the presence of a nitrogen atmosphere for two hours to produce an active cobalt-rhodium catalyst solution (1500 ppm cobalt, P:Co molar ratio=10, 21 ppm rhodium). The starting reaction mixture was composed of 53.3 wt. % C14 linear alpha olefin feedstock and 46.7 wt. % of the active cobalt-rhodium catalyst solution.

The reaction was conducted in a batch process by placing the mixture in a high pressure, stainless steel autoclave, with the starting reaction mixture having a cobalt concentration of 700 ppm and a rhodium concentration of 10 ppm. The C14 alpha olefin feed mixture was then isomerized at 80° C.

in the presence of a CO/H2 atmosphere and 2 bar(g) pressure for 1.5 hours. The isomerized olefin mixture was then hydroformylated at 180° C. in the presence of a CO/H2 atmosphere and 30 bar(g) pressure for 2.5 hours. The molar ratio of CO to H2 in both the isomerization step and the hydroformylation step was equal to 1:1.1. The conversion of the starting olefins to aldehyde and alcohol products was 83.0%. The resulting hydroformylation reaction product was comprised of a mixture of C15 aldehydes and C15 alcohols. The isomer distribution of the mixture of C15 aldehydes and C15 alcohols was:

| C15 Aldehydes | |
|---|---|
| 1-Pentadecanal | 29.2% |
| 2-Methyl-tetradecanal | 35.3% |
| 2-Ethyl-tridecanal | 8.9% |
| 2-Propyl-dodecanal | 5.3% |
| 2-Butyl/2-Pentyl/2-Hexyl Isomers | 12.3% |
| Total C15 Aldehydes: | 91.0% |
| C15 Alcohols | |
| 1-Pentadecanol | 4.1% |
| 2-Methyl-tetradecanol | 3.8% |
| 2-Ethyl-tridecanol | 0.8% |
| 2-Propyl/2-Butyl/2-Pentyl/2-Hexyl | 0.3% |
| Total C15 Alcohols: | 9.0% |

The weight % linearity in C15 aldehyde/alcohol mixture was 33.3%. The weight % branching in the C15 aldehyde/alcohol mixture was 66.7%. The weight % of 2-methyl isomers in the C15 aldehyde/alcohol mixture was 39.1%. The weight % of 2-ethyl isomers in the C15 aldehyde/alcohol mixture was 9.7%. The combined weight % of 2-propyl/2-butyl/2-pentyl/2-hexyl isomers in the C15 aldehyde/alcohol mixture was 18.0%.

CONCLUSION

This disclosure regards branched products and methods for producing and manufacturing branched products in their many aspects, features and elements. Such compounds and manufacturing processes can be dynamic in its use and operation. This disclosure is intended to encompass the equivalents, means, systems and methods of the use of the branched products and methods for producing and manufacturing branched products and their many aspects consistent with the description and spirit of the apparatus, means, methods, functions and operations disclosed herein. Other embodiments and modifications will be recognized by one of ordinary skill in the art as being enabled by and within the scope of this disclosure.

The scope of this disclosure is to be broadly construed. The embodiments herein can be used together, separately, mixed or combined. It is intended that this disclosure disclose equivalents, means, systems and methods to achieve the devices, designs, operations, control systems, controls, activities, mechanical actions, dynamics and results disclosed herein. For each compound, process, method, manufacturing method, mechanical element or mechanism disclosed, it is intended that this disclosure also encompasses within the scope of its disclosure and teaches equivalents, means, systems and methods for practicing the many aspects, compounds, processes, mechanisms and devices disclosed herein. The claims of this application are likewise to be broadly construed.

The description of the technology herein in its many and varied embodiments is merely exemplary in nature and, thus, variations that do not depart from the gist of the disclosure are intended to be within the scope of the claims and the disclosure herein. Such variations are not to be regarded as a departure from the spirit and scope of the disclosed technologies.

It will be appreciated that various modifications and changes can be made to the above-described embodiments of the processes and resulting branched products as disclosed herein without departing from the spirit and the scope of the claims.

We claim:

1. A composition, comprising:
a mixture of C7-C37 aldehydes,
wherein less than 60 wt. % of the mixture of C7-C37 aldehydes are linear aldehydes,
wherein greater than 25 wt. % of the mixture of C7-C37 aldehydes are 2-methyl branched aldehydes, and
wherein greater than 8 wt. % of the mixture of C7-C37 aldehydes are 2-ethyl branched aldehydes, and
wherein the mixture of C7-C37 aldehydes has aldehydes of at least two different chain lengths.

2. The composition of claim 1, wherein greater than 10 wt. % of the aldehydes are 2-ethyl branched aldehydes.

3. The composition of claim 1, wherein greater than 12 wt. % of the aldehydes are 2-ethyl branched aldehydes.

4. The composition of claim 1, wherein greater than 14 wt. % of the aldehydes are 2-ethyl branched aldehydes.

5. The composition of claim 1, wherein greater than 16 wt. % of the aldehydes are 2-ethyl branched aldehydes.

6. The composition of claim 1, wherein greater than 18 wt. % of the aldehydes are 2-ethyl branched aldehydes.

7. The composition of claim 1, wherein greater than 20 wt. % of the aldehydes are 2-ethyl branched aldehydes.

8. A composition, comprising:
a mixture of C7-C37 aldehydes,
wherein less than 60 wt. % of the mixture of C7-C37 aldehydes are linear aldehydes,
wherein greater than 25 wt. % of the mixture of C7-C37 aldehydes are 2-methyl branched aldehydes,
wherein greater than 8 wt. % of the mixture of C7-C37 aldehydes are 2-ethyl branched aldehydes,
wherein greater than 1.5 wt. % of the mixture of C7-C37 aldehydes are 2-propyl branched aldehydes,
wherein greater than 0.5 wt. % of the mixture of C7-C37 aldehydes are 2-butyl branched aldehydes, and
wherein the mixture of C7-C37 aldehydes has aldehydes of at least two different chain lengths.

9. The composition of claim 8, wherein greater than 2 wt. % of the aldehydes are 2-propyl branched aldehydes and greater than 2 wt. % of the branched aldehydes are 2-butyl branched aldehydes.

10. The composition of claim 8, wherein greater than 4 wt. % of the aldehydes are 2-propyl branched aldehydes and greater than 4 wt. % of the branched aldehydes are 2-butyl branched aldehydes.

11. The composition of claim 8, wherein greater than 6 wt. % of the aldehydes are 2-propyl branched aldehydes and greater than 6 wt. % of the branched aldehydes are 2-butyl branched aldehydes.

12. The composition of claim 8, wherein greater than 8 wt. % of the aldehydes are 2-propyl branched aldehydes and greater than 8 wt. % of the branched aldehydes are 2-butyl branched aldehydes.

* * * * *